(12) United States Patent
Arinzeh et al.

(10) Patent No.: US 10,197,563 B2
(45) Date of Patent: Feb. 5, 2019

(54) 3-D IN VITRO MODEL FOR BREAST CANCER DORMANCY

(71) Applicants: New Jersey Institute of Technology, Newark, NJ (US); Rutgers, The State University of New Jersry, New Brunswick, NJ (US)

(72) Inventors: Treena Lynne Arinzeh, West Orange, NJ (US); Pranela Rameshwar, Maplewood, NJ (US); Khadidiatou T. Guiro, Newark, NJ (US)

(73) Assignees: New Jersey Institute of Technology, Newark, NJ (US); Rutgers, The State University of New Jersry, New Brunswick, NJ (US)

( * ) Notice: Subject to any disclaimer, the term of this patent is extended or adjusted under 35 U.S.C. 154(b) by 0 days.

(21) Appl. No.: 15/348,758

(22) Filed: Nov. 10, 2016

(65) Prior Publication Data

US 2017/0131273 A1 May 11, 2017

Related U.S. Application Data

(60) Provisional application No. 62/253,454, filed on Nov. 10, 2015.

(51) Int. Cl.
| | |
|---|---|
| *G01N 33/543* | (2006.01) |
| *G01N 33/574* | (2006.01) |
| *C12Q 1/6886* | (2018.01) |
| *C12N 5/00* | (2006.01) |
| *C12N 5/09* | (2010.01) |

(52) U.S. Cl.
CPC ..... *G01N 33/54346* (2013.01); *C12N 5/0062* (2013.01); *C12N 5/0693* (2013.01); *C12Q 1/6886* (2013.01); *G01N 33/57415* (2013.01); *C12N 2533/18* (2013.01); *C12Q 2600/158* (2013.01); *C12Q 2600/178* (2013.01)

(58) Field of Classification Search
CPC ....... G01N 33/54346; G01N 33/57415; C12N 5/0063; C12N 5/6886; C12N 2533/18; C12Q 1/6886; C12Q 2600/158; C12Q 2600/178
USPC ...................................................... 435/7.21
See application file for complete search history.

(56) References Cited

U.S. PATENT DOCUMENTS 6,368,596 B1 4/2002 Ghetie et al.

FOREIGN PATENT DOCUMENTS

WO 2004014292 A2 2/2004

OTHER PUBLICATIONS

Pathi et al., Hydroxyapatite nanoparticle-containing scaffolds for the study of breast cancer bone metastasis; Biomaterials, 32 (2011 ) pp. 5112-5122.*
Wutticharoenmongkol et al., Preparation and Characterization of Novel Bone Scaffolds Based on Electrospun Polycaprolactone Fibers Filled with Nanoparticles, Macromolecular Bioscience, 6 (2006) pp. 70-77.*
Karavasili et al., Preparation and characterization of multiactive electrospun fibers: Poly-e-carpolactone fibers loaded with hydroxyapatite and selected NSAIDs, Journal of Biomedical Material Research A, vol. 102A, Iss. 8 (2014) pp. 2583-2589.*
Patlolla et al., Evaluating Apatite Formation and Osteogenic Activity of Electrospun Composites for Bone Tissue Engineering, Biotechnology and Bioengineering, vol. 111, No. 5 (2014) pp. 1000-1017.*
Rezaei et al., In vitro study of hydroxyapatite/polycaprolactone (HA/PCL) nanocompsite synthesized by an in situ sol-gel process, Materials Science and Engineering, C 33 (2013) pp. 390-396.*
Taubenberger, In vitro microenvironments to study breast cancer bone colonization, Advanced Drug Delivery Reviews, 79-80 (2014) pp. 135-144.*
Barkan, et al., Inhibition of Metastic Outgrowth From Single Dormant Tumor Cells by Targeting the Cytoskeleton, Cancer Res. Aug. 1, 2008, 68 (15), pp. 6241-6250.

\* cited by examiner

*Primary Examiner* — Jennifer M. H. Tichy
(74) *Attorney, Agent, or Firm* — Lerner, David, Littenberg, Krumholz & Mentlik, LLP

(57) ABSTRACT

Disclosed is a three-dimensional (3-D) in vitro model for studying and subsequently treating cancer dormancy. The model is specifically useful in studying breast cancer and may be used for drug discovery because it maintains the breast cancer cells in a dormant state, unlike conventional two-dimensional (2-D) tissue culture plastic (TCP). Tumor-forming breast cancers cells were seeded on the 3-D model scaffolds and remained viable without proliferation. They also express stem cell markers typical for dormant cells. Dormant breast cancer cells also maintain their phenotype when seeded on the 3-D model unlike conventional 2-D models. The 3-D model includes a fibrous polycaprolactone with 30 wt. % hydroxyapatite. The 3-D model mimics the structure of bone tissue.

9 Claims, 64 Drawing Sheets
(46 of 64 Drawing Sheet(s) Filed in Color)

3-D IN VITRO MODEL FOR BREAST CANCER DORMANCY

CROSS-REFERENCE TO RELATED APPLICATIONS

The present application claims the benefit of the filing date of U.S. Provisional Patent Application No. 62/253,454 filed Nov. 10, 2015, the disclosure of which is hereby incorporated herein by reference.

FIELD

This invention relates to a 3-D fibrous scaffold and its use as an in vitro model to study breast cancer dormancy.

BACKGROUND

Breast cancer has been reported to home to the bone microenvironment and to adapt a quiescent phenotype in regions close to the endosteum, among the BM stromal compartment. About 85% of BC patients have osteolytic metastasis, and currently there is no detection method for BC metastases before osteolytic lesion onset.

Several models have investigated breast cancer cell-bone interactions in a two-dimensional (2-D) approach. It has been determined that this approach does not adequately represent the three-dimensional (3-D) in-vivo microenvironment. Thus 3D polymeric scaffolds can be an innovative strategy to mimic the tumor microenvironment in culture. Many research groups have begun studies looking into the cellular and molecular mechanisms involved between tumor cells and the bone microenvironment via 3-D matrices. However, most of these studies have been limited to matrices consisting of purified proteins such as collagen gels/collagen coatings which fail to portray the normal bone environment encountered by a single breast cancer cell in the metastatic process. Thus there remains a need for additional 3-D models.

BRIEF SUMMARY

This invention relates to a three-dimensional (3-D) in vitro model for studying breast cancer dormancy. The model can be used for drug discovery because it maintains the breast cancer cells in a dormant state, unlike conventional two-dimensional (2-D) tissue culture plastic (TCP). The tumor-forming breast cancer cells when seeded on the 3-D model remains viable but do not proliferate. They also express stem cell markers typical for dormant cells. On conventional TCP, the tumor-forming aggressive cells remain proliferative. Dormant breast cancer cells also maintain their phenotype when seeded on the 3-D model. When the dormant cells are seeded on TCP, they also begin to proliferate in culture, unable to maintain the dormant phenotype. The 3-D model consists of fibrous polycaprolactone with 30 wt. % hydroxyapatite. The 3-D model mimics the structure of bone tissue.

BRIEF DESCRIPTION OF THE FIGURES

The patent or application file contains at least one drawing executed in color. Copies of this patent or patent application publication with color drawing(s) will be provided by the Office upon request and payment of the necessary fee. So that those having ordinary skill in the art will have a better understanding of how to make and use the disclosed composition and methods, reference is made to the accompanying figures wherein.

DETAILED DESCRIPTION

Figure 1:
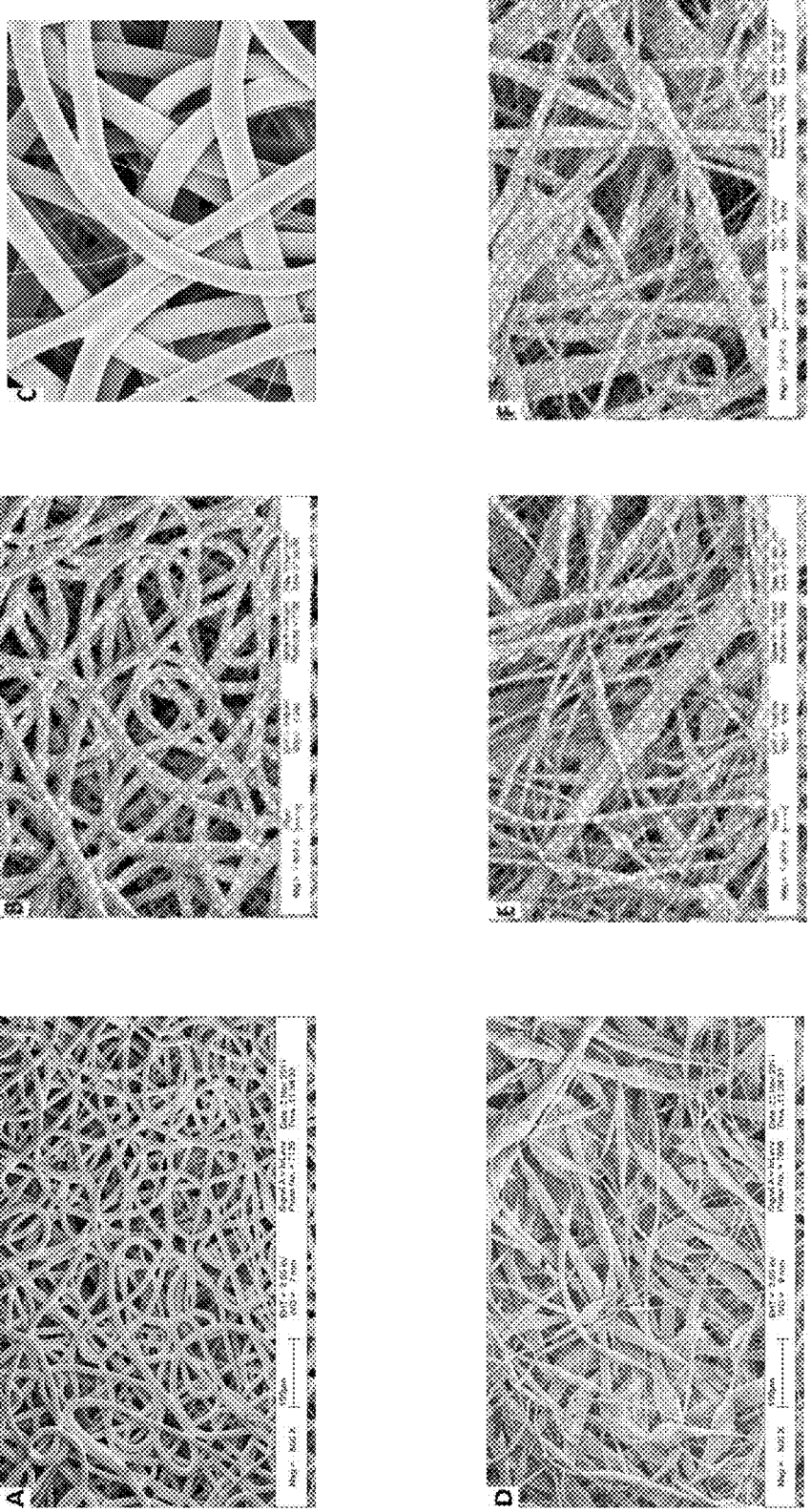
FIG. 1 shows SEM images taken at 500×, 1000×, and 2500×, respectively for random PCL (A-C), PCL+HA (D-F) of random fibrous scaffolds.
Figure 2:
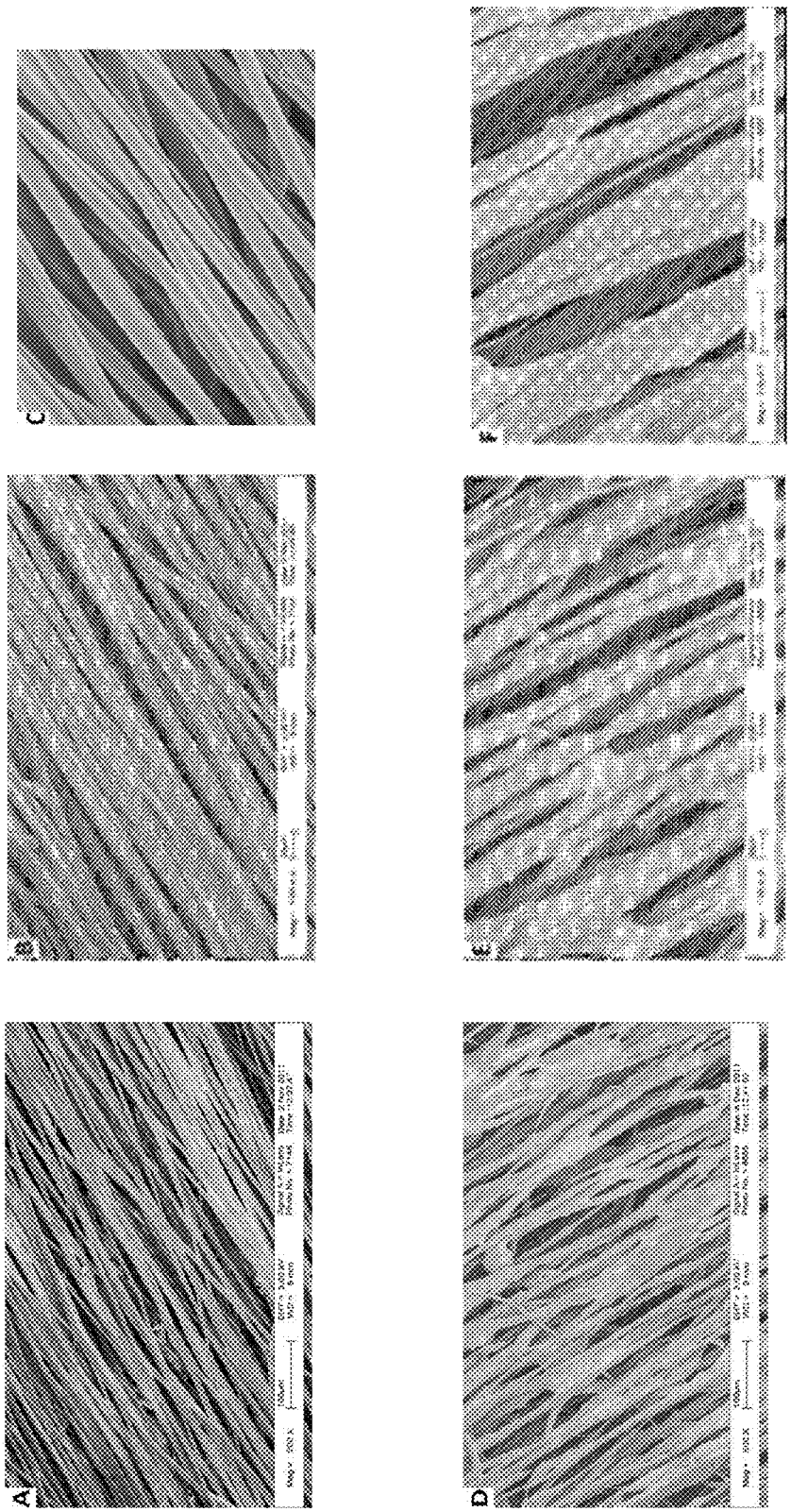
FIG. 2 shows SEM images taken at 500×, 1000×, and 2500×, respectively for PCL (A-C), PCL+HA (D-F) aligned fibrous scaffolds.

Prior studies have established a 3-D model and ascertained the effect of architectural features (i.e. fiber orientation) on BCC growth, migration and cell-cell interaction. The findings established a platform to study dormancy in a bone-mimetic microenvironment to further evaluate dormancy more closely by drug resistance and cell cycle analysis.

Thus the effect of the three-dimensional PCL+HA random and PCL+HA aligned fibrous bone mimetic scaffolds on BCCs behavior in vitro to better understand the BC-bone microenvironment. Moreover, engineered nonwoven scaffolds have found application in the field of tissue engineering. During bone tissue formation, collagen fibers were deposited as part of the ECM. These fibers act like a construct, onto which apatite crystals were deposited, forming the earliest phase of bone. The fibrous scaffold played a significant role in regulating cell attachment, proliferation, and differentiation. Also, changes in protein and gene levels were examined alongside miRNA expression profiles to understand further the mechanism of dormancy within this bonelike microenvironment.

In summary, breast cancer cells are known to metastasize to the bone marrow microenvironment, where they can home and remain dormant and resistant to chemotherapy leading to potential disease recurrence. In this chapter, using the electrospinning method we have utilized our fabricated 3-D microfibrous bone scaffold to evaluate the effect of the fibrous architectural features and chemical cues (HA) on BCC attachment, migration, growth, viability, cell cycle, gene and protein expressions. Non-treated MDA-MB-231 cells have a highly proliferative and aggressive phenotype, unlike the carboplatin treated cells (treated) MDA-MB-231 cells which have been known to have chemoresistant, and dormant phenotypes. Results indicate that this 3-D culture model of bone with random fibrous architecture (mimicking newly formed bone) has stimulated the dormant cancer cells to become less dormant, suggesting that the cell may be becoming a more invasive phenotype, while the non-treated MDA-MB-231 cells kept maintained some characteristics of the aggressive phenotype. Thus it has been found that 3-D culture conditions affect BCC behavior which can lead to the design of therapies to target dormant BCCs in vitro.

In these studies, PCL+HA random and PCL+HA aligned fibrous scaffolds were used to study the behavior of non-treated MDA-MB-231 cells and treated MDA-MB-231 cells.

Using the electrospinning method, both random and aligned PCL fibrous scaffolds with uniform fiber morphology were fabricated for 3-D culture. The fibrous constructs produced by the electrospinning process have a high surface area-to-volume ratio, which can provide more surface for cell attachment as compared to TCP. We were able to fabricate random and aligned fibers with micron-sized fiber diameters. In tissue engineering, previous and recent studies have suggested a need for nanofibers for tissue formation and vascularization. However, the micron-sized fiber dimension more closely mimics the collagen fibers, which are bundled collagen fibrils, found in the native ECM. Microfiber scaffolds, in contrast to nanofiber scaffolds, have larger interfiber spacing, which can better support cell infiltration and may promote an in vivo-like metastatic phenotype in terms of tumor morphogenesis (formation of spheroids), and migratory behavior related to the high invasiveness of MDA-MB-231 cells. Moreover, the moduli of elasticity for our random and aligned fibers were higher than epithelial basement membrane (~0.5 MPa) yet lower than collagen (~9 MPa). However, the elastic modulus of TCP that served as a 2-D control is 2.5 Gpa, which are three to four orders of magnitude higher than all our fibrous scaffolds. The compliance of the extracellular matrix differs between tissues and it is altered in tumors. For instance, results by prior researchers showed that the elastic modulus of the ECM has an effect on mammary epithelial cell morphogenesis that correlates with changes in actin organization and anti-apoptotic behavior. The release of calcium and phosphate ions from the PCL+HA fibrous scaffolds into the solution was measured, and there was no release from and the PCL+HA during the 7-day culture period. Our findings suggested that these fabricated scaffolds were stable over the 7-day culture period. Studies have shown that the presence of HA may stimulate an increase in extracellular Ca2+ concentrations, which can affect cancer cell behavior. Nonetheless, we did not detect high levels of Ca2+ concentrations in media collected from PCL+HA scaffolds and perhaps this can be due to HA not being highly soluble in the absence of strongly acidic conditions. Thus at the completion of this chapter, scaffolds were fabricated and characterized by various properties.

Non-treated MDA-MB-231 cells and treated MDA-MB-231 cells cultured on these bone mimetic scaffolds showed changes in cell morphology, adherence viability, and growth. Visually analyzing the sub-volumes of cells in the 3-D-reconstructed Z-stack images showed that cells were able to penetrate the fibrous scaffolds and resided within the different scaffold layers. The results showed that non-treated cells on PCL+HA random fibers, had a mesenchymal morphology at day 1 which appeared to be more elongated along the fibrous structures of the scaffolds and a more rounded shape by day 7. On PCL+HA aligned fibers, non-treated cells had a mesenchymal morphology at both days 1 and 7, which appeared to be more elongated along the fibrous structures of the scaffold. Unlike cells on fibrous scaffolds, non-treated cells on TCP surface displayed confluency by day 7. These findings suggested that on fibrous bone-mimetic scaffolds, BCCs had the ability to reorient themselves in order to migrate through both random and aligned fibers. Moreover, treated MDA-MB-231 cells on both PCL+HA random and aligned fibers had a morphology that was spread on both days 1 and 7 with cell bodies stretched along the fibers. Treated cells also appeared to interact well with the fibrous scaffolds, with some cells enveloping the fibers. At day 7 on the fibrous scaffolds, treated cells displayed elongated cytoskeletal structures showing filaments similar to cells with lamellipodia, which are usually found on very mobile cells.

To further verify whether the fibrous bone scaffolds could support the growth and viability of BCCs, MDA-MB-231 cells were examined in the 3-D PCL+HA fibrous scaffold environment. Non-treated MDA-MB-231 cells displayed significant increase in cell number during the 7 day-culture period on TCP. On fibrous bone scaffolds, non-treated cells showed a significant decrease in growth suggesting that the fibrous scaffolds probed these usually aggressive BCCs to transition to a less aggressive phenotype. Treated MDA-MB-231 cells on TCP, showed a significant increase at day 7 as compared to days 1 and 4; while on PCL+HA random scaffolds treated cells did not show change in growth over the 7-day culture period. This suggested that on random bone scaffolds, resistant cells maintained their non-proliferative behavior during the 7-day culture. However on PCL+HA aligned fibers, treated cells showed a significant decrease in growth at day 7; suggesting along with the presence of HA fiber orientation within the bone environment can also affect the proliferative behavior of resistant cells. Thus these findings corroborated that there is a significant difference in growth rate of BCCs on 2D monolayer surfaces versus 3D fibrous bone mimetic scaffolds suggesting that these BCCs were able to sense the difference in microenvironment.

The metabolic activity of BCCs on these bone mimetic scaffolds was investigated. In agreement with the proliferation data, non-treated cells showed a significant increase in metabolic activity on TCP throughout the 7-day culture period unlike on PCL+HA fibrous scaffolds where cells had a significantly low metabolic activity. This suggested that the bone scaffolds could also modulate the behavior of these usually aggressive BCCs to transition into less metabolically active cells. Treated cells however seemed to be affected differently on PCL+HA scaffolds. The results showed that treated cells had an increase in metabolic activity by day 7 on bone mimetic scaffolds unlike on TCP where there was no difference in metabolic activity during the 7-day culture period. These results suggested that the bone scaffolds have the potential of changing the metabolic activity. Thus, similar to the proliferation results, analyzing the metabolic activity of the BCCs at different time points also revealed a significant difference in activity of the BCCs on the 2D monolayer versus 3D fibrous bone scaffolds. These results inferred that on the bone scaffolds, the usually aggressive and highly metabolic active MDA-MB-231 cells adopted a lower metabolic activity by day 7 and the treated MDA-MB-231 cells, which are associated with low metabolic activity, adopted a more metabolically active phenotype by day 7.

Following was the evaluation of cyclin D1 expression, a $G_1/S$ transition protein which has been shown to regulate proliferation in BC. The results showed that during the 7-day culture period non-treated MDA-MB-231 cells expressed little to no cyclin D1 on TCP. On all bone mimetic scaffolds, non-treated MDA-MB-231 cells expressed cyclin D1 throughout the 7-day culture as well. Similar to TCP, treated cells expressed cyclin D1 on all bone like scaffolds throughout the 7-day culture period. These results suggested that on bone scaffolds, non-treated MDA-MB-231 cells adopted a low cycling behavior similar to the treated MDA-MB-231 cells. Next the cell cycle phases of BCCs on the bone scaffolds were investigated. The findings indicated that on TCP, more than 60% of non-treated MDA-MB-231 cells were in S phase of the cell cycle for the 7-day culture period. On PCL+HA fibers, when day 1 was compared to day 7, non-treated cells were more equally distributed between G0/G1 phase and S phase on PCL+HA scaffolds than on TCP. More than 60% of treated MDA-MB-231 cells were G0/G1 phase of the cell cycle for the 7-day culture period on TCP. On PCL+HA fibers, at day 1, more treated cells were in the in G0/G1 phase than the S phase; while at day 7, treated MDA-MB-231 cells were cycling on both PCL+HA random fibers and TCP controls.

Moreover migration results showed that the bone scaffold fiber orientation does affect the migration behavior of non-treated cells and treated cells. Non-treated cells had a significantly lower migration speed on random bone scaffolds than on aligned fibrous scaffolds. However, non-treated cells migrated further within the random bone fibrous scaffolds than within the aligned bone fibers. The results suggested that both bone fiber orientations could modulate the migratory behavior of non-treated cells. Treated cells had significantly low migration speed on random bone scaffolds than on aligned bone fibers. Similarly, treated cells migrated further within the aligned bone scaffolds than within the random bone scaffolds. These results suggested that also both bone fiber orientation could regulate the behavior of treated cells.

Non-treated migration speed results seemed to be in agreement with the cell cycle, proliferation and metabolic activity data where non-treated cells adopted a low cycling, low proliferating and low metabolic activity profile similar to treated (dormant) cells behavior. This is specifically for non-treated cells on random bone scaffolds where they had a low migration speed similar to the treated cells on the random bone scaffolds. Treated cells migration speed and invasion distance on random bone scaffolds seemed to be in agreement as well with our previous findings that suggested that on random bone scaffolds, resistant cells maintained their non-proliferative behavior during the 7-day culture.

BCSCs have been shown to have the capacity for long-term self-renewal, to transition to a dormant phenotype and resist existing therapeutic agents such as carboplatin, and initiate distant metastatic disease. Oct-4 is a protein that plays a critical role in the self-renewal of undifferentiated embryonic stem cells. Another oncogene that plays an important role in many phases of mammalian development is Sox2 and research associated with induced pluripotency. SOX2 is a transcription factor that is critical for maintaining self-renewal, or pluripotency, of undifferentiated embryonic stem cells. Several studies have associated loss of cell cycle control in tumorigenesis and resistance to chemotherapeutic agents. Specific genes that are involved in regulating the cell cycle are members of a family called cyclin-dependent kinases (CDK). CDKs and cyclins together regulate progression through different phases of the cell cycle. Cyclins are specific proteins produced and degraded during each cell cycle. For instance, as previously mentioned, cyclin D1 controls the transition of the cell cycle from G1 to S phase. In BC, over-expression of cyclin D1 is usually associated with poor survival of patients.

Several researchers have investigated the regulation of apoptosis in BC because deregulation in apoptosis can lead to disease such as cancer. Usually, apoptosis plays an important role in eliminating unwanted cells and damaged cells from the body. Apoptosis can be described as a genetically controlled process where cells undergo an organized programmed series of intracellular events leading to death in response to specific signals. In tumorigenesis, a significant factor is a balance between the pro-apoptotic and anti-apoptotic members of Bcl2 family. The Bcl2 family comprising of pro-apoptotic (Bax, BAD, Bak, Bic and Bok) or anti-apoptotic (including Bcl2, Bcl-xL, and Bcl-w) members regulate mitochondrial outer membrane permeabilization. Bcl2 is considered as an oncogene that contributes to tumor development due to inhibition of apoptosis and shown to be upregulated in many cancers such as BC. Usually a mutation of Bcl2 gene in a cancer cell leading to increased expression will down-regulate the normal function of the pro-apoptotic proteins, BAX, and BAK. Moreover, as shown by previous researchers, Bcl2 over-expression results in the resistance of cells to different drugs. Past research also has shown that Bcl2 gene expression can be linked to a bad prognosis for tumor progression.

Progress in BC chemotherapy treatment has been hindered by the development of tumors with a Multiple Drug Resistance (MDR) phenotype, which is one of the major causes of failures to chemotherapy. MDR phenotype is most predominant in aggressive cancer such as BC and ovarian cancer. MDR can be defined by the resistance developed by some tumors to protect themselves against some structurally and functionally unrelated chemotherapeutic agents. It is known and has been described to use MDR to develop as the result of treatment of tumor cells by a drug along with the type of cell differentiation or genetic profile of tumor cells. Researchers described MDR as a combination of multiple mechanisms that can act either alone or in concert with each other for the development of the MDR phenotype. Studies in the past by researchers have shown that the microenvironment has been considered to be a major mechanism of drug resistance because of several factors. First, this environment can obstruct direct drug access to cancer cells as compared to TCP thus reducing the efficiency of the drug. Secondly, with the structure of the ECM, this drug resistance can come from decreased cell-cell contact and cell-matrix interaction, usually resulting in decreased proliferation. Lastly, some conditions of the microenvironment such as hypoxia, for instance, can be favorable to CSCs, which leads to increased resistance to cell death.

At the gene levels, the results indicated that between TCP and the different bone-like scaffolds were made, there was no significant difference in expression of the OCT4 gene at day 1 between different surfaces. At day 7, non-treated cells expressed OCT4 gene significantly higher on random fibrous bone-like scaffolds as compared to TCP and aligned fibrous bone-like scaffolds. These findings suggested these usually aggressive cells have increased stem characteristics at day 7 on random fibrous bone-like scaffolds, showing that this random oriented fibrous 3-D bone mimetic microenvironment have the ability to enhance stem cell populations at day 7. Non-treated cells expressed SOX2 gene significantly lower on random fibrous bone-like scaffolds as compared to TCP and aligned fibrous bone-like scaffolds at day 1. At day 7, non-treated cells expressed higher levels of SOX2 on random fibrous bone-like scaffolds as compared to TCP. These findings were in agreement with the OCT4 gene expression profile previously described, essentially suggesting an increase in self-renewal properties of these usually aggressive BCCs when in contact with random bone-like scaffold at day 7. Non-treated MDA-MB-231 cells had significantly higher expression of Cyclin D1 gene at both day 1 and day 7 on random fibrous bone-like scaffolds than on both TCP and aligned fibrous bone-like scaffolds. These findings suggested an increased expression of the G1 to S cell cycle proteins suggesting that on the random bone like scaffolds most of the usually aggressive BCCs were in G1 or cell cycle arrested at day 1 and at day 7 relative to cells on 2-D monolayers or on aligned bone-like scaffolds. There was no significant difference in BCL2 gene expression between different surfaces at day 1. At day 7, BCL2 was expressed significantly higher on random fibrous bone-like scaffolds as compared to aligned fibrous bone-like scaffolds. These findings suggested that on random fibrous bone like scaffolds at day 7, there is an increase in the anti-apoptosis potential of the cells which also is in agreement with the expression of OCT4, SOX2 and Cyclin D1 genes previously described. MDR1 expression was significantly lower at day 1 on random fibrous bone-like scaffolds as compared to both TCP and aligned fibrous bone-like scaffolds. MDR1 was expressed significantly higher at day 7 on aligned fibrous bone-like scaffolds as compared to both TCP and random fibrous bone-like scaffolds. These findings suggested that on bone-like scaffolds with aligned oriented fibers, the usually aggressive BCCs have significant increase in drug resistance characteristics.

When comparisons between TCP and the different scaffolds were made, treated cells had no significant difference in expression of the OCT4 gene at day 1. At day 7 treated cells had a significantly higher OCT4 gene expression on random fibrous bone-like scaffolds as compared to TCP and aligned fibrous bone like scaffolds. These findings suggested on random bone-like fibrous scaffolds, treated cells had an increase in stem characteristics, which represent the dormant (stem-like breast cancer) cells. Treated cells expressed SOX2 gene significantly lower on both random and aligned fibrous bone-like scaffolds than on TCP at day 1. At day 7, there was no significant difference in SOX2 gene expression between different groups. These findings depicted a maintained level of SOX2 expression on all surfaces at day 7 suggesting that the self-renewal properties of these treated cells was not reduced by the change in environment. For Cyclin D1 gene expression, treated MDA-MB-231 cells had significantly higher expression on random fibrous scaffolds than on TCP and aligned fibrous bone-like scaffolds at day 1. At day 7, there was no significant difference in Cyclin D1 expression between groups. These findings indicated that treated cells have maintained their cell cycling properties on the random bone-like fibrous scaffolds and these results were in agreement with the OCT4 and SOX2 gene expression previously described. Similarly, there was no significant difference in BCL2 gene expression between TCP, random and aligned fibrous bone-like scaffolds on both day 1 and day 7 suggesting that the treated cells also maintained their anti-apoptosis characteristics on the bone-like scaffolds. MDR1 expression was significantly lower at day 1 on random bone-like fibrous scaffolds as compared to both TCP and aligned fibrous bone-like scaffolds. At day 7, MDR1 gene was expressed significantly lower on both random and aligned fibrous scaffolds as compared to TCP. These findings suggested that the bone-like scaffolds have the potential of affecting the drug resistance characteristics of the treated cells.

Subsequently the protein expression of BCCs on the bone scaffolds was studied. The findings showed that during the 7-day culture period on TCP, non-treated cells had little to no Oct-4 protein, high expression of Sox2, expression of Bax with a significantly high expression of Bcl2 protein. By day 7 in culture on PCL+HA random fibers, non-treated cells had increased expression in Oct-4 and Sox2 protein expression, low expression of Bax protein with reduced but high expression of bcl2 protein. These results suggested that the usually aggressive BCCs on random bone like scaffolds have expressed increased protein for stem cell markers, with the presence of low cell death and high anti-apoptotic proteins. Non-treated cells on PCL+HA aligned fibers by day 7 in culture, had low Oct-4 protein expression which was similar to TCP, and high Sox 2 protein expression but this was lower than TCP. On PCL+HA aligned fibers, non-treated cells expressed Bax protein similar to TCP and reduced levels of Bcl2 protein unlike TCP. These results suggested that on PCL aligned fibers the usually aggressive BCCs had low stem cell proteins, reduced anti-apoptotic protein markers.

Treated cells by day 7 on TCP, showed increased Oct-4 protein with a reduced Sox2 production; reduced but high expression of Bax protein accompanied by an increased expression of Bcl2 protein. On PCL+HA random fibers by day 7, treated cells had low expression of Oct-4 proteins, which was accompanied by an increased expression of Sox2 production; increased Bax and Bcl2 proteins. These results inferred that on random bone scaffolds, resistant BCCs still maintained stem cell marker proteins and increased anti-apoptotic properties. On PCL+HA aligned fibers by day 7, treated cells had low expression Oct-4 expression with significantly high Sox-2 expression, increased Bax expression with increased Bcl2 expression. These results inferred that on aligned bone scaffolds, resistant BCCs expressed stem cell protein markers, increase in both anti-apoptotic and pro-apoptotic protein markers.

Additionally the relative expression levels of miRNA-222 of the MDA-MB-231 cells on the bone scaffolds relative to TCP were studied. When comparisons between PCL random and PCL aligned fibrous scaffolds (without HA) and TCP were made, non-treated cells did not have significant difference in expression of miR-222 gene between the different groups at day 1 and day 7. Treated cells showed significantly higher expression of miR-222 gene at day 1 on PCL random than treated cells on TCP and PCL aligned. At day 7, treated cells showed significantly lower expression of miR-222 on PCL random and aligned fibers than on TCP. These findings suggested that the treated cells miR-222 expression seemed to be affected by fiber orientation.

When comparisons were made between TCP and the random and aligned bone-like scaffolds, miR-222 expression of non-treated cells was significantly lower on aligned fibrous bone-like scaffolds at day 1 when compared to random fibrous bone-like scaffolds and TCP. There was no significant difference in expression between groups at day 7. These findings suggested that at an early time point, fiber alignment seems to affect the miR-222 expression of the usually aggressive BCCs but not at later time points (day 7). Moreover, treated cells had significantly higher levels of expression of miR-222 gene on random bone-like fibrous scaffolds at day 1 as compared to TCP and aligned fibrous bone-like scaffolds at day 1. At day 7, treated cells on random bone-like fibrous scaffolds had a significantly lower expression of miR-222 gene in comparison to TCP and aligned bone-like scaffolds. These findings suggested that the bone-like scaffolds affected the miR-222 gene expression behavior of the treated cells.

EXPERIMENTAL

Materials

Dulbecco's Modified Essential Medium (DMEM), penicillin, streptomyosin, Alexa Fluor 488 phalloidin and RNase A were purchased from Invitrogen (Carlsbad, Calif.). Roswell Park Memorial Institute (RPMI) 1640 was purchased from Sigma (St. Louis, Mo.). SYTO 59 Red Fluorescent Nucleic Acid stain, Restore Western Blot Stripping Buffer and NE-PER Nuclear and Cytoplasmic Extraction Kit were purchased from Thermo Scientific (Waltham, Mass.), fetal bovine serum from Hyclone (Logan, Utah), restore western blot stripping buffer and NE-PER Nuclear and Cytoplasmic Extraction Kit from Thermo Scientific (Waltham, Mass.). Poly ($\epsilon$-caprolactone) (PCL, $[(CH2)_5 COO]_n$—), having 80,000 MW, was be purchased from Sigma Aldrich, Inc. Hydroxyapatite (HA) having an average particle size of 100 nm; was be purchased from Berkeley Advanced Biomaterials, Inc. (Berkeley, Calif., USA). The solvent used for electrospinning was methylene chloride (MC) (density=1.32 g/cm$^3$, boiling point=39.75° C., dielectric constant=9.1) from Fisher Scientific, Inc.

Antibodies

The following antibodies were purchased from Abcam (Cambridge, Mass.): rabbit polyclonal anti-Oct-4, anti-bax rabbit monoclonal, rabbit polyclonal anti-Sox2, rabbit polyclonal to Cyclin D1, mouse monoclonal IgG to $\beta$-actin, mouse anti-$\beta$-actin mAb, anti-Bcl-2 antibody, FITC-polyclonal goat anti-rabbit IgG. Rabbit anti-goat IgG-Rhodamine conjugate from Millipore (Billerica, Mass.); 4'-6'-diamidino-2-phenylindole nuclear stain (DAPI) and green phalloidin were purchased from Invitrogen (Carlsbad, Calif.). Anti-human CD44-PE, and anti-human CD24-FITC were purchased from BD Biosciences (Franklin Lakes, N.J.). PE-anti-rabbit IgG was purchased from Santa Cruz Biotechnology (Santa Cruz, Calif.).

Methods

Characterization of Breast Cancer Cells
Cell Lines

MDA-MB-231 (highly invasive, basal-like) breast cancer cell lines were obtained from the American (ATCC) and cultured as described in the art and ATCC instructions. Briefly, MDA-MB-231 was cultured in DMEM containing 10% fetal bovine serum and 1% penicillin and streptomyosin, at 37° C., 5% CO2 in a humidified incubator. T47D breast cancer cell lines were cultured in RPMI 1640 supplemented with 10% FBS and 0.2 Units/ml bovine insulin. Media was replaced every 2-3 days. The cells were split at 80% confluence using 0.25% EDTA-trypsin.

Carboplatin Treatment of BCCs Before Seeding on Scaffolds

To isolate the chemoresistant BCCs from the heterogeneous non-treated population of BCCs, carboplatin sensitivity of BCCs was investigated Breast cancer stem cells (BCSCs) have been shown to resist chemotherapy thus to isolate these BCSCs from the heterogeneous non-treated population of BCCs, carboplatin sensitivity of different BCCs was investigated using the trypan blue cytotoxicity test. For determination of cell viability, treated as well as non-treated cells were used. MDA-MB-231 and T47D cells were seeded in T-175 tissue culture flasks. At 80% confluency, the growth media was replaced with fresh media containing different concentrations of carboplatin for 48 and 72 h. All experiments were repeated twice. After treatment, the culture media was collected in a 50 ml centrifugation tube, since it might contain dead cells necessary for cell counts. The cell monolayer was washed with PBS and then collected in the same tube. Cells were treated with Trypsin and, Trypsin with the cells was collected in the same 50 ml tube. The suspension was centrifuged (5 min, 1200 rpm) and the supernatant removed. The pellet was washed with PBS, centrifuged (5 min, 1200 rpm) and re-suspended again in complete culture media. Then, a small aliquot of the cell suspension (25 µl) was mixed with the same volume of 0.4% trypan blue (Sigma) solution and the sample was counted after 2 min of staining using a haemocytometer. The number of bright (viable) cells and blue cells (non-viable) were evaluated using a light microscope with a 20-fold magnification. After counting, the cell viability (CV) was expressed as the percentage of surviving cells compared to the total number of cells:

$$CV=(\text{viable cells/total number of cells})\times 100.$$

The concentrations of drugs that were finally toxic to at least 50% of the cell population (IC50/cytotoxicity) were determined. Then, studies were performed looking at viability over the full range of carboplatin concentrations and compared to non-treated BCCs. At day 3-post treatment, viable resistant BCCs were selected and counted using standard protocols for downstream experiments on scaffolds.

Random Fiber Collection

The basic principle behind this process is that an electrical voltage sufficient enough to overcome the surface tension of the polymeric solution causes the polymer droplets to elongate and eject very fine fibers, which when deposited, form non-woven mats. The electrospinning setup used for the fabrication of random fibrous scaffolds consist of a syringe pump (Cole Parmer, Vernon Hills, Ill.), a syringe containing a polymer solution, a needle attached to the syringe, a grounded collector (aluminum plate), and a high voltage power supply (Gamma high voltage, Florida).

Aligned Fiber Collection

For aligned fiber electrospinning, instead of a collecting plate, a fast foil-covered rotating drum was used for aligned fiber collection (FIG. 1). The electro spinning parameters to collect aligned fibrous scaffolds from the collector were similar to the random fiber collection. Polymer solution, needle size, voltage applied, and airflow remained unchanged for both scaffold types. The rotation of the collector was kept at high RPM of 1,000-1,300 using a Nova-Strobe series stroboscope (Monarch Instrument) since lower RPMs can result in the production of unaligned fiber mats. In order to increase the accumulation of fibers, the distance was shortened to 20 cm for the electrospinning of aligned fibers. Since the surface area is significantly larger for the rotating drum (A=cm2), 2-3 batches of solution needed to be used for each spin in order to obtain an aligned mat of relative compared to random mats.

The solution was prepared at room temperature in an airtight glass vial. Prior to adding the solvents and solutes, the vial and stirrer were rinsed with MC to ensure there is no residue present. The amount of solutes, depending on the concentration (weight/weight) and the volume of solvent were measured using the electronic balance (Ohaus Corporation, USA). The desired amount of PCL was added to the measured volume of MC to make the following: 15 wt % PCL random mats in MC and 15 wt % PCL with aligned fiber orientations. Since MC is highly volatile, an airtight cap was used to close the bottle in order to prevent the escape of MC vapors. For the PCL only mats, the solution was slowly agitated on magnetic stirrer (Corning Stirrer/Hot Plate) for at least one hour until the beads of PCL completely dissolve and the polymer solution is form. For the PCL-ceramic composite mats, ceramic powder was added to the PCL-MC mix and stirred for at least 2 hours. Next, ceramic dispersions in MC solvent were ultrasonicated for one minute to disassociate any large aggregates of ceramic. The solution was transferred to a syringe for electrospinning. The electro-spun mats were air dried for 2 days to remove any residual solvents and stored in vacuum desiccators.

Scaffold Characterization
Morphology

Electrospinning process produces ultrafine fibers, ranging from micron to nano level. The morphological characterization such as fiber distribution, fiber diameter and inter-fiber spacing can be obtained using scanning electron microscopy (SEM, LEO 1530 Gemini, Germany). Porosity was measured using the density values of the raw materials and the mat. The samples were cut from the mats using a biopsy punch (Fisher Scientific, Atlanta Ga.) to create disks having a diameter of 6 mm. They were mounted on the circular stubs using double-sided carbon tape. The specimens fixed stubs were mounted on the microscope chamber. The accelerating voltage of 2 kV and working distance of 4 mm-7 mm was used to view the images. Four SEM images were taken per sample at 500×, 1K×, and 2.5K×, and analyzed using ImageJ software (National Institutes of Health).

Porosity Determination

The porosity was determined using the density values of the raw materials (PCL, HA) and the mat. The thickness and diameter of the mat was determined to find the volume of the mat. The samples were cut from the mats using a biopsy punch to create disks having a diameter of 6 mm. The mass of the mat was determined by mass balance. The density of mat (μmat) was then calculated by taking the ratio of mass to volume. Five samples were measured from each mat to find the porosity of the mat. The porosity was calculated using the formula:

$$\text{Porosity (\%)} = (1 - \mu\text{mat}/\rho\text{raw})100 \qquad (2.1)$$

where ρraw is the density of raw material, which in turn, is calculated using the following formula:

$$\rho\text{raw} = 1/\{(\text{wt \% of ceramic}/\rho\text{ceramic}) + (\text{wt \% of PCL}/\rho PCL)\} \qquad (2.2)$$

where ρceramic is the density of the ceramic and ρPCL is the density of the PCL. The density of PCL and HA, as given by the manufacturer is 1.14 g/cm3 and 3.16 g/cm3 respectively.

Calculating Degree of Fiber Alignment

Fiber alignment was determined by forming a line perpendicular to a fiber in each SEM image at 1000× magnification (ImageJ). Five angle measurements were then taken at random between the drawn line and fiber, and their absolute deviation values (ADV) were recorded. With the ADV for each of the 16 images, the following equation was used:

$$\% \text{ Alignment} = (90° - \text{ADV})/90° * 100\% \qquad (2.3)$$

Fiber Diameter

Using biopsy punches (Miltex), 6 mm diameter disks are created per scaffold type (n=4). These samples are mounted onto the SEM stubs by using the carbon double-sided tape. To make the mounted samples conductive for SEM, the samples are then coated with gold using sputter at 40 μA for 15-20 seconds. The SEM images are taken with accelerating voltage from 3 kV to 5 kV and working distance ranging from 7-8 mm. Three samples from each mat were cut and five different regions of each sample were analyzed using SEM to calculate the fiber diameter and inter-fiber spacing. So, total 15 fiber-diameters and 15 inter-fiber spacing for each mat were calculated and the average were determined using ImageJ software (National Institutes of Health). SEM images are taken per sample at 500×, 1000×, and 2500×.

Mechanical Properties

Mechanical properties of substrates have been shown to influence cell differentiation and behavior via mechanotransduction pathways. Mechanical properties were determined by tensile testing using an Instron 3342 mechanical tester (Instron Corporation, Norwood, Mass., USA). The electro-spun scaffolds were cut into rectangular strips. The samples were immersed in deionized water for one hour and tested while wet at room temperature. The samples had a gauge length of 30 mm and a width of 12 mm. The thickness of the sample was measured using Vernier calipers at five positions, which fell within the gauge length, and the average value 0.12±0.02 mm was used for plotting the stress strain curve. The crosshead speed was 50 mm/minute. Five specimens were tested and their average plotted. The Young's modulus, yield stress, and maximum tensile stress were obtained from the stress-strain diagrams.

Fourier Transform Infrared Spectroscopy

Fourier transform infrared spectroscopy (FTIR) was used to determine the presence of the HA and overall surface chemistry of the scaffold. FTIR is performed using the Perkin Elmer FTIR-ATR 100 series for all scaffolds. The spectra in the range of 4000-400 cm-1 with a resolution of 4 cm-1 and 50 scans were collected.

Calcium Ions Assay

To analyze ion release from our scaffolds, a calcium assay was performed. Scaffolds of pure PCL and PCL containing ceramic were immersed in PBS and analyzed at days 1, 4 and 7 for calcium ions using QuantiChrom colorimetric Calcium assay kit (Bioassay Systems) as per manufacturer's instructions (Bioassay Systems). Briefly, calcium standards were prepared in duplicates with known calcium concentrations in the same solution used during the study. Solution from samples were collected and incubated with a phenolsulphonephthalein dye, which formed stable blue colored complex specifically with free calcium in the sample. Absorbance was read at 612 nm on a plate reader to determine calcium ion concentration per time point. The intensity of the color measured is directly proportional to the calcium concentration in the samples.

Phosphate Ions Assay

In addition to measuring calcium ions being released from PCL+HA scaffolds, we also measured phosphate ions being released from scaffolds over time to identify the presence of inorganic phosphate in solution using a colorimetric phosphate assay kit (abcam) as per manufacturer's instructions. Briefly, scaffolds of pure PCL and PCL containing ceramic, were immersed in PBS and analyzed at days 1, 4 and 7. The assay utilizes a proprietary formulation of malachite green and ammonium molybdate, which forms a chromogenic complex with phosphate ion giving an intense absorption, band around 650 nm. Phosphate standards of known phosphate concentrations were prepared in duplicates. Standards and sample solutions were incubated with phosphate reagent at room temperature for 30 minutes. Next, the absorbance at 650 nm read using a plate reader.

BCCs Culture on Scaffolds

For all experiments, the electro-spun were cut into 6 mm diameter discs. The samples were sterilized by immersing in 100% ethanol for 25 minutes and air-dried under sterile conditions over night. The scaffolds were then transferred to 96 well polypropylene non-adherent tissue culture plates (BD Biosciences, San Jose, Calif.) for cell seeding. Carboplatin treated BCCs and non-treated BCCs were seeded onto scaffolds at 31 cells/mm$^2$ to obtain single cells on the scaffolds. The seeded BCCs were analyzed for attachment, proliferation, viability, migration and cyclin D1 expression. Comparisons were made with cells cultured on standard tissue culture treated polystyrene plates (TCP). The medium was changed at each time point and treated cells were supplemented with fresh medium containing carboplatin.

Cell Morphology

BCCs on scaffolds were evaluated for cell morphology at days 1, 4 and 7. Cells on the scaffolds were washed with 1×PBS, fixed with 4% formaldehyde for 20 min and then permeabilized with 0.1% Triton X-100 in PBS. The cells were labeled with DAPI for nuclear identification and Alexa Fluor 488 phalloidin for actin filaments. After 1, 4 and 7 days, the cells were assessed for morphology by confocal microscopy (Clsi, Nikon, Japan).

Cell Proliferation

Cell growth was assessed on days 1, 4, and 7. The lysates were used to quantify cell number using the PicoGreen dsDNA assay (Invitrogen Corp., Carlsbad, Calif.) in which cell number can be correlated to fluorescence intensity. PicoGreen dsDNA reagent is an ultrasensitive fluorescent nucleic acid stain for quantifying double-stranded DNA in solution. BCCs of known cell number served as standards.

Standards and samples (n=4 per group per time-point) were prepared by lysing cells with 0.1% Triton X-100. Fluorescence was detected with a microplate reader (FLX800, Biotek, Winooski, Vt.) at 480 nm excitation/520 nm emission.

Cell Viability

The metabolic activity of the cells was determined on days 1, 4, and 7. Viability was assessed in cell cultures using the CellTiter-Glo Cell Viability Assay (Promega) as per manufacturer's protocol.

Immunocytochemistry

The expression of Cyclin D-1 in BCCs plated on the scaffolds was performed at days 1, 4, and 7 by confocal microscopy. Samples were washed with 1×PBS, fixed with 4% formaldehyde (10 min) and then permeabilized by incubating in 1% BSA/10% normal goat serum/0.3 M glycine in 0.1% PBS-Tween for 1 h. The serum blocked the interaction between the antibody and non-specific proteins. The cells were then incubated overnight at 4° C. with the anti-cyclin D1 (1/1000). The cells were incubated for 1 h at room temperature with a secondary (red) rabbit anti-goat IgG-Rhodamine conjugate at 1/250 dilution. The cells were counterstained for nuclear identification (blue) with DAPI, and F-actin using green phalloidin.

Cell Cycle Analyses

Cell cycle analyses cells were performed with $1\times10^4$ BCCs. Samples were washed with 1×PBS and cells were detached from scaffolds using 0.25% EDTA-trypsin and neutralized with standard growth media. Cells were washed in PBS, fixed with 3.7% formaldehyde for 20 min and then re-suspended in 0.1% hypotonic sodium citrate solution containing 50 μg/ml propidium iodide and 200 m/ml DNase-free RNase A. Cells were incubated for 30 min at room temperature and then immediately analyzed on FACSCalibur (BD, San Jose, Calif.). Flow cytometric analyses data were analyzed with BD CellQuest software. After obtaining the results for cell growth/viability on the scaffolds, only the non-treated BCCs were evaluated for cell cycle analysis.

Breast Cancer Cell Migration

To investigate migratory properties of BC cells, time-lapse video microscopy was performed. Scaffolds were placed into a 96 well plate and immobilized using small Teflon rings. Then BCCs were seeded in cell culture medium onto each substrate. After 3 h, when all cells were firmly attached to the surface, the 96-well plate was mounted into the pre-heated life cell chamber (37° C. and 5% $CO_2$) of a Leica AF6000 LX widefield microscope and imaged at 10× air objective. Thereafter, images were recorded every 7 min for a total period of 6 h. Images were imported into Image J, and a time-lapse movie was assembled and cells were tracked using the plugin "particle tracker".

Western Analyses of Proteins

Western blot was performed to detect the following proteins: Bax, Bcl-2, Oct-4 and Sox-2 for BCCs on scaffolds. Briefly, whole cell extracts were prepared with the NP-40 buffer and nuclear/cytoplasmic extracts with NE-PER Nuclear and Cytoplasmic Extraction kit. BCC extracts (20 μg) were subjected to electrophoresis on 4-20% SDS-PAGE (Bio-Rad; Hercules, Calif.). Proteins were transferred to PVDF membranes, and membranes were incubated overnight in the respective primary antibodies. This was followed by 2 h incubation with HRP-conjugated secondary antibodies at 1:2000 final dilutions. The latter was detected with chemiluminescence. Membranes were stripped with Restore Western Blot Stripping Buffer and then re-probed for other proteins, including β-actin mAb (1:4000 dilution). All bands were normalized to β-actin.

Real-Time PCR Expression

RNA extraction was performed via RNeasy Mini Kit from (Qiagen, Valencia, Calif.). Quality and concentration of RNA were determined with the Nanodrop ND-1000 spectrophotometer. Total RNA (1 μg) was immediately converted from RNA to cDNA using the High-Capacity cDNA Reverse Transcription Kit (Life Technologies, Grand Island, N.Y.). Real-time PCR was performed with 10 ng of cDNA using Power SYBR® Green PCR Master Mix (Life Technologies, Grand Island, N.Y.). Incubation conditions were, 25° C. for 5 min, 50° C. for 60 min, and 70° C. for 15 min. Next results were analyzed on the 7300 Real-Time PCR System (Applied Biosystems, Foster City, Calif.). The analyses were performed with an initial incubation of 50° C. for 2 min followed by 95° C. for 2 min. After this, the cycling conditions were as follows: 94° C. for 15 sec and 60° C. for 45 sec, for 40 cycles. Gene expression for Cyclin D1, Oct-4, β-actin, Bcl2, Sox3 and MDR1 were determined.

mRNA Real-Time PCR

RNA extraction was performed according to manufacturer's protocols with the RNeasy Mini Kit (Qiagen, Valencia, Calif.). Quality and concentration of RNA were determined with the Nanodrop ND-1000 spectrophotometer. The High-Capacity cDNA Reverse Transcription Kit (Life Technologies, Grand Island, N.Y.) was used to convert RNA to cDNA. Real-time PCR was performed with 10 ng of cDNA using either Taqman Universal PCR Master Mix II or Power SYBR® Green PCR Master Mix (Life Technologies, Grand Island, N.Y.).

miRNA Real-Time PCR

RNA extraction was performed using the miRCURY RNA isolation Kit from Exiqon (Woburn, Mass.). TaqMan® Small RNA Assays were performed with 10 ng of RNA, which was reversed transcribed immediately after isolation with the TaqMan MicroRNA Reverse Transcription Kit (Applied Biosystems, Foster City, Calif.) and a reverse primer specific for the miRNA-222 primary transcript. The incubation conditions were, 16° C. for 30 min, 42° C. for 30 min, and 85° C. for 5 min. Real-time PCR was performed with 2 ng cDNA using TaqMan Universal PCR Master Mix 2× No AmpErase UNG (Invitrogen) and primers for the miRNAs: hsa-miR-222 and TaqMan® Small RNA Control RNU6 used as a reference for TaqMan assay data normalization. All primers were purchased from Life Technologies. TaqMan primers were purchased from Life Technologies, other primer sequences are in Table 1. The reverse primer used for PCR was identical to the primer used for transcription and paired with a forward primer specific for miRNA-221/222. Next results were analyzed on the 7300 Real-Time PCR System (Applied Biosystems, Foster City, Calif.). For all the qRT-PCR experiments, values on the y-axis equal to $2^{-D\,(Dct)}$, where DCt is the difference between gene Ct and normalizer gene Ct. Ct represents the threshold cycle at which fluorescence rises statistically significantly above the baseline.

Statistical Analyses

All assays will be performed with an n=4 per group per time point for each data point. Studies will be repeated to establish reproducibility of the data. Results in graphs will be presented as mean±standard deviation. Results will be analyzed using a one-way ANOVA and a posthoc Tukey test. Statistically significant values were defined for p<0.05. All statistical analyses were performed using SPSS Statistics software.

Results

Scaffold Fabrication

Four different scaffolds were successfully constructed varying in fiber orientation as well as composition as shown in FIG. 1. A 15% wt PCL in MC solution yielded two scaffold types—random and aligned fibrous mats.

Random and aligned fiber scaffolds were also constructed from PCL composite materials obtained from solutions of 10% wt polymer PCL in MC combined with 30% wt ceramics of HA. SEM imaging at 500×, 1000×, and 2500× revealed the fibrous micro and nanostructures for each scaffold configuration and type (FIG. 1).

Scaffold Characterization

PCL and PCL+HA random fibers had fiber diameter of 9.5±2.2 μm and 9.1±3.2 μm respectively; while aligned PCL and PCL+HA aligned fibrous scaffolds had fiber diameters of 8.9±2.1 μm and 9.9±2.9 μm respectively. PCL random fibers had porosity of 86±1.6%; PCL+HA random fibers had porosity of 79±1.5%, and PCL aligned fibers had porosity of 76.8±2.9% and PCL+HA aligned 6.5±1.1%. Moreover, PCL random fibers had, an average elastic modulus of 4.4 MPa (±1.02) and an average ultimate tensile stress of 1.1 MPa (±0.14). PCL+HA random fibers had an average elastic modulus of 5.4 MPa (±1.5) and an average ultimate tensile stress of 0.6 MPa (±0.1). PCL aligned fibers had an average elastic modulus of 5.07 MPa (±0.84), and an average ultimate tensile stress of 0.79 MPa (±0.13). PCL+HA aligned had an average elastic modulus of 7.4±2.3 MPa and an average ultimate tensile strength of 0.52±0.34 MPa. There was no significant difference in fiber diameter between all mats suggesting that these different scaffolds were similar in fiber sizes. There was a significant difference in interfiber spacing between aligned fibers and random fibers ($p<0.05$), which was expected since the aligned oriented fibers were more densely packed than the random non-woven fibers. The fibrous constructs produced by the electrospinning process had a high surface area-to-volume ratio, which provided more surface and volume for BCCs attachment as compared to TCP. There was a significant difference in porosity between random fibers and aligned fibers ($p<0.05$) which was also expected since non-woven fibers as mentioned earlier, were loosely packed as compared to aligned oriented fibers. There was no significant difference in modulus between the different scaffold groups.

PCL+ ceramic scaffolds had significantly lower UTS but the moduli of all mats were within the range of native bone (2-5 MPa). These results suggest that the addition of the ceramic did not reduce the stiffness of our scaffolds. Random fibers had an average thickness of 0.36 mm (±0.02), while aligned fibers had an average thickness of 0.3 mm (±0.03).

TABLE 2.1

Fiber Diameter and Interfiber Spacing of Electrospun Scaffolds.

| Type of Scaffold | $D_r$ (μm) | Inter-fiber Spacing (μm) | Alignment (%) |
|---|---|---|---|
| PCL random | 9.5 ± 2.2 | 86 ± 16 | N/A |
| PCL + HA random | 9.1 ± 3.2 | 79 ± 15 | N/A |
| PCL aligned | 8.9 ± 2.1 | *8.4 ± 1.7 | 95.4 ± 4.8 |
| PCL + HA aligned | 10 ± 2.9 | *6.5 ± 1.1 | 96 ± 3.3 |

*Interfiber Spacing difference between aligned fibers and random fibers ($p < 0.05$)

TABLE 2.2

Porosity and Tensile Properties of Electrospun Scaffolds. Porosity difference between PCL aligned fibers remaining two scaffolds.

| Type of Scaffold | Porosity (%) | Modulus (MPa) | Ultimate Tensile Stress (MPa) |
|---|---|---|---|
| PCL random | 86 ± 16 | 4.4 ± 1.0 | 1.1 ± 0.1 |
| PCL + HA random | 79 ± 15 | 5.4 ± 1.5 | **0.6 ± 0.1 |
| PCL aligned | *8.4 ± 1.7 | 5.1 ± 0.8 | 0.8 ± 0.1 |
| PCL + HA aligned | *6.5 ± 1.1 | 7.4 ± 2.3 | **0.52 ± 0.34 |

**Ultimate Tensile Strength difference between composite and polymer alone ($p < 0.05$)

Fourier Transform Infrared Spectroscopy

FTIR analysis was used to determine the surface chemistry for the scaffolds. In this study, the spectrum for PCL and PCL composite scaffolds were obtained. FTIR spectrum was obtained for all of scaffolds immersed in DI water at day 0, and 7. The carbonyl group (in PCL) and phosphate group (in HA) absorbed the IR at particular frequency, which matched with the frequency of the vibrating atoms. The peaks corresponding to carbonyl of PCL were observed at 1721 cm-1 and 1163 cm-1 in all the scaffolds. The phosphate peaks were observed at 1036 cm-1 and 562 cm-1, in case of composite scaffolds.

The results showed that there was presence of apatite in the composite scaffolds at both time points, whereas there is no apatite deposition in case of pure PCL scaffolds, since there is no ceramic.

Calcium Dissolution

Release of calcium ions from the scaffolds to the solution was measured. Results indicated that there was no significant difference in release from pure PCL scaffolds and PCL+HA scaffolds suggesting that PCL+HA scaffolds were not releasing calcium ions into the solution during the 7-day cell culture period.

Phosphate Dissolution

Similar to the calcium release findings, phosphate assay results showed that there was no significant difference in phosphate release between pure PCL scaffolds and PCL+HA scaffolds. This also suggested that phosphate might not have been released into solution during the 7-day culture period. These results also show that the scaffolds were stable. The results from the calcium ions and phosphate ions together showed that these fabricated scaffolds were stable over the 7-day culture period.

Carboplatin Survival Curves

Carboplatin cytotoxicity was assessed after exposure to concentrations ranging from 0 to 50 μg/ml for 72 hours. At 2 days post treatment, all cell lines displayed sensitivity to carboplatin: 28% death ($IC_{50}$=105.38 μM) for T47D cells and 17% death for MDA-MB-231 cells ($IC_{50}$=182.1 μM) at a maximum carboplatin concentration of 50 μg/ml (FIG. 4.A).

Figure 4:
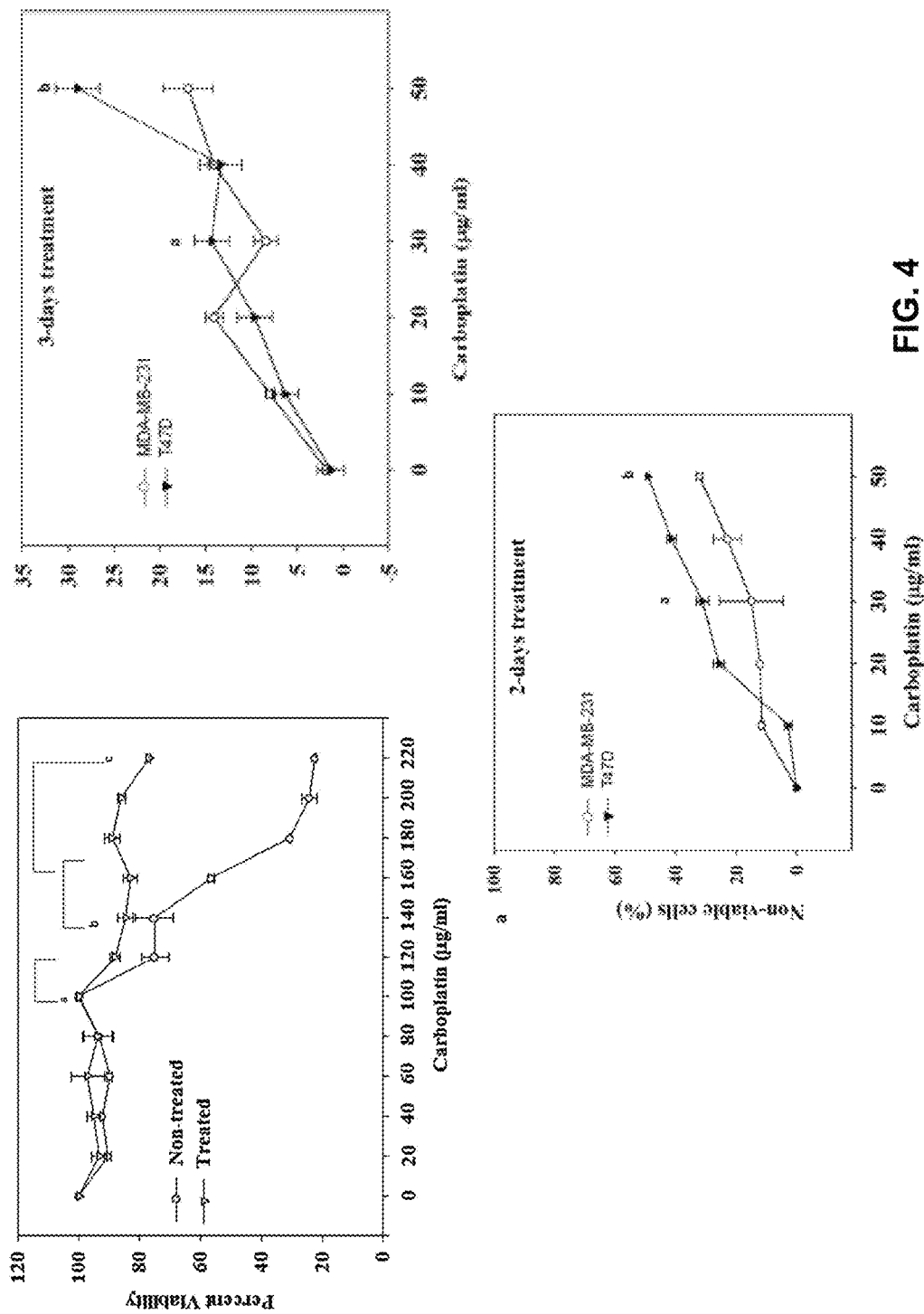
FIG. 4 shows the effect of carboplatin treatment on the viability of breast cancer cell lines a) Percentage of non-viable cells at 2 days post treatment with carboplatin. The results are shown as the mean±SD, n=7 of non-viable cells. $^a$ $p<0.05$, significant increase in non-viable BCCs at 30 µg/ml as compared to 0 µg/ml. $^b$ $p<0.05$, significant increase in non-viable BCCs at 50 µg/ml as compared to 0 µg/ml and 30 µg/ml. b) Percentage of non-viable cells 3 days post treatment. $^a$ $p<0.05$, significant increase in non-viable BCCs at 30 µg/ml as compared to 0 µg/ml. $^b$ $p<0.05$, significant increase in non-viable BCCs at 50 µg/ml as compared to 0 µg/ml and 30 µg/ml. c) Carboplatin survival curve for chemotherapy treated and non-treated MDA-MB-231 cells. $^a$ $p<0.05$, significant decrease in percent viability (30%) of non-treated cells treated with carboplatin dosages between 100 µg/ml to 120 µg/ml as compared to treated cells (10%). $^b$ $p<0.05$, significant decrease in percent viability (40%) of non-treated cells treated with carboplatin dosages between 140 µg/ml to 170 µg/ml as compared to treated cells (20%). $^c$ $p<0.05$, significant decrease in percent viability (80%) of non-treated cells treated with carboplatin dosages 170 µg/ml to 220 µg/ml as compared to treated cells (20%).

At 3 days post treatment, the maximum dosage of 50 μg/ml carboplatin concentration showed an increased sensitivity in T47D cells with 48% death ($IC_{50}$=48.9 μM) (FIG. 4.B). MDA-MB-231 cells had only 25% death ($IC_{50}$=86 μM) 3 days post treatment.

Furthermore, in order to demonstrate chemo-resistant (treated) BCCs remain viable even with additional carboplatin treatment, different concentrations of carboplatin were used on both non-treated and chemoresistant (treated) BCCs. Comparisons between non-treated and treated MDA-MB-231 showed no significant difference in percent viability between 0 and 100 □g/ml carboplatin treatment. However, with higher carboplatin dosages, non-treated cells showed a significant decrease in percent viability ($p<0.05$): 30% decrease between 100 □g/ml to 120 □g/ml carboplatin treatment as compared to treated cells (10%), 40% decrease between 140 □g/ml to 170 ug/ml carboplatin treatment as compared to treated cells (20%); 80% decrease between 170 □g/ml to 220 □g/ml carboplatin treatment as compared to treated cells (20%). Thus, chemo-treated BCCs had a percent viability of 80% plateauing at a high concentration of 220 □g/ml; unlike non-treated BCCs, which had a significant decrease in percent viability (20%) at this same concentration ($p<0.05$). (FIG. 4.C).

These results suggest that all cell lines displayed sensitivity to carboplatin at 2-days and 3-days post treatments with the MDA-MB-231 cells having the least amount of cell death at the highest dosage for both 2- and 3-days post treatments. Additionally, carboplatin optimization for MDA-MB-231 cells indicated that even at a maximum carboplatin concentration of 220 μg/ml, these treated cells maintained higher percent viability of 80% as compared to 20% percent viability for the non-treated cells. Thus these treated BCCs were considered the most resistant population.

Western Analyses

Carboplatin cell death can occur through an apoptotic pathway. Consequently, inhibition of this pathway by oncogenes genes such as Bcl-2 can lead to drug resistance. The bcl-2 oncogene has been shown to have an anti-apoptotic function and may play a role in tumorigenesis by raising the threshold for apoptosis.

Figure 5:
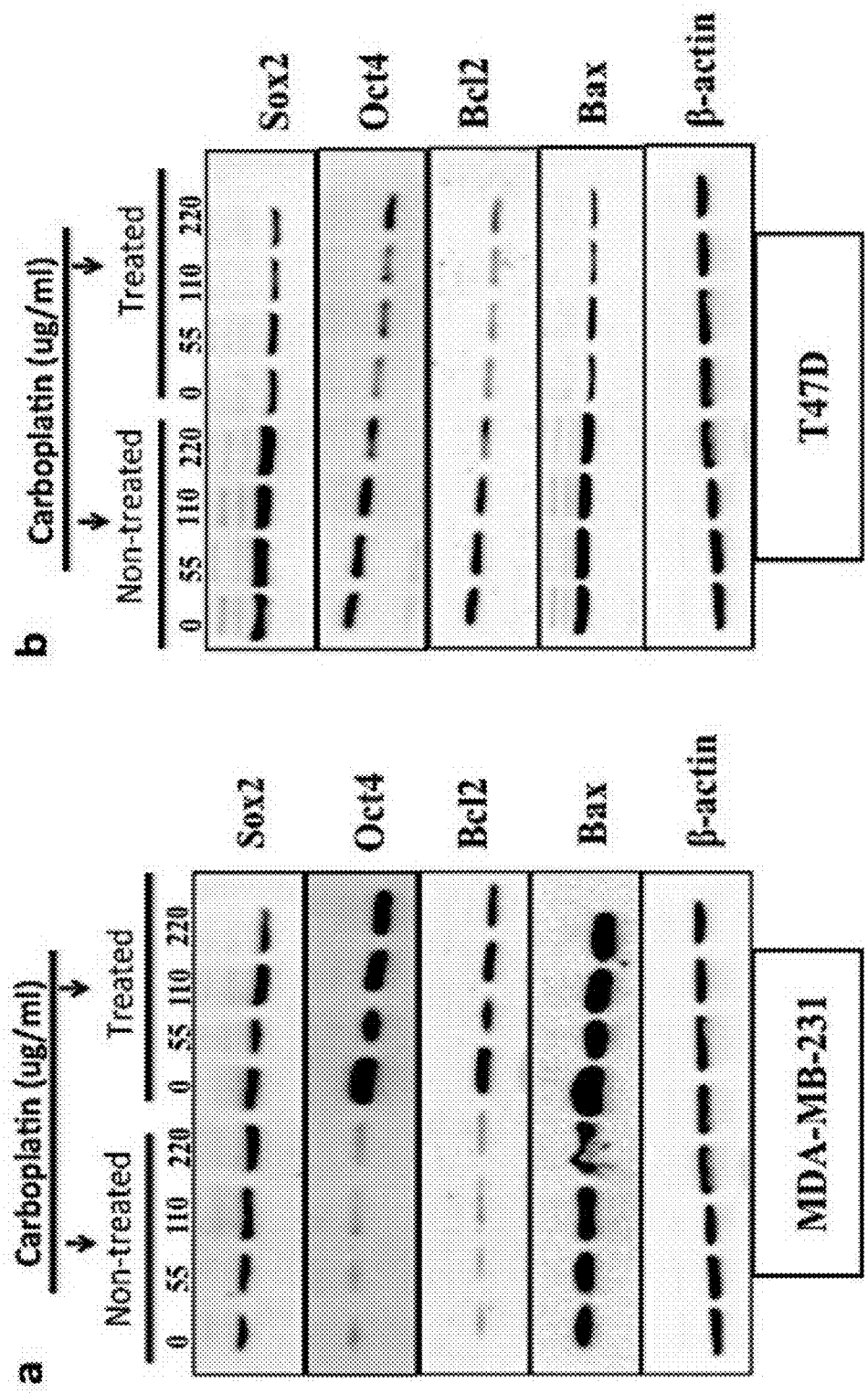
FIG. 5 shows Western blots of breast cancer cell lines with chemotherapy treatment. Bax, Bcl-2, Oct-4, and Sox2 expression was determined for A) MDA-MB-231 cells and B) T47D cells. Densitometric bands normalized to Beta actin have been provided in FIG. 2.3.
Figure 6:
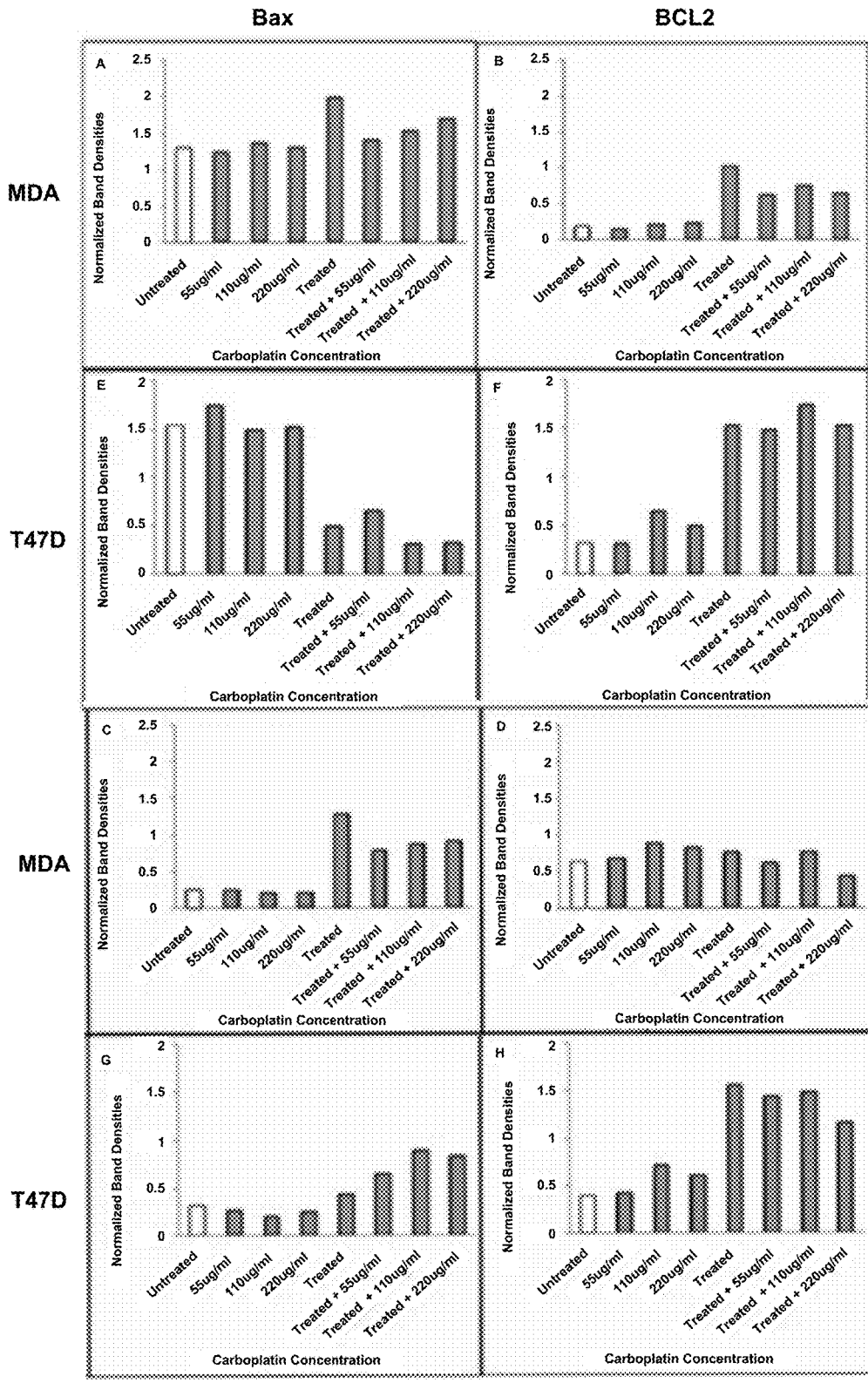
FIG. 6 shows Densitometric bands of Bax, Bcl2, Oct-4, and Sox2 expression of BCC treated with increasing dosage of carboplatin. Bands have been normalized to beta actin. A) Apoptosis related proteins for MDA: a) Bax and b) Bcl-2 and T47D: e) Bax and f) Bcl-2. B) Self-renewal related proteins for MDA: c) Oct-4 and d) Sox2 and T47D: g) Oct-4 and h) Sox

It has been well established that decreased levels of Bax are correlated to increased levels of Bcl-2. High expression levels of the Bcl2 gene have been associated with drug resistance of the cancer cells. Additionally, alongside being chemoresistant, BCCs have been recognized to express genes such as Oct-4 and Sox2, which are linked to pluripotency. Western blots results showed band intensities predicted bands for Sox2, Oct-4, Bcl-2, Bax, respectively for MDA-MB-231 and T47D cells (FIG. 5A, 5.B, 6.A., 6B.). Overall results by western analysis showed increased Bcl-2, Oct-4 and Sox2 expression with increased carboplatin concentration, which demonstrates that these resistant breast cancer cells have characteristics of cancer stem cell behavior.

CD44/CD24 Expression

Figure 7:
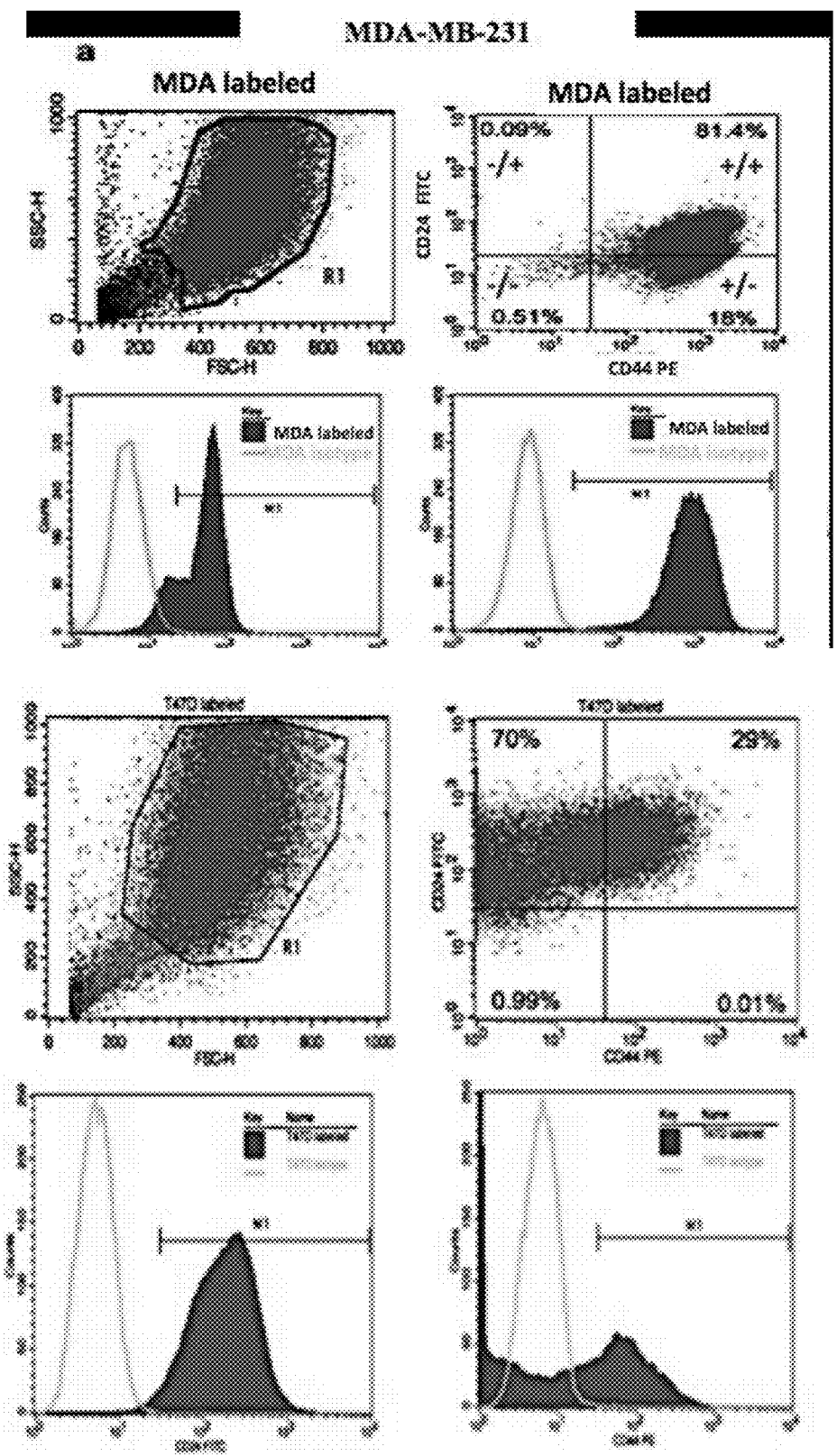
FIG. 7 shows Flow cytometry analysis of CD44/CD24 expression of A) Top left: suspension of MDA-MB-231 treated cells analyzed based on size with forward-scattered light (FSC) and side-scattered light (SSC). Top right: R1 population further analyzed by specifically gating for CD44/CD24 expressing cells. Bottom left: histogram of MDA isotype control and CD24-FITC with histogram marker M1 designating CD24-FITC positive events. Bottom right: histogram of MDA isotype control and CD44-PE with histogram marker M1, designating CD44-PE positive events. B) Top left: suspension of T47D treated cells analyzed based on size with FSC and SSC. Top right: R1 population further analyzed by specifically gating for CD44/CD24 expressing cells. Bottom left: histogram of T47D isotype control and CD24-FITC with histogram marker M1 designating CD24-FITC positive events. Bottom right: histogram of T47D isotype control and CD44-PE with histogram marker M1, designating CD44-PE positive events.

On tissue culture polystyrene, carboplatin treatment of BCCs will kill the fast dividing proliferative cells and BCSCs that have differentiated into proliferative progenitors [3]. BCSCs have already been characterized to be quiescent (G0-G1 cell cycle arrest) without the effect of carboplatin [3, 7]. Moreover, CD44/CD24 has been widely used to isolate BCSCs [16]. The flow cytometry results showed that within the MDA-MB-231 treated cells: 0.09% were $CD44^-/CD24^+$; 81.4% were $CD44^+/CD24^+$; 0.51% were $CD44^-/CD24^-$ and 18% were $CD44^+/CD24^-$ (FIG. 7A top right). Treated T47D cells were: 70% $CD44^{-/low}/CD24^+$; 29% $CD44^+/CD24^+$; 0.99% $CD44^-/CD24^-$; 0.01% $CD44^+/CD24^-$ (FIG. 7B top right). Histograms of MDA isotype control with CD24-FITC (FIG. 7.A bottom left) and CD44-PE (FIG. 7.A bottom right) depicted CD24-FITC positive events and CD44-PE positive events. Similarly, histograms of T47D isotype control with CD24-FITC (FIG. 7.B bottom left) and CD44-PE (FIG. 7*b* bottom right) showed CD24-FITC positive events and CD44-PE positive events.

The results suggested that the treated BCC population of cells was highly enriched with cells expressing CD44/CD24 markers. Thus along with the western results, these results indicated that by treating the heterogeneous BCC population of cells, we were selecting the resistant and breast cancer stem-like cells to seed on the scaffolds.

BCCs Interactions with 3-D Scaffolds

Morphology and interaction between cells and scaffold fibers were analyzed in vitro for 7 days for both MDA-MB-231 cells and T47D cells. Both chemo-resistant (treated) and non-treated MDA-MB-231 cells were adherent to the scaffolds.

Figure 8:
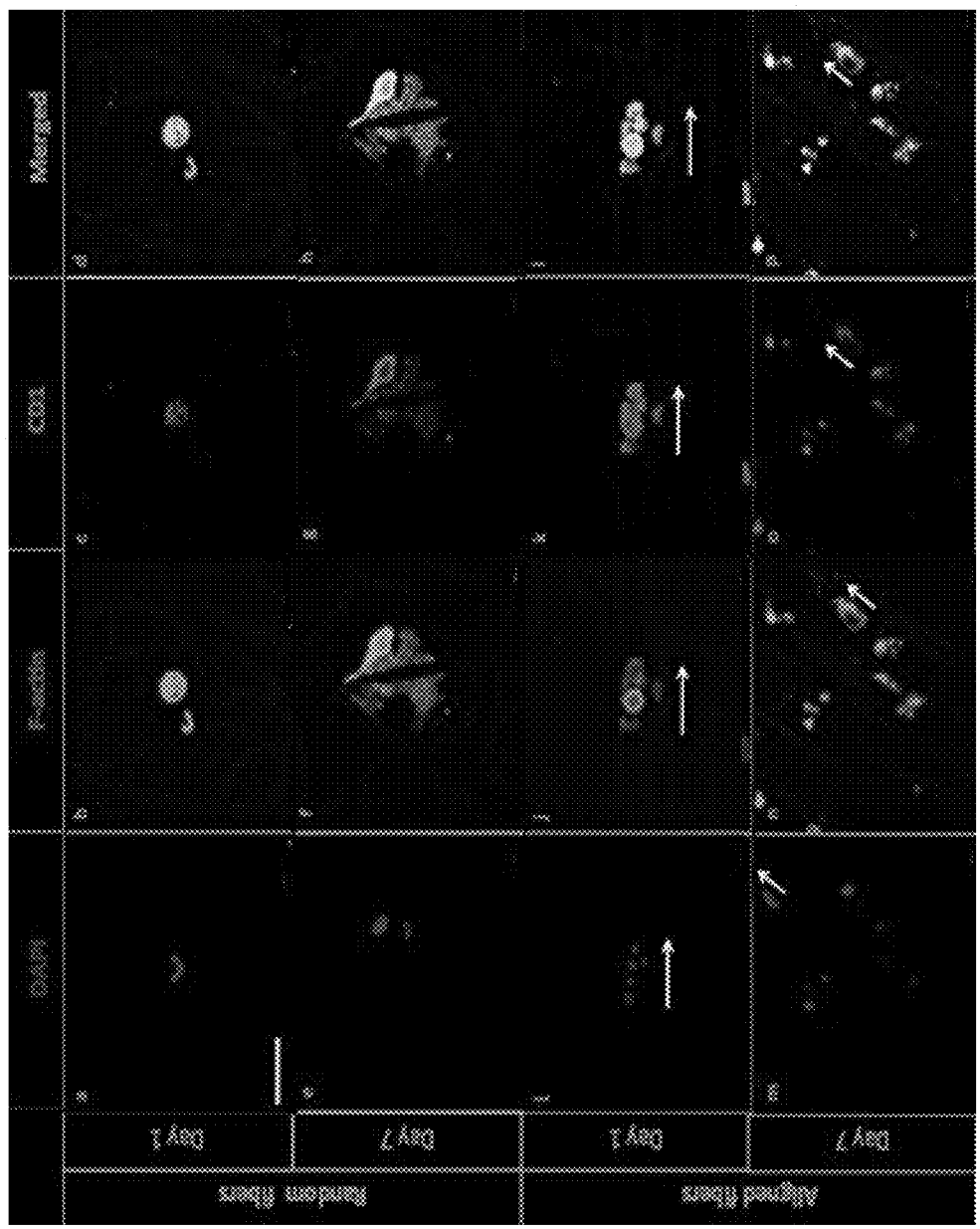
FIG. 8 shows Confocal fluorescent microscope images of non-treated MDA-MB-231 BCCs on the PCL random and aligned fibrous scaffolds. Blue indicates nuclei (DAPI); green indicates F-actin (Alexa Fluor 488 phalloidin herein after Alexa 488) and red is for anti-cyclin D1 expression. On random scaffolds (a through d—at day 1; e through h—at day 7), and aligned scaffolds (i through l—at day 1; m through p—at day 7). 60× objective. Scale bar is 25 µm. The arrows show the cell body orientation along the fibers. Studies were repeated 3 times, n=2.

Non-treated MDA-MB-231 cells had a round morphology at day 1 on both random and aligned fibers and at day 7, non-treated MDA-MB-23 cells appeared to be more spread or elongated on both fiber configurations (FIG. 8).

Figure 9:
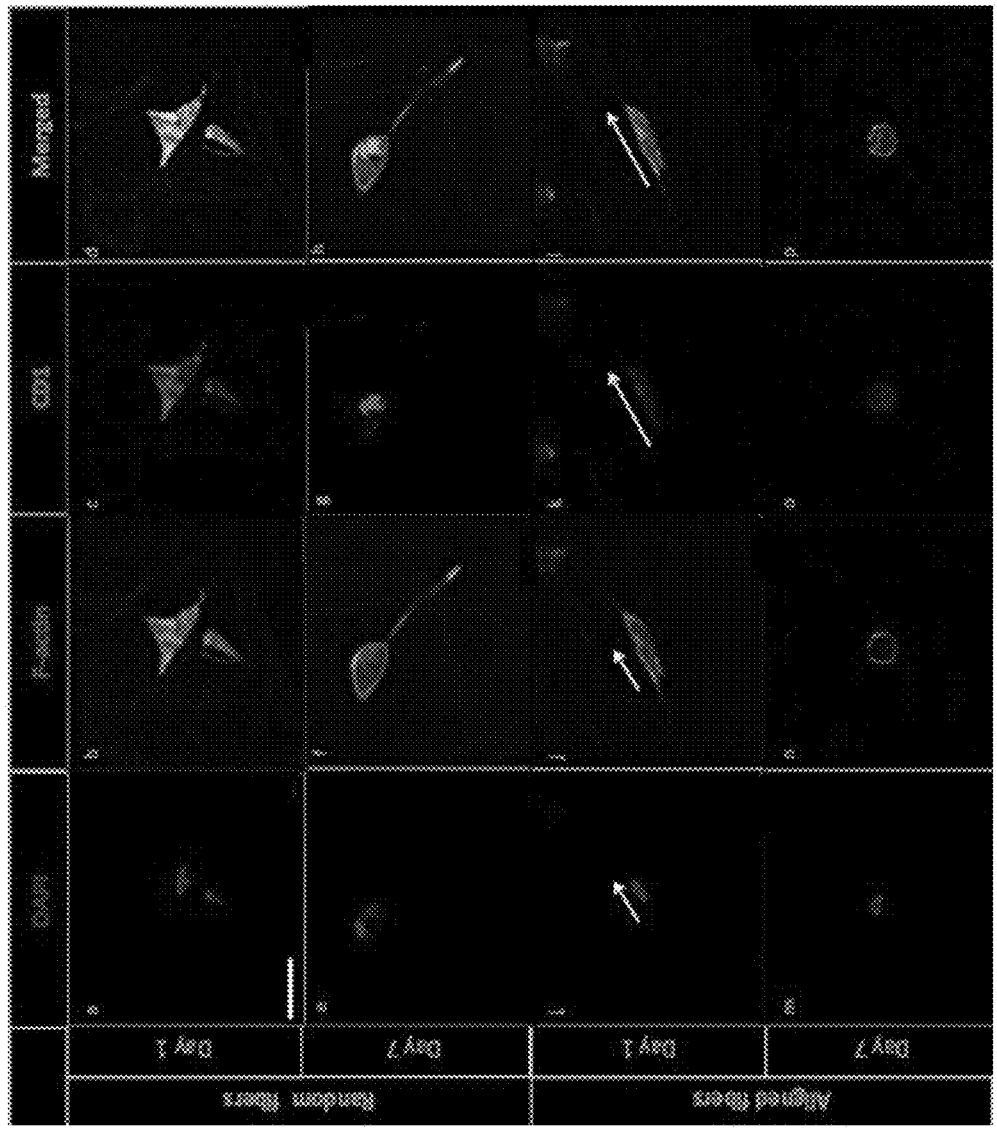
FIG. 9 shows Confocal fluorescent microscope images of treated MDA-MB-231 BCCs on the PCL random and aligned fibrous scaffolds. Blue indicates nuclei (DAPI); green indicates F-actin (Alexa 488) and red is for anti-cyclin D1 expression. On random scaffolds (a through d at day 1; e through h at day 7) and aligned scaffolds (i through l at day 1; m through p at day 7). 60× objective. Scale bar is 25 µm. The arrows show the cell body orientation along the fibers. Studies were repeated 3 times, n=2.
Figure 10:
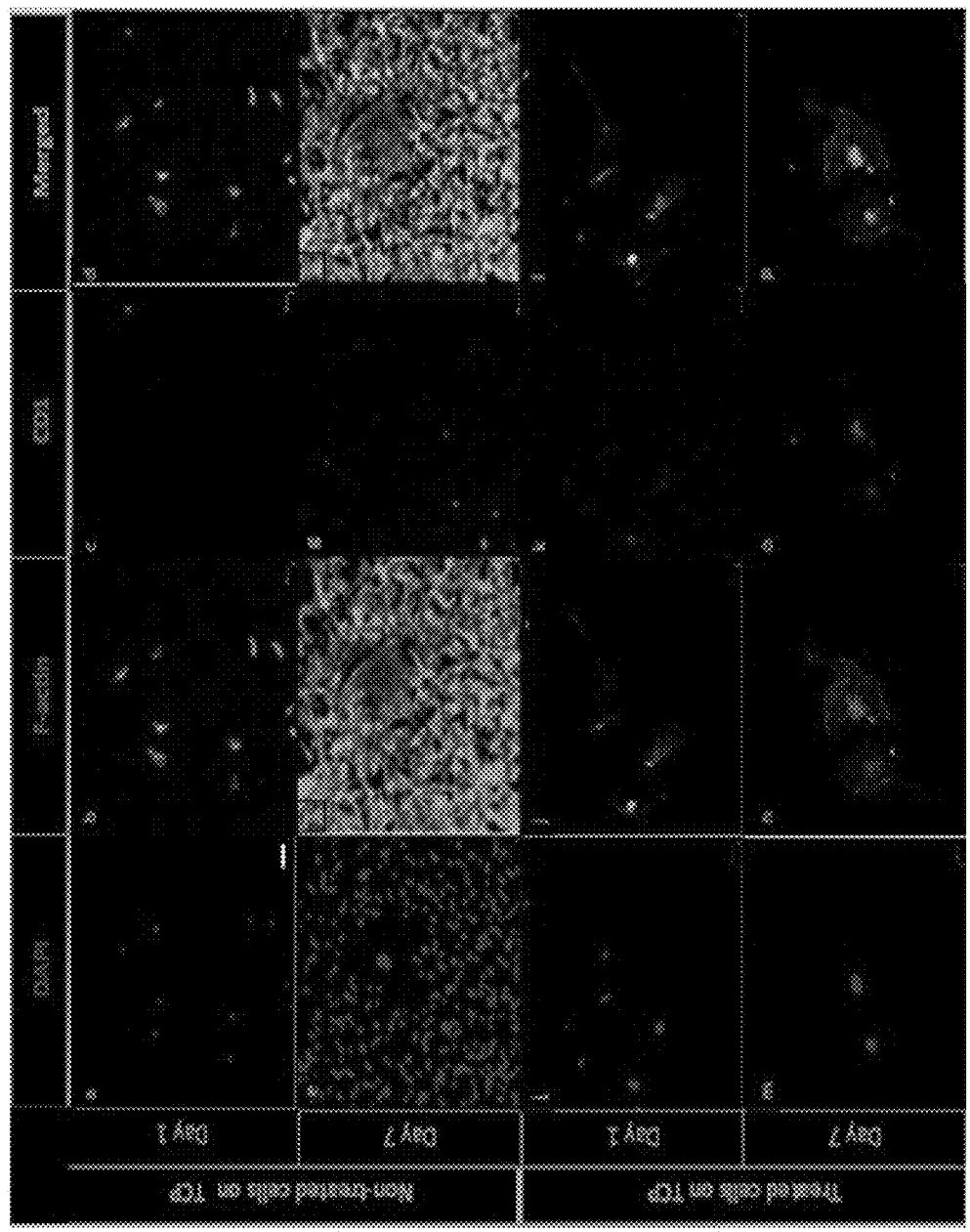
FIG. 10 shows Confocal fluorescent microscope images of MDA-MB-231 BCCs on the TCP control. Blue indicates nuclei (DAPI); green indicates F-actin (Alexa 488) and red is for anti-cyclin D1 expression. Non-treated BCCs (a through d at day 1; e through h at day 7) and treated BCCs (i through l at day 1; m through p at day 7). 60× objective. Scale bar is 25 µm. Studies were repeated 3 times, n=2.
Figure 11:
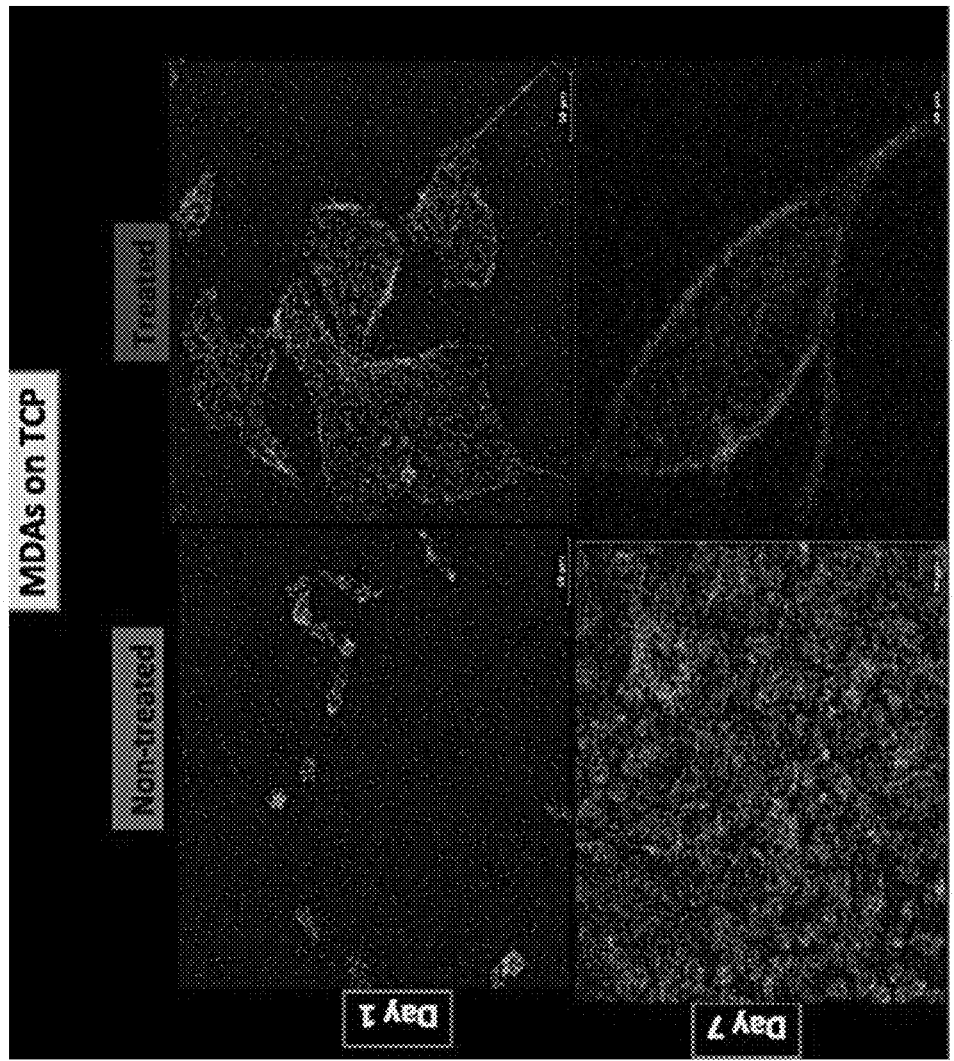
FIG. 11 shows Confocal fluorescent microscope images of MDA-MB-231 BCCs on the TCP control. Green indicates F-actin (Alexa 488) with non-treated cells at a) day 1 and b) day 7, and treated cells at e) day 1 and f) day 7. 60× objective. Scale bar is 25 µm.

For MDA-MB-231 treated cells at day 1, their morphology was spread on aligned fibers, with cell bodies along the fibers (FIG. 9) but varied for cells on random fibers where some cells also appeared rounded (FIG. 9, 10). By day 7, treated MDA-MB-231 cells appeared to have a more rounded morphology on random fibers but the morphology varied on aligned fibers where some cells appeared elongated along the fibers (FIGS. 10 and 11). On TCP, non-treated MDA-MB-231 cells displayed confluency by day 7 with some cells characterized with spread and spindle-like shapes. For treated MDA-MB-231 cells on TCP, cells appeared to be well attached to the substrate with a spread morphology (FIG. 11).

Figure 12:
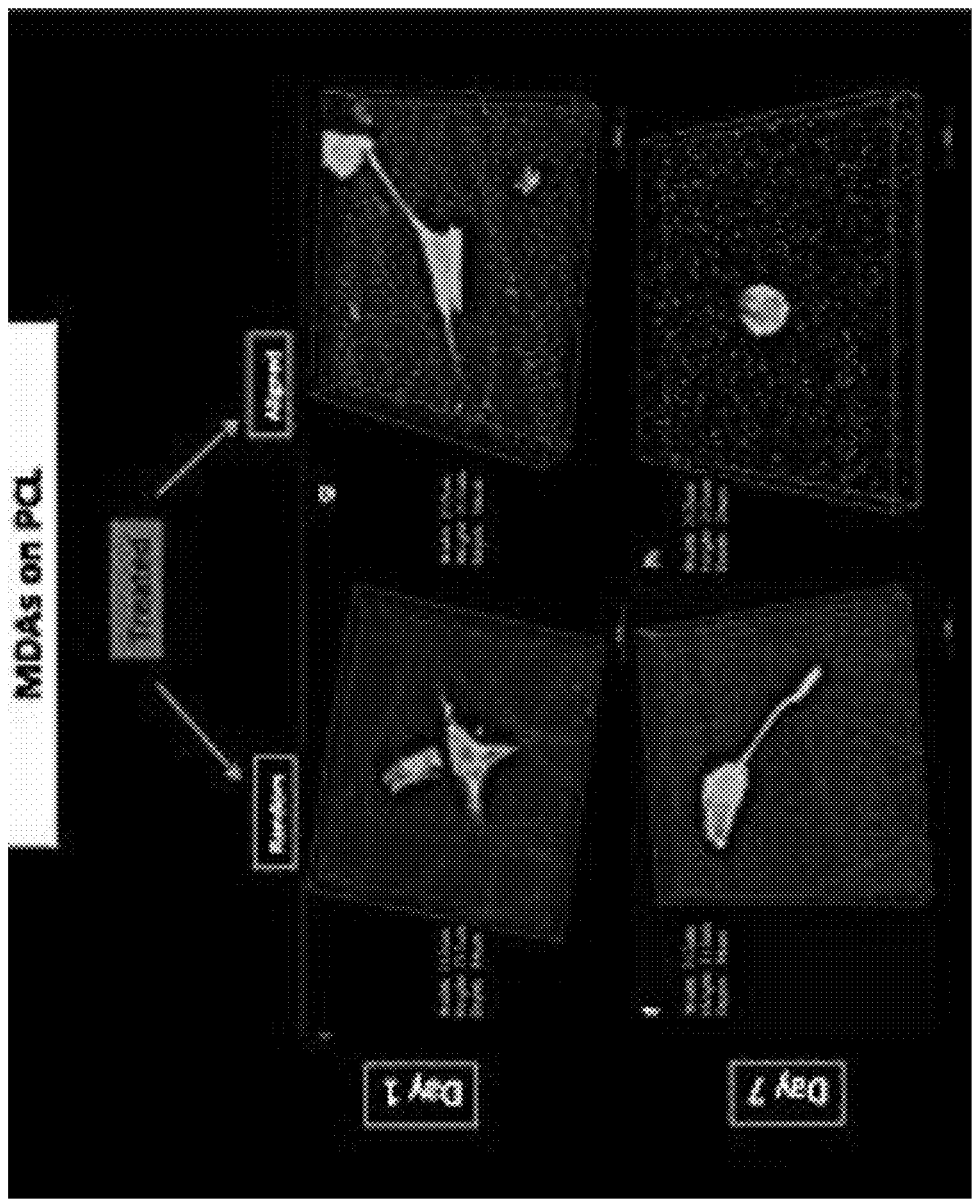
FIG. 12 shows Confocal fluorescent microscope images of MDA-MB-231 BCCs on the PCL random and aligned fibrous scaffolds. Volume View of MDA-MB-231 BCCs; green indicates F-actin (Alexa 488. On random fibers, non-treated cells at a) day 1 and b) day 7, and treated cells at e) day 1 and f) day 7. On aligned fibers, non-treated cells at c) day 1 and d) day 7 and treated cells at g) day 1 and h) day 7. 60× objective. Scale bar is 25 µm.

Moreover the volume views of cells in the 3-D-reconstructed Z-stack images showed that both non-treated and treated MDA-MB-231 cells were present within the fibrous scaffolds (FIG. 12). These findings suggest that the cancer cells may penetrate into the fibrous scaffolds and may reorient themselves in order to migrate through the fibrous structure.

Immunocytochemistry for Cyclin D1 Expression

Little to no cyclin D1 was expressed for non-treated MDA-MB-231 cells on TCP (FIG. 10). On fibrous scaffolds, non-treated MDA-MB-231 cells stained for cyclin D1 during the 7-day culture period (FIG. 8). Treated MDA-MB-231 cells expressed cyclin D1 on TCP and fibrous scaffolds during the 7-day culture period (FIG. 9).

Figure 13:
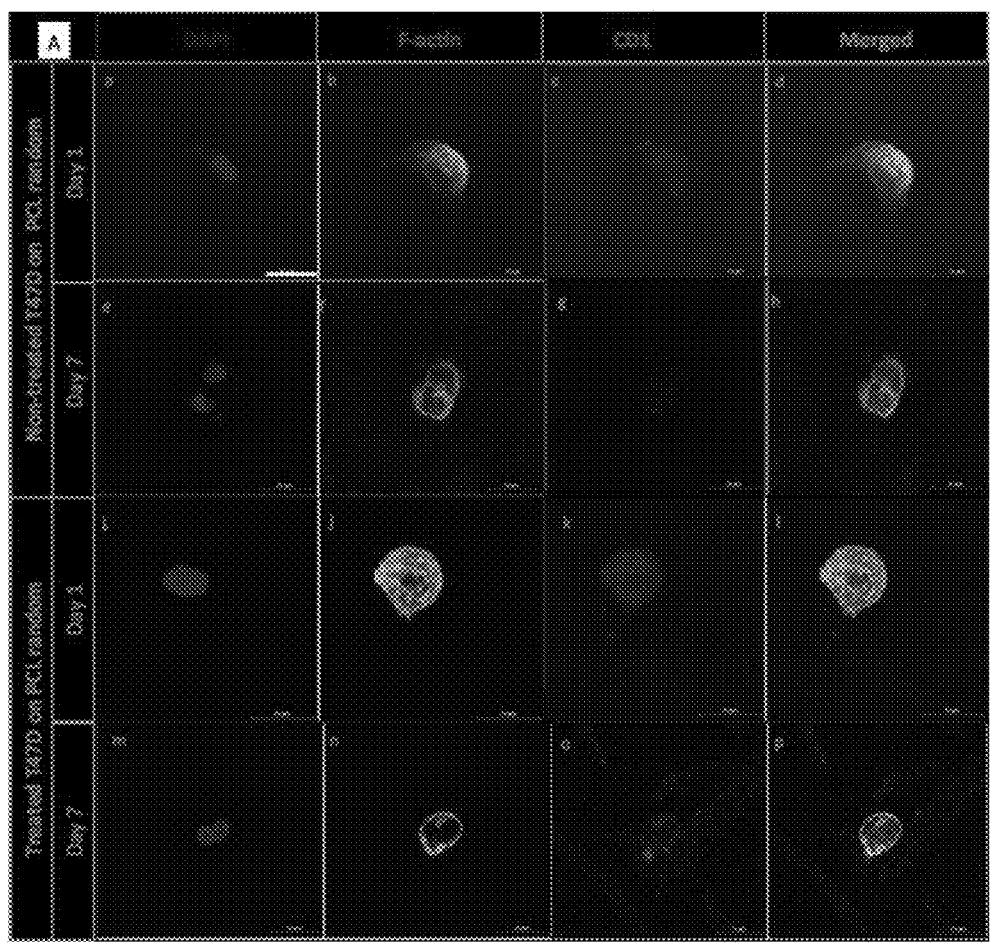
FIG. 13 shows Confocal fluorescent microscope images of T47D BCCs on the PCL random fibrous scaffolds. Blue indicates nuclei (DAPI); green indicates F-actin (Alexa 488) and red is for anti-cyclin D1 expression. Non-treated BCCs on random scaffolds (a through d at day 1; e through h at day 7) and treated BCCs (i through l at day 1; m through p at day 7). 60× objective. Scale bar is 25 µm.
Figure 14:
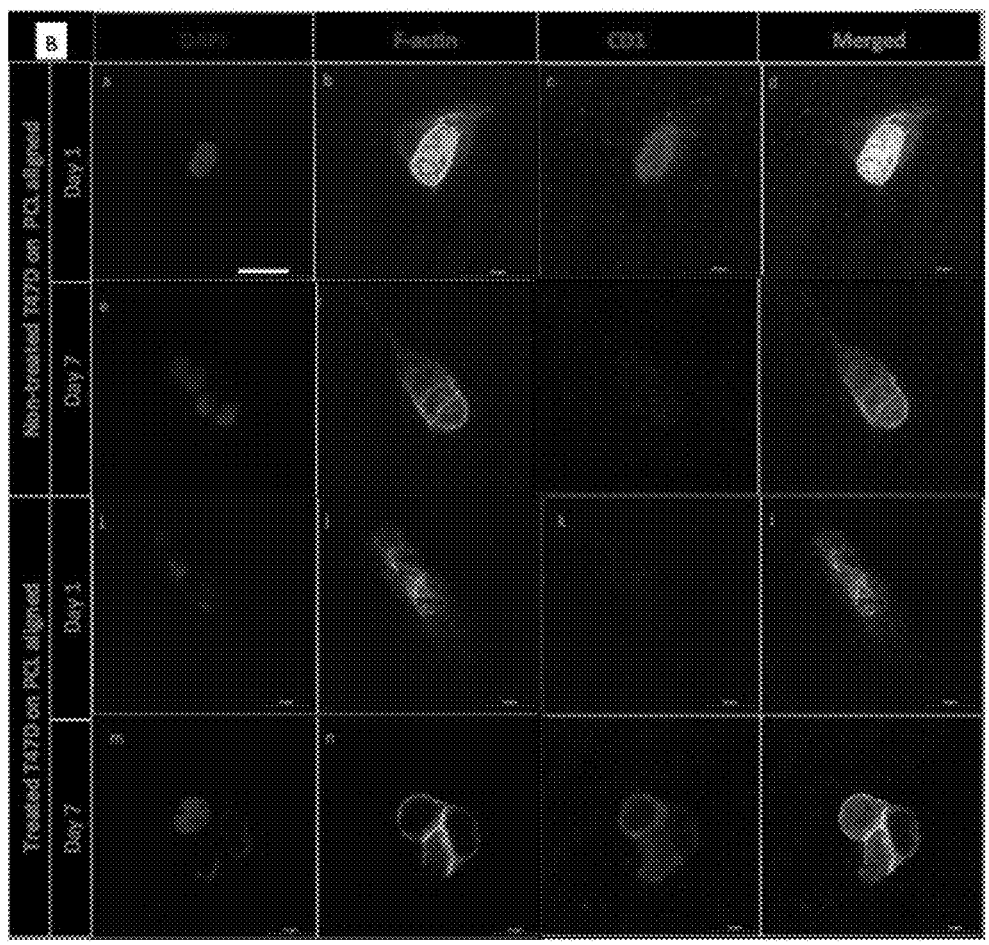
FIG. 14 shows Confocal fluorescent microscope images of T47D BCCs on the PCL aligned fibrous scaffolds. Blue indicates nuclei (DAPI); green indicates F-actin (Alexa 488) and red is for anti-cyclin D1 expression. Non-treated BCCs on aligned scaffolds (a through d—at day 1; e through h—at day 7) and treated BCCs (i through l—at day 1; m through p—at day 7). 60× objective. Scale bar is 25 µm.
Figure 15:
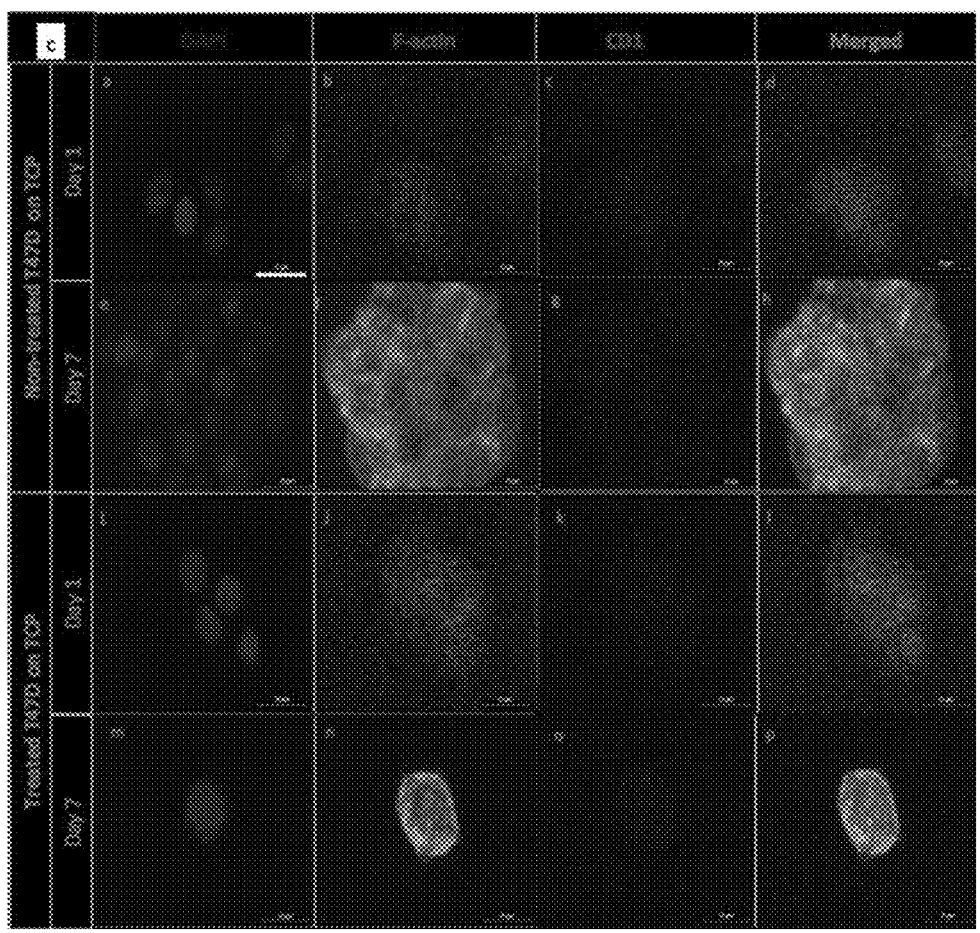
FIG. 15 shows Confocal fluorescent microscope images of T47D BCCs on the TCP control. Blue indicates nuclei (DAPI); green indicates F-actin (Alexa 488) and red is for anti-cyclin D1 expression. Non-treated BCCs (a through d—at day 1; e through h—at day 7) and treated BCCs (i through l—at day 1; m through p—at day 7). 60× objective. Scale bar is 25 µm.

Likewise, little cyclin D1 was expressed for non-treated T47D cells on TCP during the 7-day culture period (FIG. 15). On fibrous scaffolds, non-treated T47D cells stained for cyclin D1 at day 1, and little to none at day 7 (FIG. 13). Treated T47D cells expressed little cyclin D1 on TCP during the 7-day culture period (FIG. 15). On PCL random fibers, treated T47D cells stained for cyclin D1 at day 1 and little to none at day 7. Unlike on PCL aligned fibers where treated T47D cells stained for cyclin D1 at day 7 and not at day 1 (FIG. 14). These results suggested that the 3D scaffold with different fiber orientation have the potential of changing the cell cycling behavior of non-treated and treated BCCs.

Similarly, both non-treated and treated T47D cells interacted with the different scaffolds fibrous structures and showed adherence for 7 days of culture. Non-treated T47D cells had a cuboidal morphology both at day 1 and day 7 and on both random and aligned fibers. On all fiber configurations, non-treated T47D cells displayed a lagging end where it seemed the cell interacted directly with the scaffold fiber (FIGS. 13 and 14).

T47D treated cells had morphology that was more rounded on random fibers at day 1 and day 7 (FIG. 13). On aligned fibers however, T47D treated cells had cell bodies along the fibers while still holding their cuboidal morphology (FIG. 14).

Figure 16:
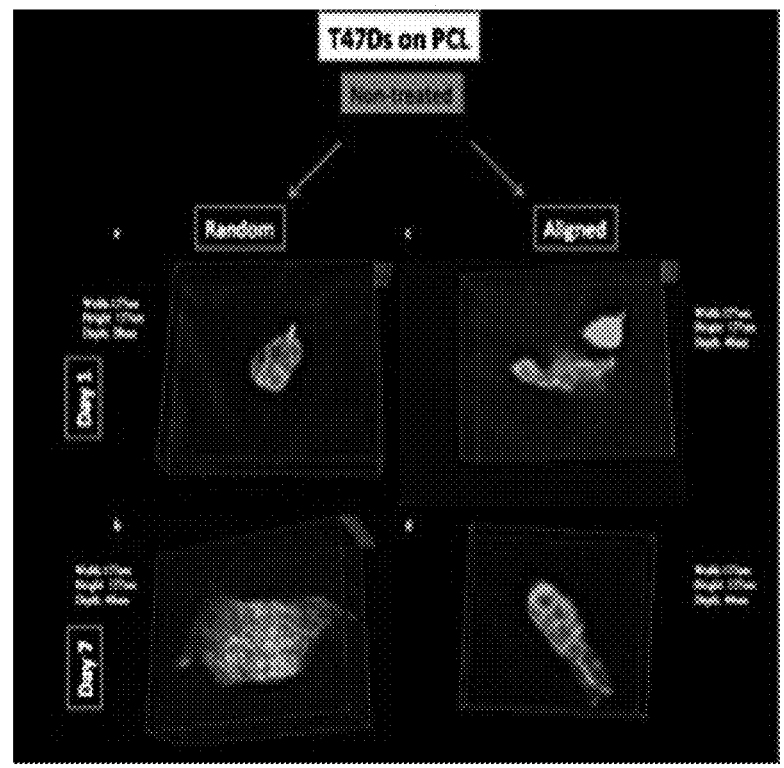
FIG. 16 shows Confocal fluorescent microscope images of MDA-MB-231 BCCs on the PCL random and aligned fibrous scaffolds. Volume View of MDA-MB-231 BCCs; green indicates F-actin (Alexa 488). On random fibers, non-treated cells at a) day 1 and b) day 7, and treated cells at e) day 1 and f) day 7. On aligned fibers, non-treated cells at c) day 1 and d) day 7 and treated cells at g) day 1 and h) day 7. 60× objective. Scale bar is 25 µm.
Figure 16:
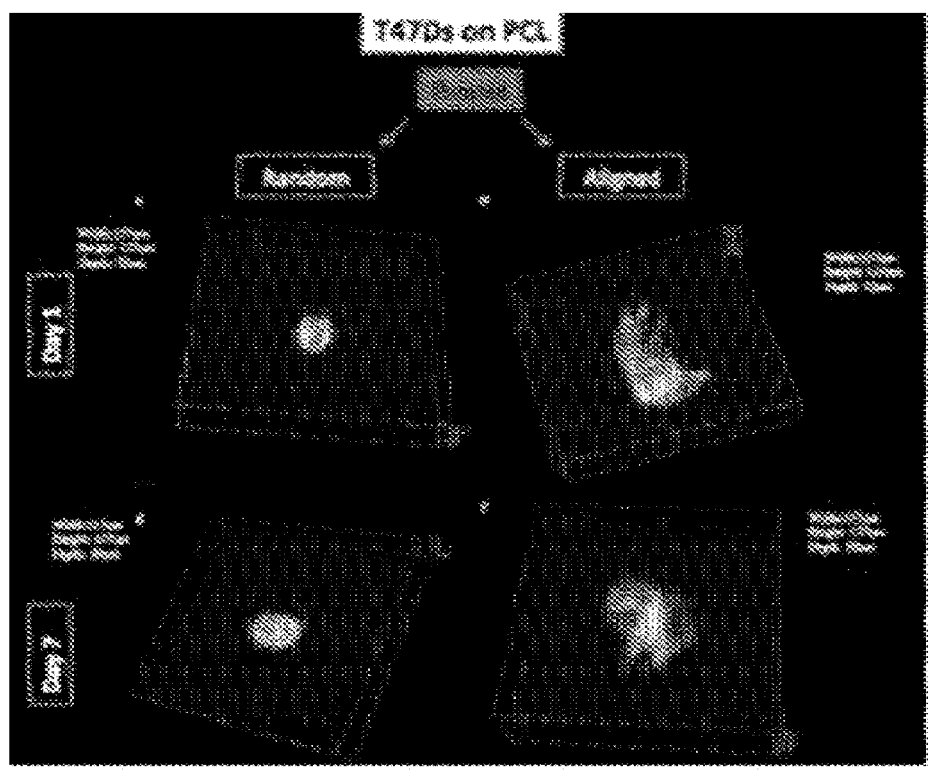

On TCP, non-treated T47D cells displayed confluency by day 7 with all cells characterized with cuboidal like shapes (FIG. 15). For treated T47D cells on TCP, cells appeared to be well attached to the substrate with several single giant cells (FIG. 15). Furthermore, the volume views of cells in the 3-D-reconstructed Z-stack images showed that both non-treated and treated T47D cells were present within the fibrous scaffolds (FIG. 16). By day 7, treated T47D cells appeared to have a rounded morphology on random fibers but the morphology varied on aligned fibers where cuboidal cells appeared elongated along the fibers (FIG. 16).

SEM imaging at higher magnification also was performed to examine adhesion and morphology of the MDA-MB-231 cells after 7 days on random and aligned fibrous scaffolds.

Figure 17:
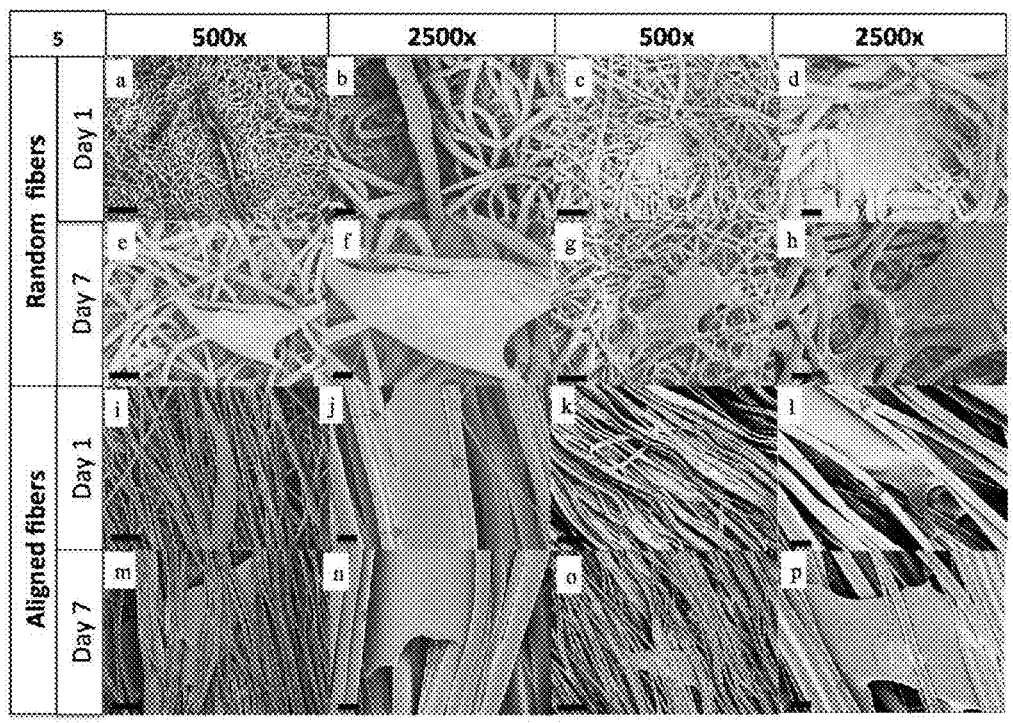
FIG. 17 shows SEM images of MDA-MB-231 cells on fibrous scaffolds after day 1 and day 7 of culture. The arrows depict the cell body and the arrowheads depict the fibers
Figure 18:
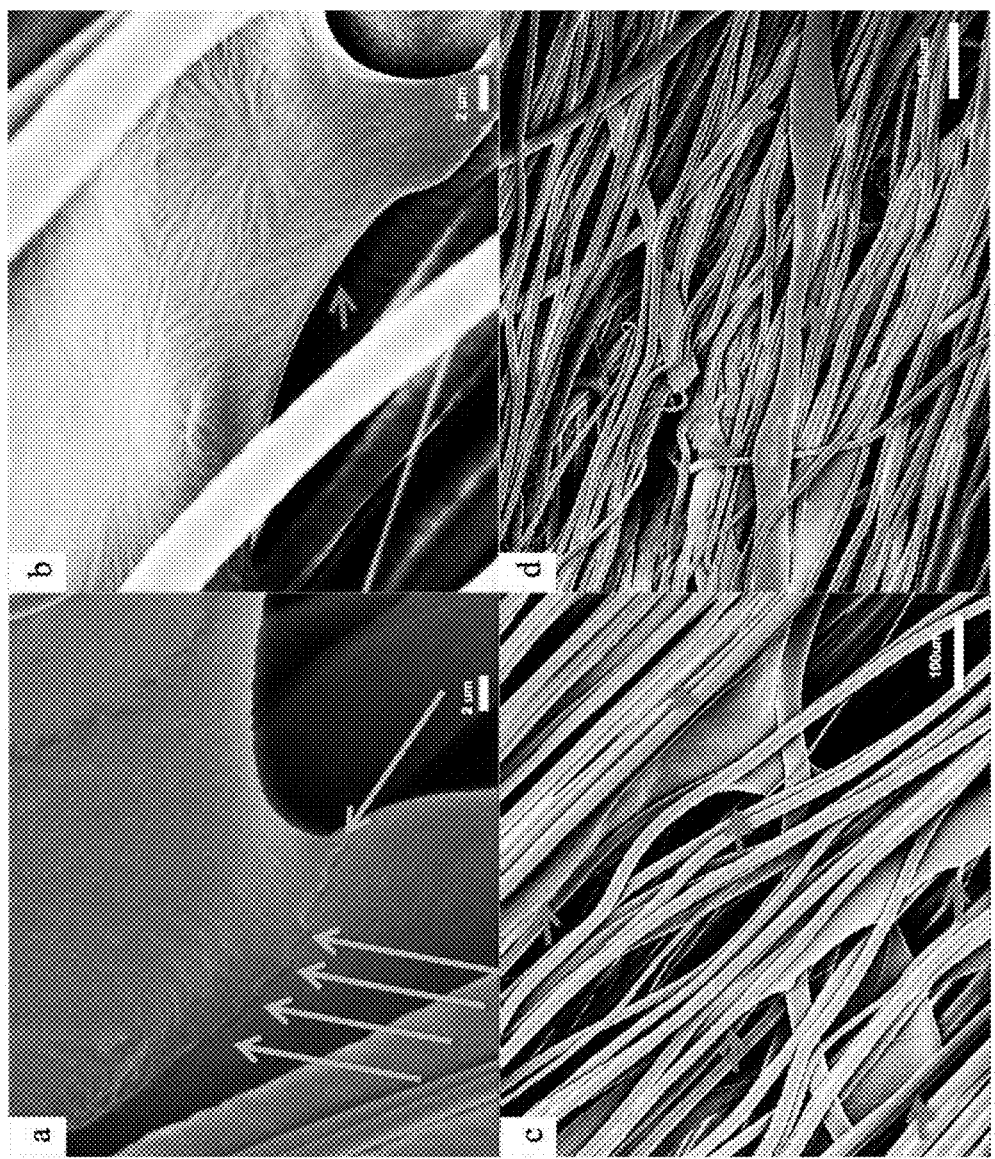
FIG. 18 shows SEM images of MDA-MB-231 cells on fibrous scaffolds after day 1 and day 7 of culture showing higher magnification analysis of adhesion and infiltration. The arrows depict the cell body and the arrowheads depict the fibers.

On random fibrous scaffolds, non-treated cells were found on the top surface of the fibers at day 1 (FIGS. 17A and 17.B) and by day 7 they had larger, more spread cell bodies (FIGS. 17.E and 17.F) interacting with the fibrous scaffolds. On aligned fibrous scaffolds, non-treated BCCs aligned their cell bodies in the direction of the fibers as early as day 1 (FIGS. 17.I and 17.J) and were found on the top surface of the fibrous scaffolds. By day 7, non-treated BCCs on aligned fibers, displayed larger cell bodies and were within the aligned fibers (FIGS. 17.M and 17.N). Treated/chemoresistant cells on random fibers displayed a more rounded cell shape at day 1 (FIGS. 17.C and 17.D) and larger cell body by day 7 (FIGS. 17.G and 17.H). On aligned fibers, treated cells aligned their cell bodies along the fibers at day 1 (FIGS. 17.K and 17.L) and had large cell bodies by day 7. Cells on both random and aligned fibrous scaffolds displayed cell-cell (FIG. 18C, D) and cell-fiber (FIG. 18.A-C) interactions. SEM demonstrated that cancer cells were attached to the scaffold. Individual cancer cell and cancer cell aggregates attached and spread on the surface of the fibrous scaffold and many cells attached to neighboring cells as shown (FIG. 18C.)

So far, morphology and Cyclin D1 expression results from MDA-MB-231 basal like BCCs and T47D epithelial like BCCs showed that overall the 3-D scaffolds with random and aligned oriented microfibers allowed the different BCCs to establish attachments and penetrate within the fibers as early as day 1. Since these 2 different BCCs cell lines were capable of sensing and responding to the 3-D fibers with random and aligned orientations we further looked into the growth, viability migration and cell cycle profiles of these BCCs on the scaffolds.

Cell Proliferation

Cell proliferation assays of both MDA-MB-231 and T47D cells on scaffolds were assessed and analyzed after 7 days of culture.

Figure 19:
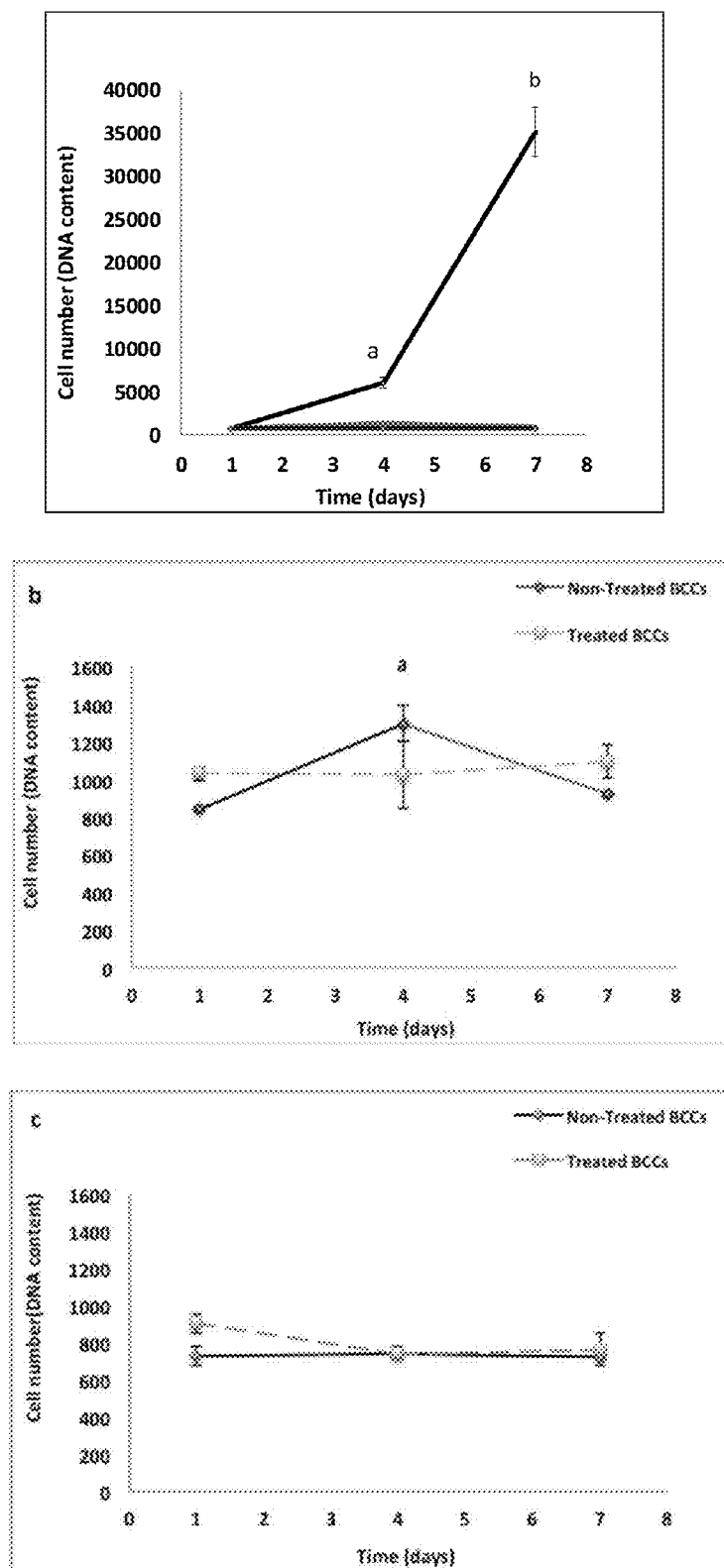
FIG. 19 shows MDA-MB-231 cell growth on random and aligned fibrous scaffolds in comparison to TCP. a) TCP. $^a$ $p<0.05$, significant increase in growth of non-treated BCCs at day 4 as compared to day 1. $^b$ $p<0.05$, significant increase in growth of non-treated BCCs at day 7 as compared to day 1 and day 4. b) Random fibers. $^a$ $p<0.05$, significant increase in growth of non-treated BCCs at day 4 as compared to day 1 and day 7. c) Aligned fibers. Values are mean±SD. Studies were repeated 3 times. N=4.

On TCP, non-treated MDA-MB-231 BCCs displayed significant increase in cell number at days 4 and 7 as compared to day 1 ($p<0.05$) (FIG. 19.a). Non-treated MDA-MB-231 BCCs showed a slight increase in cell growth at day 4 ($p<0.05$) on random fibrous scaffolds (FIG. 19.b). On PCL aligned, non-treated MDA-MB-231 BCCs did not display significant difference in growth during the 7-day culture (FIG. 19c). No differences in cell number were detected over time for treated MDA-MB-231 BCCs on TCP and fibrous scaffolds (FIG. 19.a-c).

Figure 20:
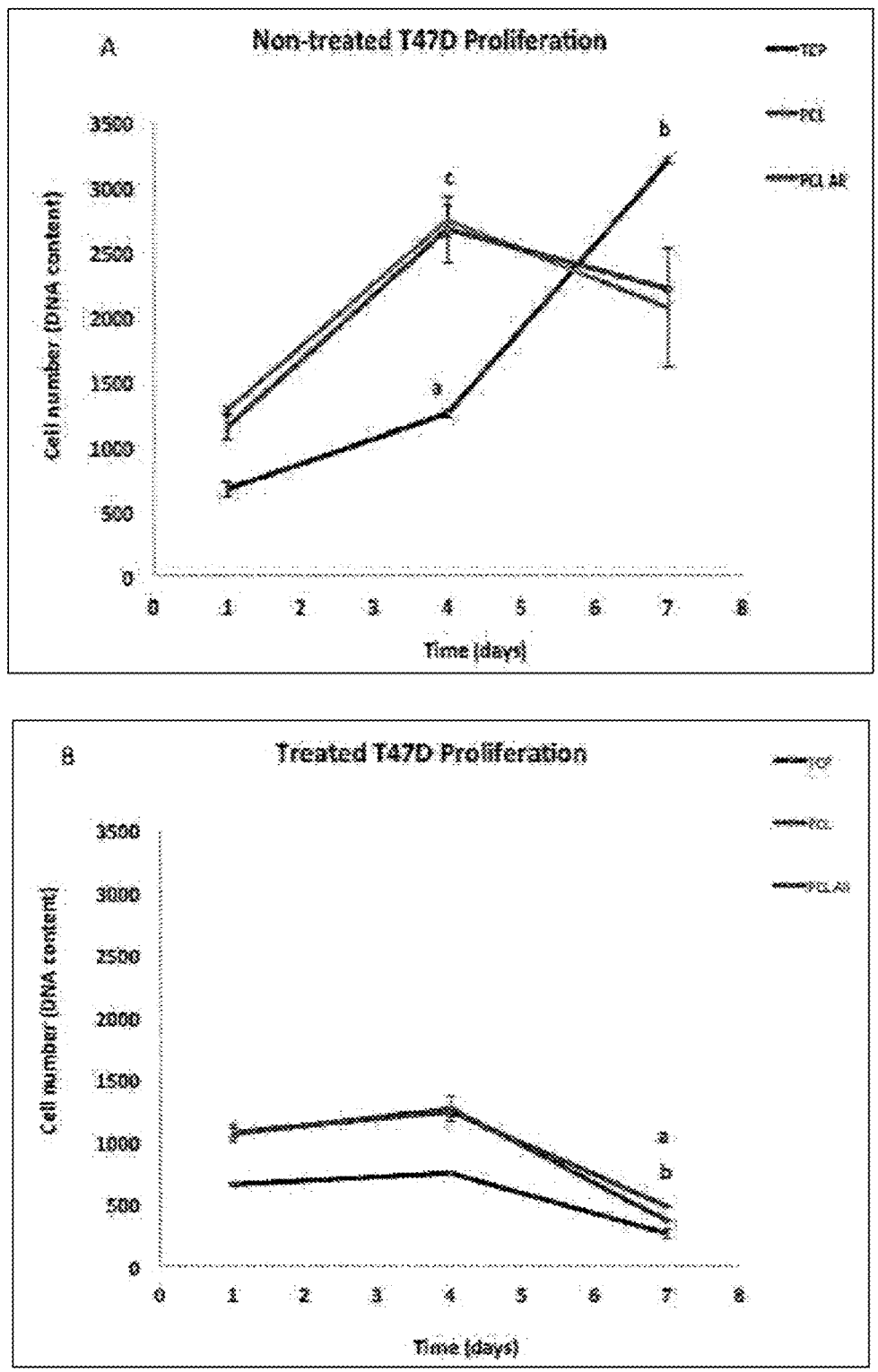
FIG. 20 shows T47D cell growth on random and aligned fibrous scaffolds in comparison to TCP. A) Non-treated T47D cells. $^a$ $p<0.05$, significant increase in growth of non-treated T47D on TCP at day 4 as compared to day 1. $^b$ $p<0.05$, significant increase in growth of non-treated BCCs on TCP at day 7 as compared to day 1 and day 4. $^c$ $p<0.05$, significant increase in growth of T47D cells on fibrous scaffolds at day 4 as compared to day 1. B) Treated T47D cells. $^a$ $p<0.05$, significant decrease in growth of treated T47D cells on TCP at day 7 as compared to day 1 and day 4. $^b$ $p<0.05$, significant decrease in growth of T47D on fibrous scaffolds at day 7 as compared to day 1 and day 4. Values are mean±SD. Studies were repeated 3 times. N=4.

On TCP, non-treated T47D cells displayed significant increase in cell number at days 4 and 7 as compared to day 1 ($p<0.05$) (FIG. 20a). Non-treated T47D cells showed a significant increase in cell growth at day 4 ($p<0.05$) on both random and aligned fibrous scaffolds (FIG. 20a) as compared to day 1. Treated T47D cells showed a significant decrease in growth ($p<0.05$) at day 7 as compared to day 1 and day 4 on both TCP and the fibrous scaffolds. (FIG. 20b).

Figure 21:
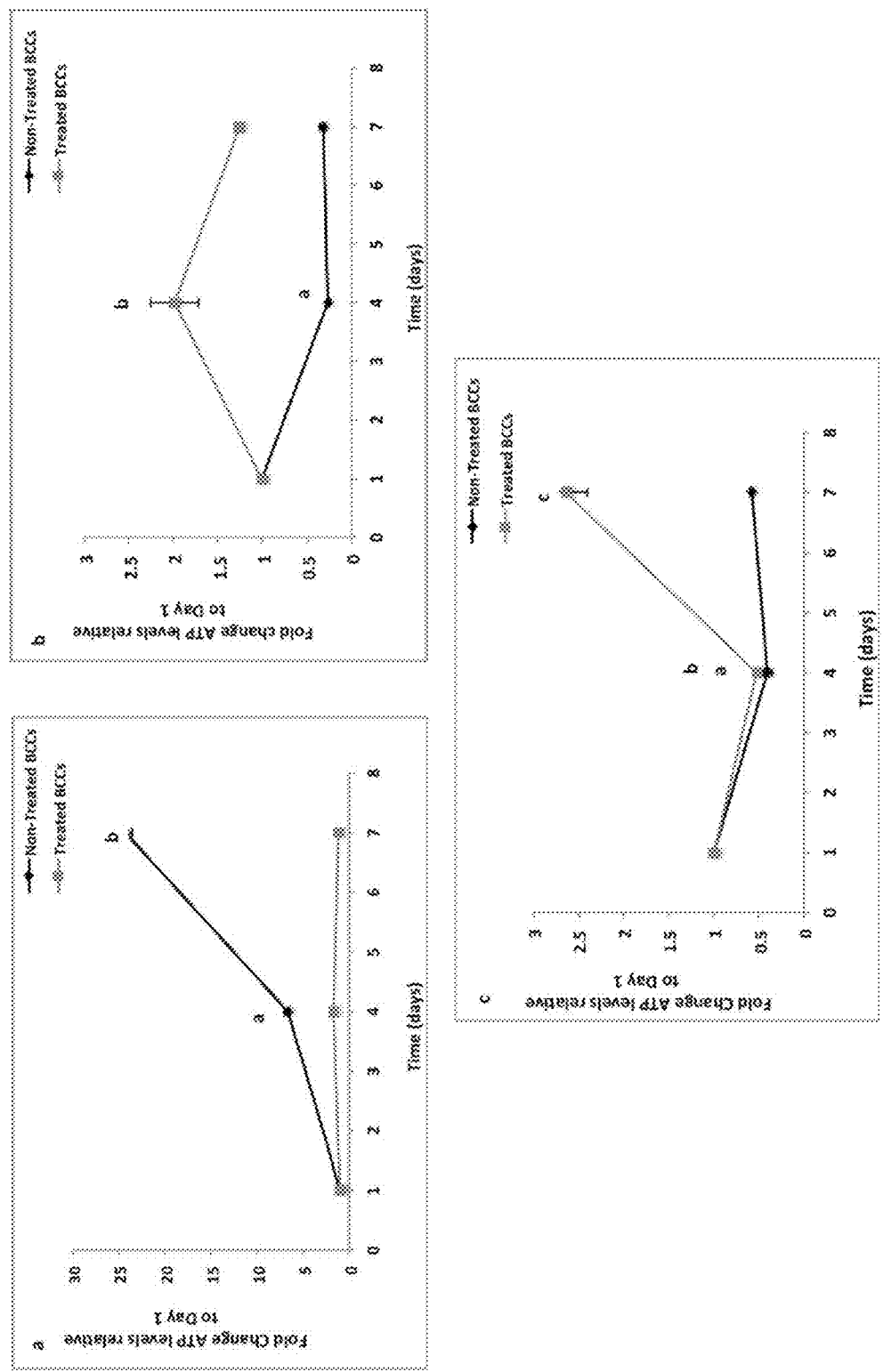
FIG. 21 shows Metabolic activity of MDA-MB-231 cells on random and aligned fibrous scaffolds in comparison to TCP. a) TCP. $^{a,b}$ $p<0.05$, significant increase in metabolically active non-treated MDA-MB-231 cells at day 4 and day 7 as compared to day 1. b) Random fibers. $^a$ $p<0.05$, significant decrease in metabolic activity of non-treated MDA-MB-231 cells as compared to day 1. $^b$ $p<0.05$, significant increase in metabolic activity of treated MDA-MB-231 cells at day 4 as compared to day 1. c) Aligned fibers. $^a$ $p<0.05$, significant decrease in metabolic activity of non-treated MDA-MB-231 cells as compared to day 1. $^b$ $p<0.05$, significant decrease in metabolic activity of treated MDA-MB-231 cells as compared to day 1. $^c$ $p<0.05$, significant increase in metabolic activity of treated MDA-MB-231 cells in comparison to days 1 and 4. Values are mean±SD. Studies were repeated 3 times. N=4.

On TCP, non-treated MDA-MB-231 BCCs displayed a significant increase in metabolic activity ($p<0.05$) over time (~7 fold and ~25 fold increase as compared to day 1) (FIG. 21.a).

Non-treated MDA-MB-231 BCCs had significantly lower metabolic activity during the 7-day culture period on fibrous scaffolds as compared to TCP (FIG. 21a-c). On TCP, no differences in metabolic activity were detected for treated MDA-MB-231 BCCs over the 7-day culture period. On random fibrous scaffolds, treated MDA-MB-231 BCCs had a 2-fold ($p<0.05$) significant increase in metabolic activity at day 4 as compared to day 1 (FIG. 21b). Treated MDA-MB-231 BCCs on aligned fibrous scaffolds showed a significant decrease ($p<0.05$) in metabolic activity at day 4 and a significant increase in metabolic activity ($p<0.05$) at day 7 (FIG. 21c).

Figure 22:
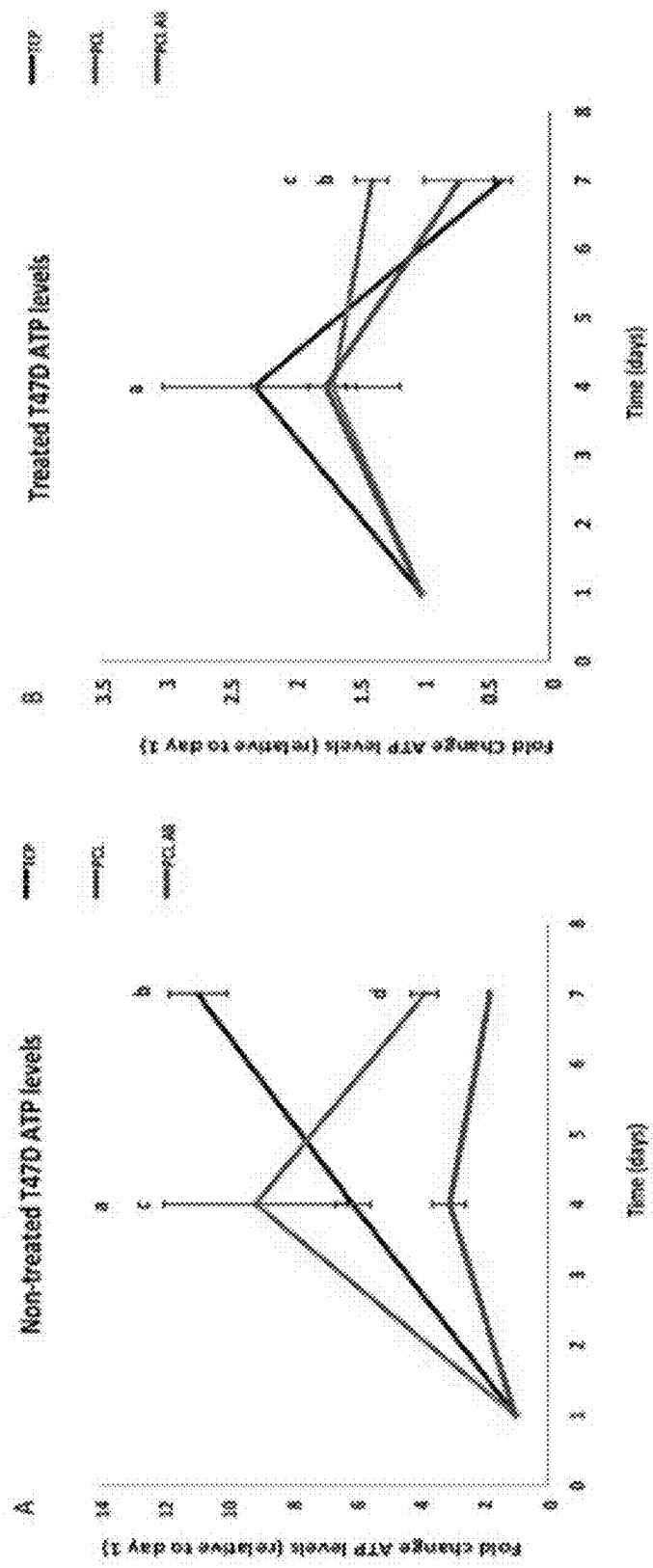
FIG. 22 shows Metabolic activity of T47D cells on random and aligned fibrous scaffolds in comparison to TCP. A) Non-treated T47D cells. $^a$ $p<0.05$, significant increase in metabolically active non-treated T47D cells on TCP at day 4 as compared to day 1. $^b$ $p<0.05$, significant increase in metabolically active non-treated T47D cells on TCP at day 7 as compared to days 1 and 4. $^c$ $p<0.05$, significant increase in metabolically active non-treated T47D cells on PCL random scaffolds at day 4 as compared to day 1. $^d$ $p<0.05$, significant decrease in metabolically active non-treated T47D cells on PCL random at day 7 as compared to days 1 and 4. B) Treated T47D cells. $^a$ $p<0.05$, significant increase in metabolically active treated T47D cells on TCP at day 4 as compared to day 1. $^b$ $p<0.05$, significant decrease in metabolically active treated T47D cells on TCP at day 7 as compared to days 1 and 4. $^c$ $p<0.05$, significant decrease in metabolically active treated T47D cells on PCL aligned at day 7 as compared to day 4. Values are mean±SD. Studies were repeated 3 times. N=4

Metabolic activity of T47D cells on random and aligned fibrous scaffolds in comparison to TCP was also evaluated. On TCP, non-treated T47D cells displayed a significant increase in metabolic activity ($p<0.05$) over time (6 fold and ~11 fold increase as compared to day 1) (FIG. 22a).

On PCL random fibers non-treated T47D cells had significantly higher metabolic activity at day 4 ($p<0.05$) as compared to day 1 followed by a significant decrease in metabolic activity at day 7 ($p<0.05$) as compared to days 1 and 4. (FIG. 22a).

Treated T47D cells overall had a very low metabolic activity on both fibrous scaffolds and TCP as compared to non-treated T47D cells. On TCP, treated T47D cells had a significant increase in metabolic activity at day 4 ($p<0.05$) as compared to day 1 followed by a significant decrease in metabolic activity at day 7 ($p<0.05$) as compared to days 1 and 4 (FIG. 22b). There was a significant decrease in metabolically active treated T47D cells on PCL aligned at day 7 ($p<0.05$) as compared to day 4. There was no significant change in metabolic activity of treated T47D cells on PCL random scaffolds during the 7-day culture (FIG. 22b).

Cell Cycle Analyses

On TCP for non-treated cells at day 1, 29% of the cells were in G0/G1 phase, 66% of the cells were in S phase, and 5% of the cells were in G2 phase (FIG. 23a). By day 7, 37% of the cells were in G0/G1 phase, 63% of the cells were in S phase and none of the cells cycled to G2 phase (FIG. 23d). Thus, more than 60% of non-treated cells were in S phase of the cell cycle for the 7-day culture period.

Non-treated cells on random scaffolds at day 1, showed that 42% were in G0/G1 phase, while 58% of the cells were in S phase, and none of the cells cycled to G2 phase (FIG. 23b). By day 7, 29% of the cells were in G0/G1 phase and 71% of the cells transitioned to the S phase while none of the cells cycled to G2 phase (FIG. 23e). Thus comparing day 1 to day 7, cells were more evenly distributed between G0/G1 phase and S phase at day 1, and by day 7 more cells were in the S phase than G0/G1 phase.

Figure 23:
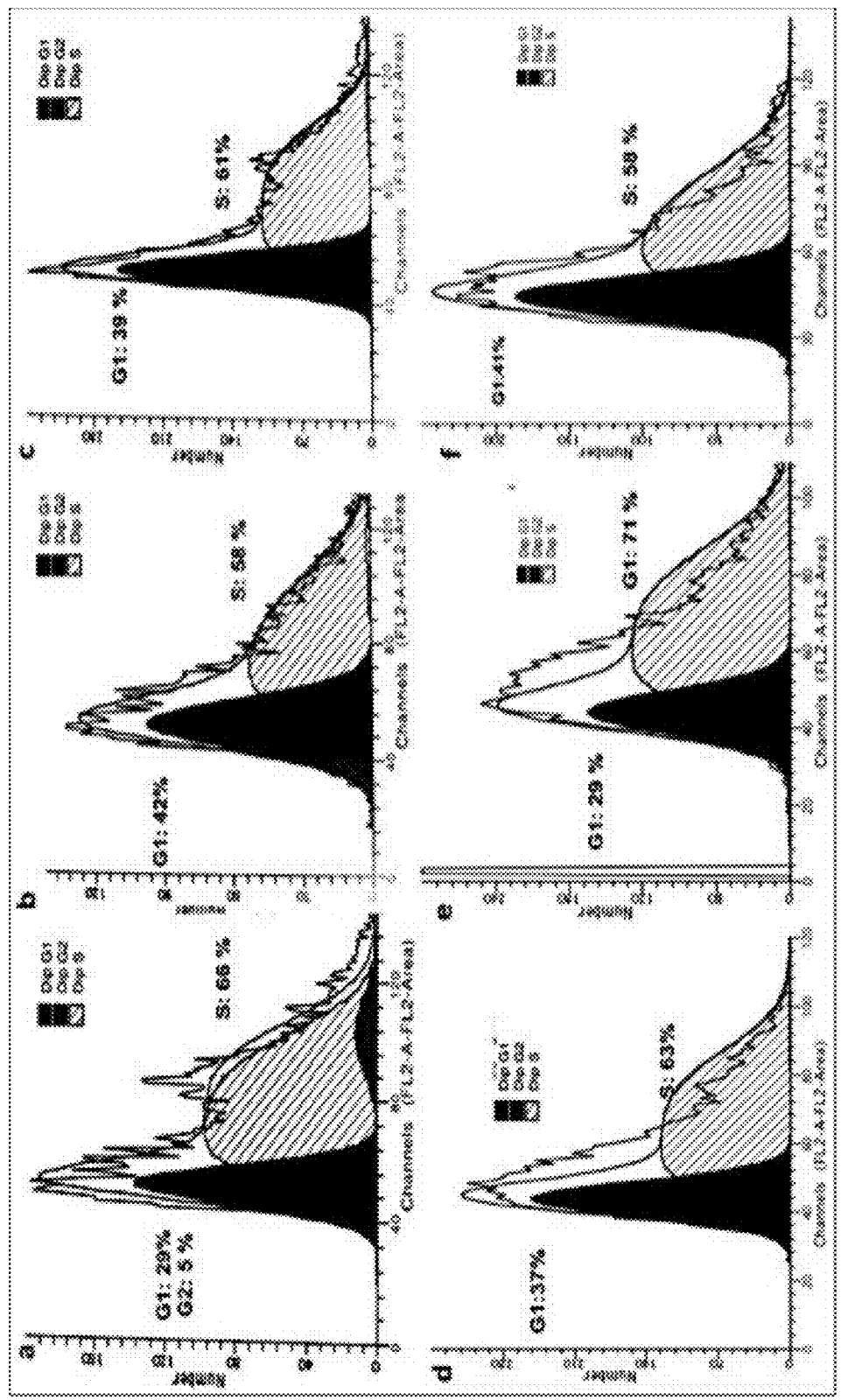
FIG. 23 shows Analysis of cell cycle phase for non-treated BCCs by flow cytometry on: TCP at a) day 1 and d) day 7, random fibrous scaffolds at b) day 1 and e) day 7, and aligned fibrous scaffolds at c) day 1 and f) day 7. Studies were repeated 2 times. N=2.

On aligned fibrous scaffolds at day 1, 39% of the non-treated cells were in G0/G1 phase, 61% of the cells were in S phase, and none of the cells cycled to G2 phase (FIG. 23.c). By day 7, 42% of the cells were in G0/G1 phase, 58% of the cells were in S phase and none of the cells were in G2 phase (FIG. 23f). Thus at day 1, more cells were in the in the S phase than G0/G1 phase. However by day 7, cells were more evenly distributed in G0/G1 phase and in the S phase.

Figure 24:
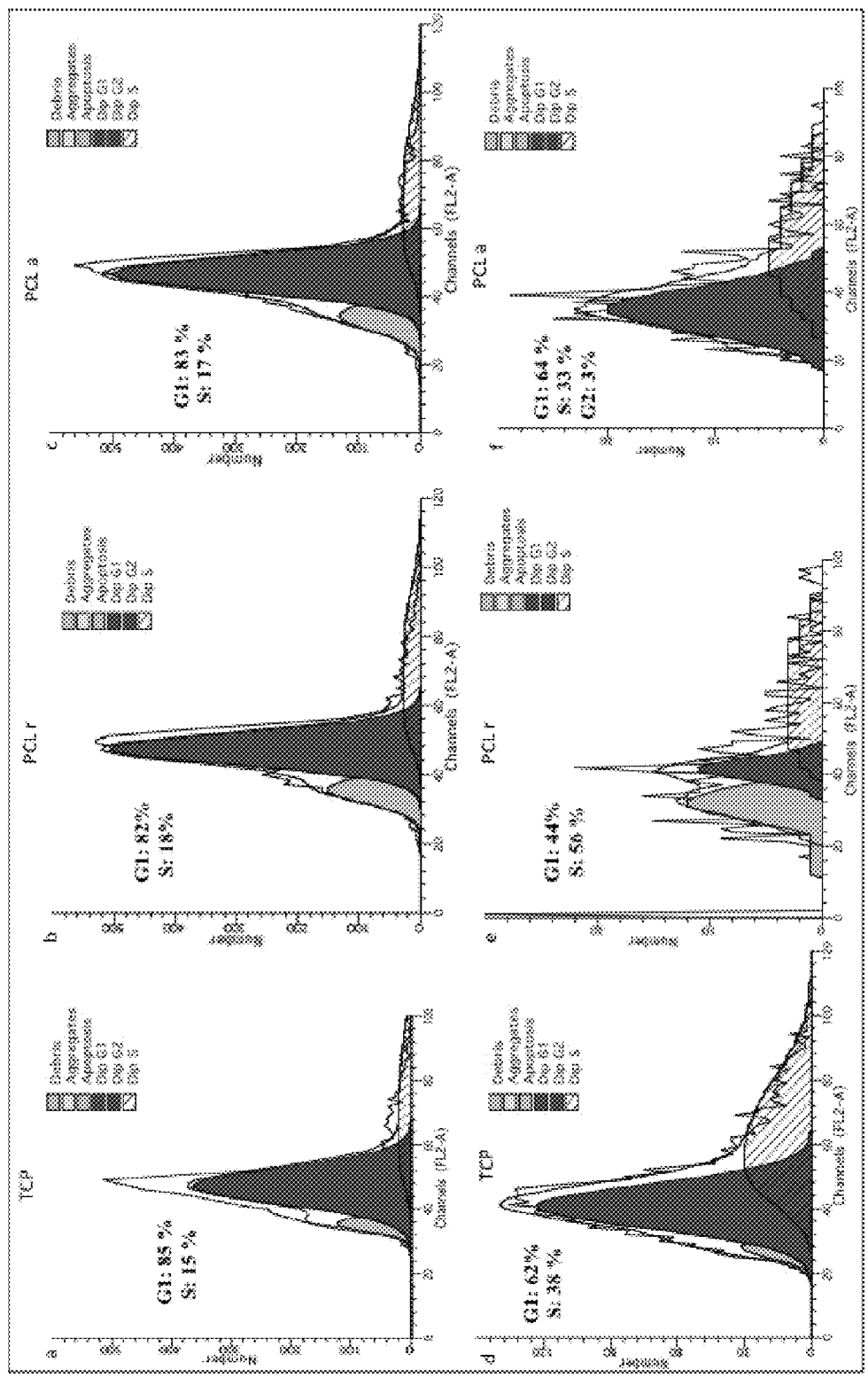
FIG. 24 shows Analysis of cell cycle phase for treated BCCs by flow cytometry on: TCP at a) day 1 and d) day 7, random fibrous scaffolds at b) day 1 and e) day 7, and aligned fibrous scaffolds at c) day 1 and f) day 7. Studies were repeated 2 times. N=2.

On TCP for treated (dormant) cells at day 1, 85% of the cells were in G0/G1 phase, 15% of the cells were in S phase (FIG. 23a). By day 7, 62% of the cells were in G0/G1 phase, 38% of the cells were in S phase and none of the cells cycled to G2 phase (FIG. 24d). Thus, more than 60% of treated (dormant) cells were in G1 phase of the cell cycle for the 7-day culture period.

Treated (dormant) cells on PCL random scaffolds at day 1, showed that 82% were in G0/G1 phase, while 18% of the cells were in S phase, and none of the cells cycled to G2 phase (FIG. 24b). By day 7, 44% of the cells were in G0/G1 phase and 56% of the cells transitioned to the S phase while none of the cells cycled to G2 phase (FIG. 24e). Thus comparing day 1 to day 7, at day 1 more treated cells were in G0/G1 phase than the S phase. Treated (dormant) cells were more evenly distributed between G0/G1 phase and S phase at day 7 on PCL random fibers.

Figure 3:
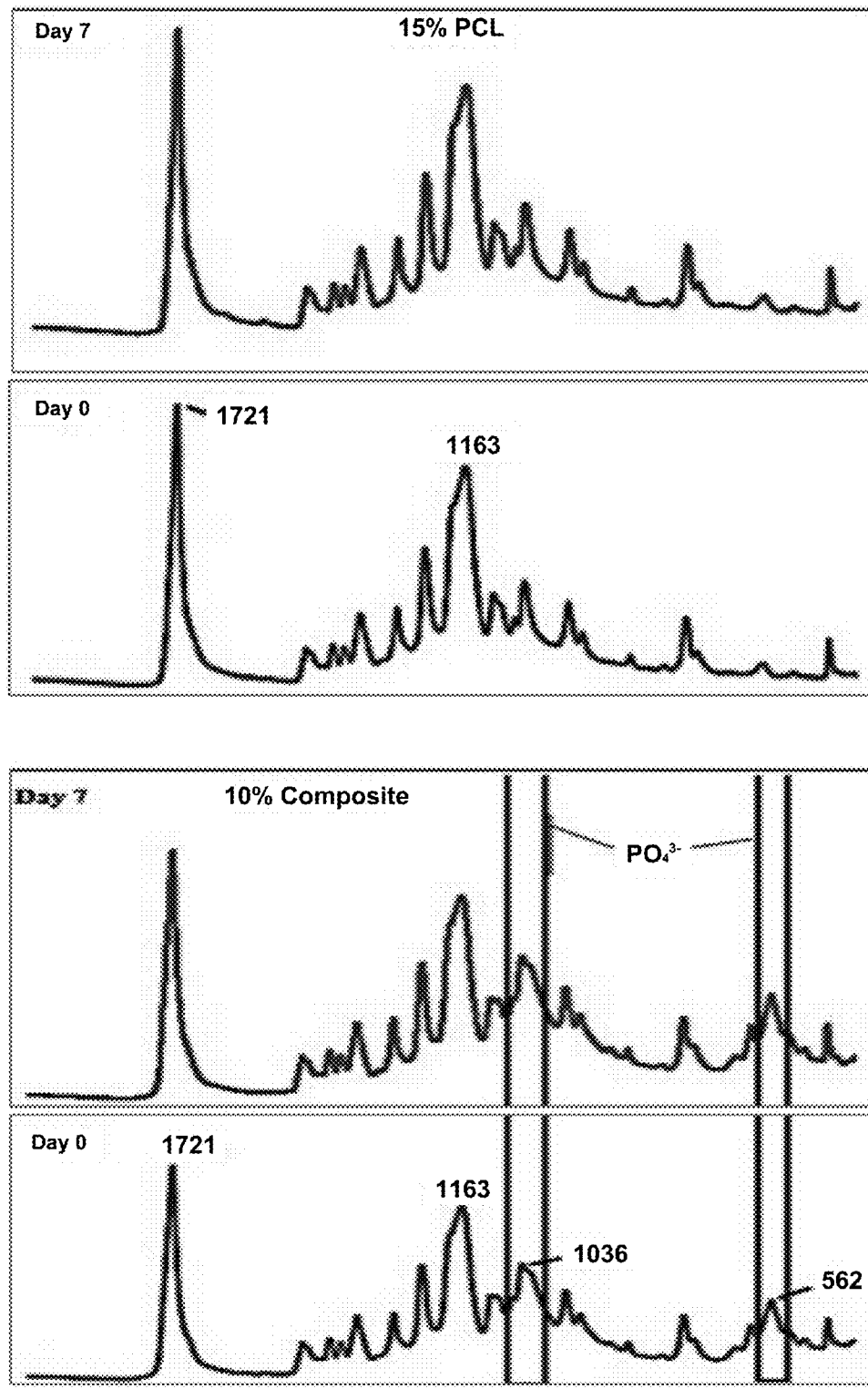
FIG. 3 shows FTIR spectrum of (A) PCL only mats and (B) PCL+HA scaffolds at day 0 and 7.
Figure 34:
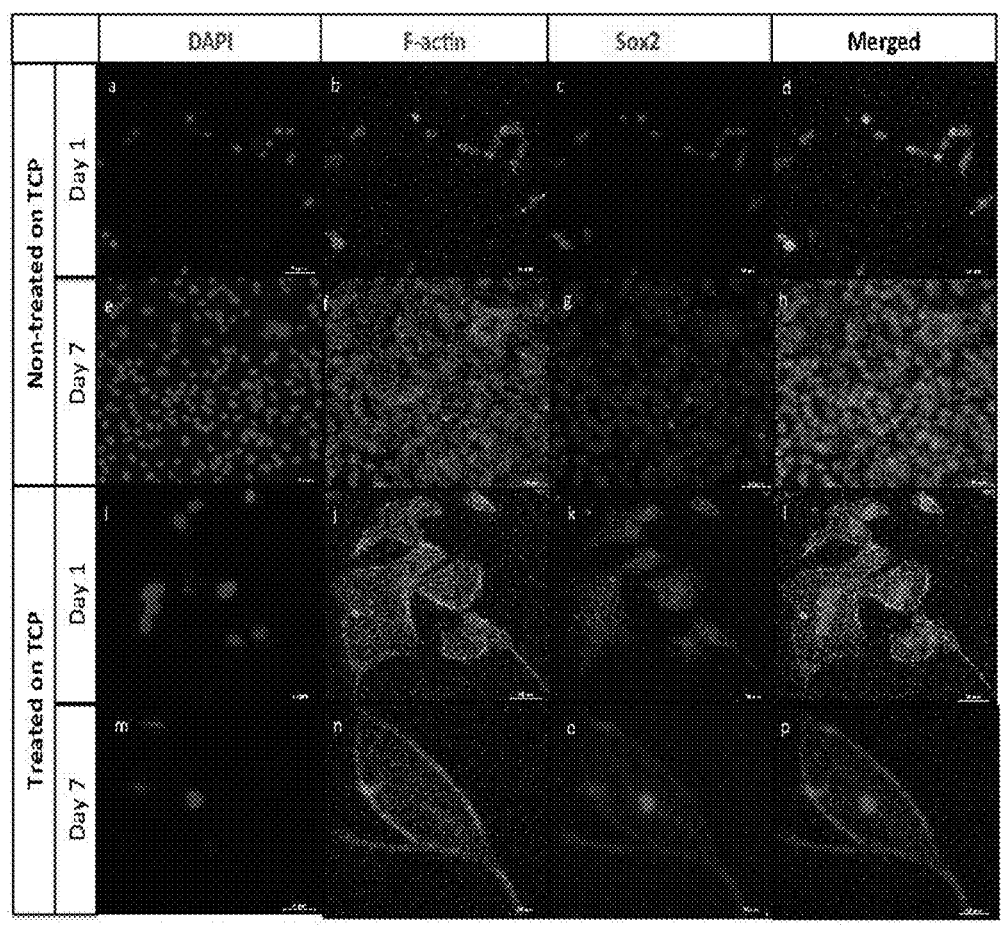
FIG. 34 shows Confocal fluorescent microscope images of Sox2 protein expression of MDA-MB-231 BCCs on TCP control. Blue indicates nuclei (DAPI); green indicates F-actin (Alexa 488) and red is for anti-Sox2 protein. Non-treated BCCs (a through d at day 1; e through h at day 7) and treated BCCs (i through l at day 1; m through p at day 7) on TCP. All scale bars are 50 □m. 100× objective.
Figure 35:
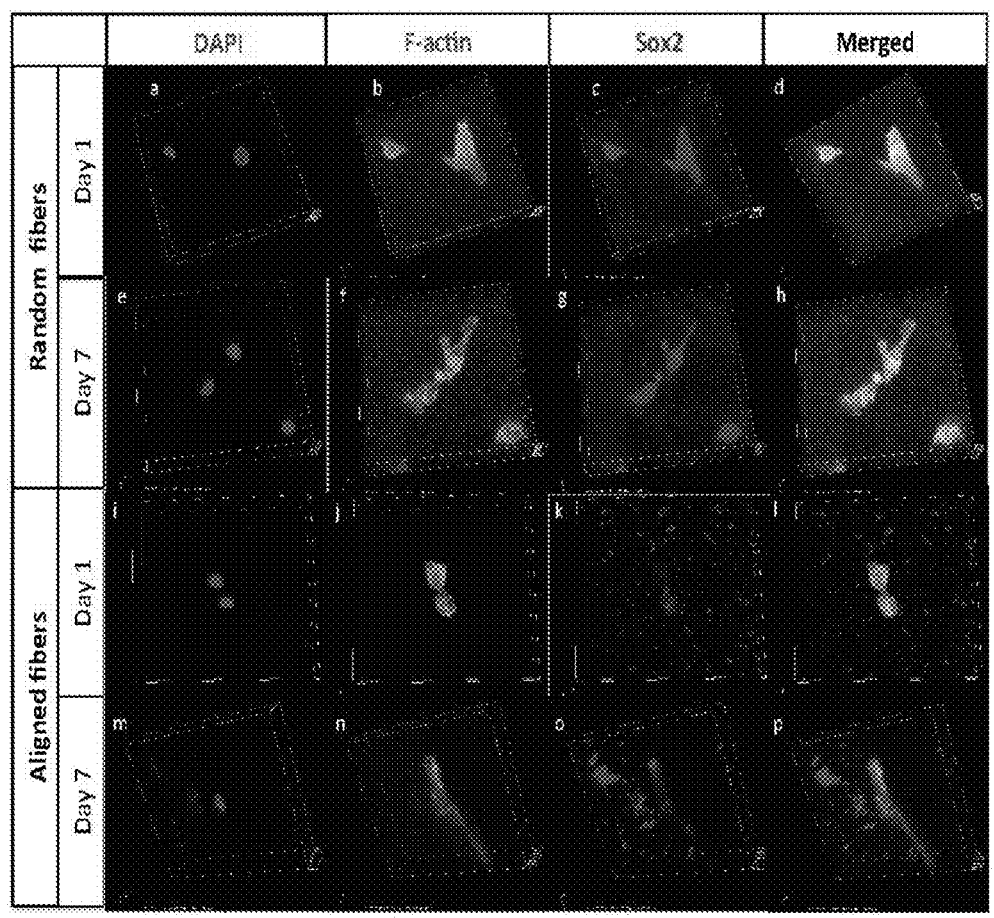
FIG. 35 shows Confocal fluorescent microscope images of Sox2 protein expression of non-treated MDA-MB-231 BCCs on the PCL random and aligned fibrous scaffolds. Blue indicates nuclei (DAPI); green indicates F-actin (Alexa 488) and red is for anti-Sox2 protein. A) Non-treated BCCs on random scaffolds (a through d at day 1; e through h at day 7) and aligned scaffolds (i through l at day 1; m through p at day 7).
Figure 36:
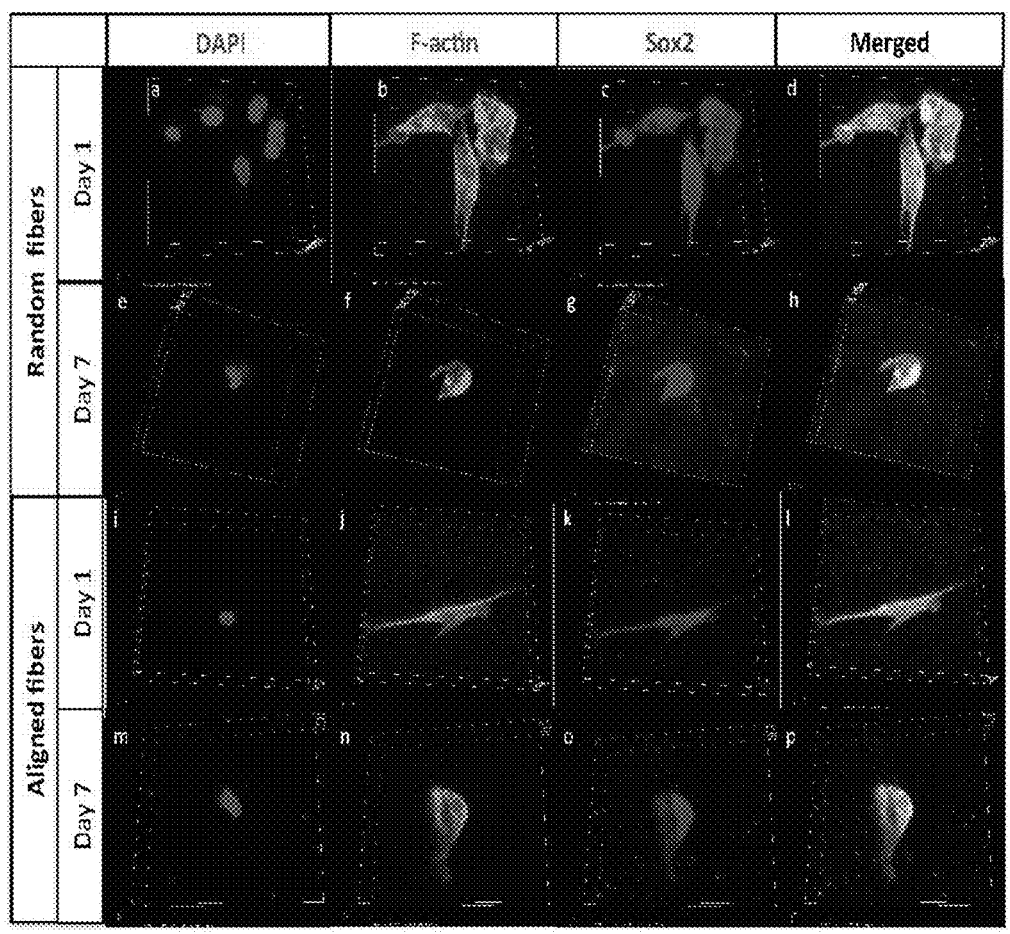
FIG. 36 shows Confocal fluorescent microscope images of Sox2 protein expression of treated MDA-MB-231 BCCs on the PCL random and aligned fibrous scaffolds. Treated BCCs on random scaffolds (a through d at day 1; e through h at day 7) and aligned scaffolds (i through l at day 1; m through p at day 7).

On PCL aligned fibrous scaffolds at day 1, 83% of treated (dormant) cells were in G0/G1 phase, 17% of the treated (dormant) cells were in S phase, and none of the cells cycled to G2 phase (FIG. 3.21.c). By day 7, 64% of the treated (dormant) cells were in G0/G1 phase, 33% of the treated (dormant) cells were in S phase and 3% of the cells were in G2 phase (FIG. 34f). Thus at day 1, more treated (dormant) cells were in the in G0/G1 phase than the S phase. However by day 7, seeded treated (dormant) cells were cycling on PCL aligned scaffolds.

Anti-Apoptotic, Sternness and Self-Renewal Proteins Immunostaining

Immunostaining to analyze expression of anti-apoptotic proteins Bax and Bcl2, stemness protein Oct-4, and self-renewal protein Sox2 by MDA-MB-231 BCCs on scaffolds was also performed.

Figure 25:
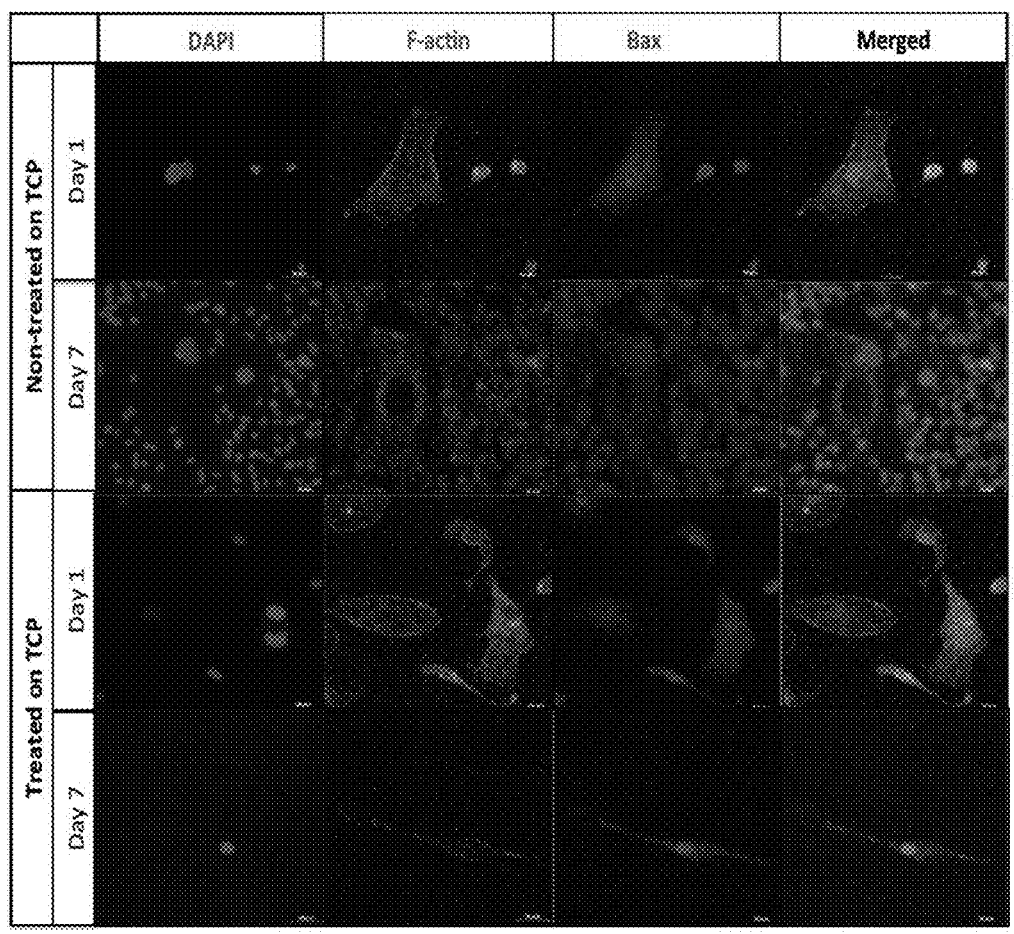
FIG. 25 Confocal fluorescent microscope images of Bax protein expression of MDA-MB-231 BCCs on TCP control. Blue indicates nuclei (DAPI); green indicates F-actin (Alexa 488) and red is for anti-Bax protein. Non-treated BCCs (a through d at day 1; e through h at day 7) and treated BCCs (i through l at day 1; m through p at day 7) on TCP.
Figure 26:
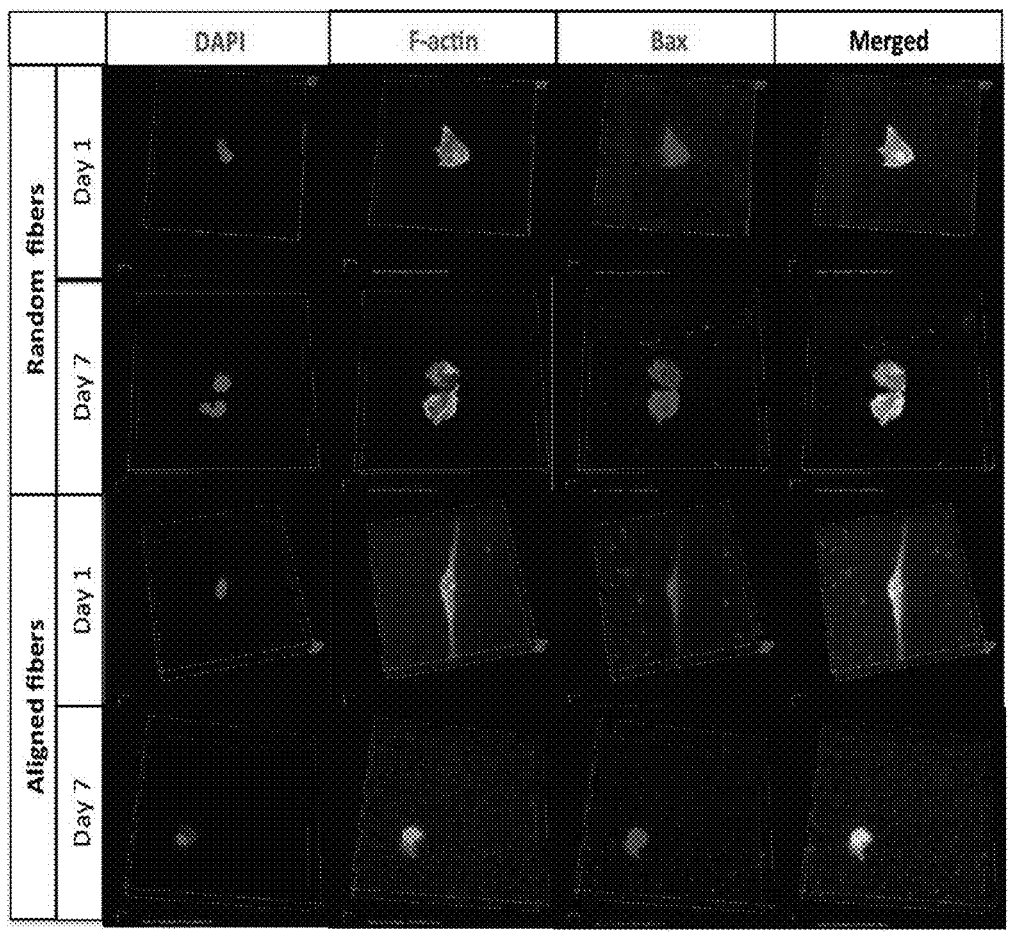
FIG. 26 shows Confocal fluorescent microscope images of Bax protein expression of non-treated MDA-MB-231 BCCs on the PCL random and aligned fibrous scaffolds. Blue indicates nuclei (DAPI); green indicates F-actin (Alexa 488) and red is for anti-Bax protein. Non-treated BCCs on random scaffolds (a through d at day 1; e through h at day 7) and aligned scaffolds (i through l at day 1; m through p at day 7).
Figure 27:
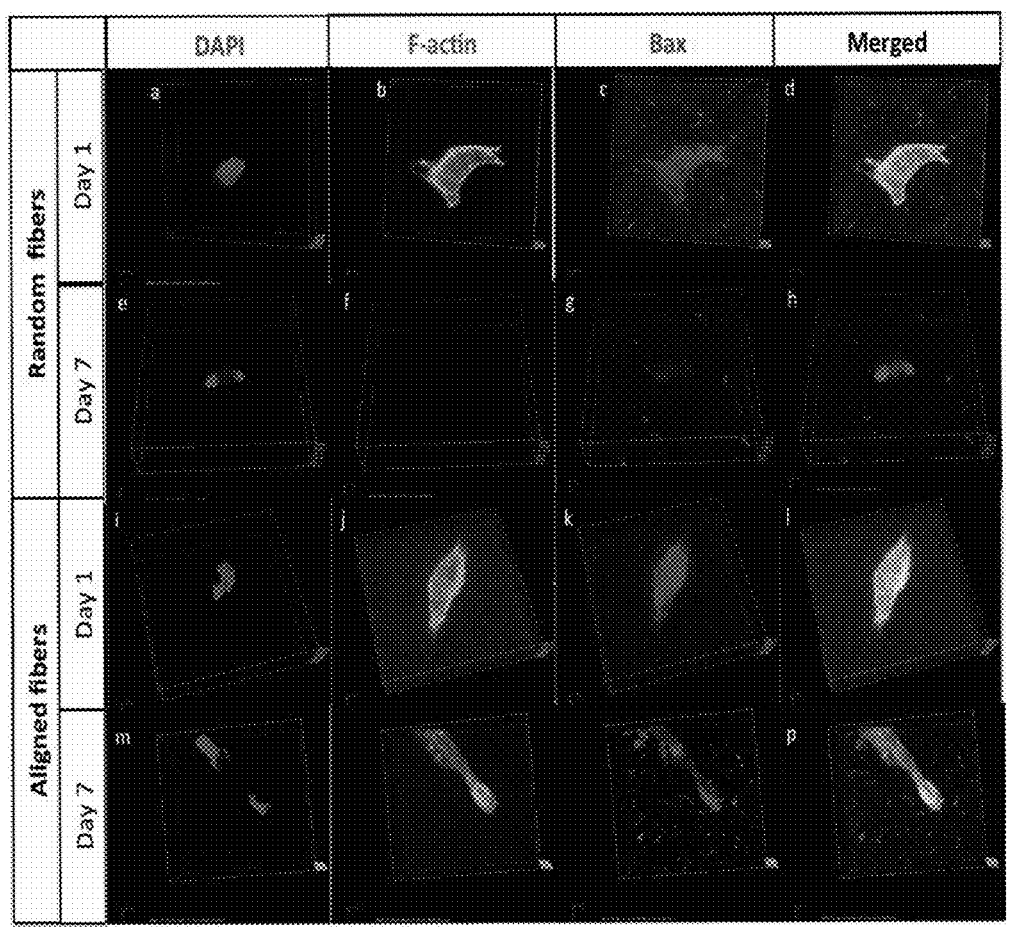
FIG. 27 shows Confocal fluorescent microscope images of Bax protein expression of treated MDA-MB-231 BCCs on the PCL random and aligned fibrous scaffolds. Treated BCCs on random scaffolds (a through d at day 1; e through h at day 7) and aligned scaffolds (i through l at day 1; m through p at day 7).

Results showed that, similar to TCP, non-treated MDA-MB-231 cells on random and aligned fibers stained for Bax at all time points (FIG. 25a-c; 26a-c). Similar to TCP, treated (dormant) MDA-MB-231 cells expressed Bax protein on scaffolds except on PCL random fibers at day 7 where there was not much expression. (FIG. 25a-c; 27a-c).

Figure 28:
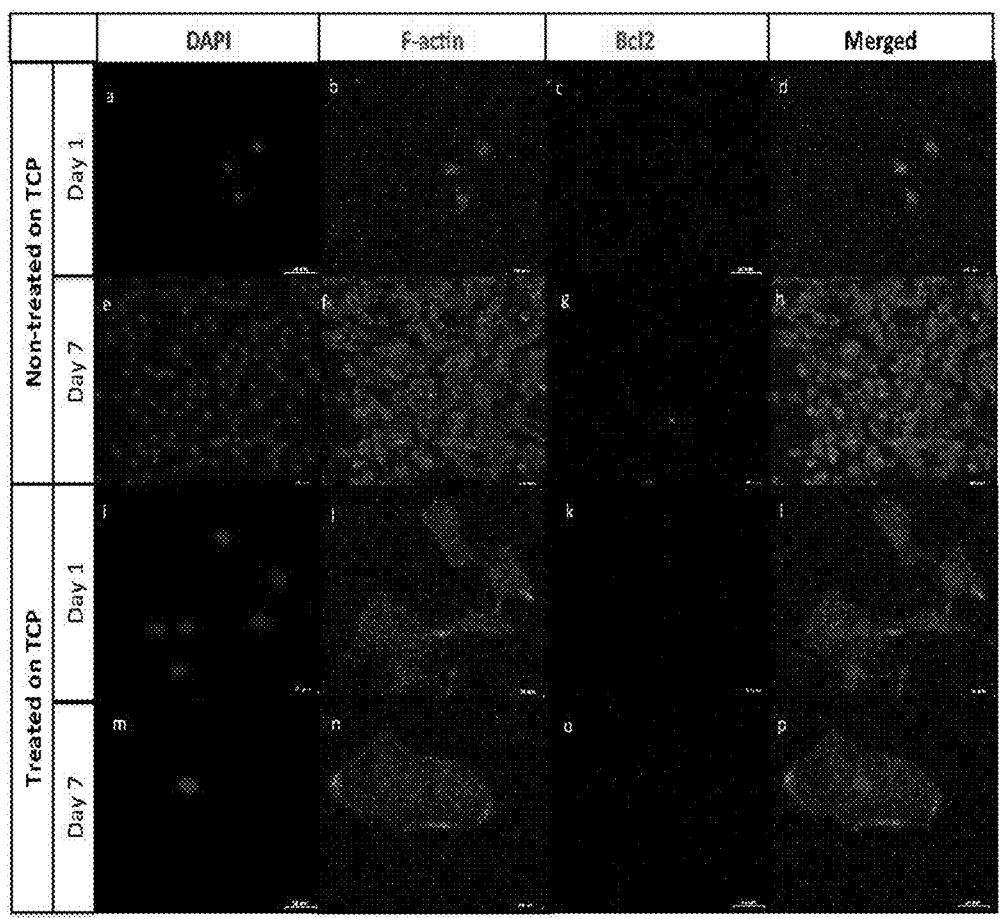
FIG. 28 shows Confocal fluorescent microscope images of Bcl2 protein expression of MDA-MB-231 BCCs on TCP control. Blue indicates nuclei (DAPI); green indicates F-actin (Alexa 488) and red is for anti-Bcl2 protein. Non-treated BCCs (a through d at day 1; e through h at day 7) and treated BCCs (i through l at day 1; m through p at day 7) on TCP.
Figure 29:
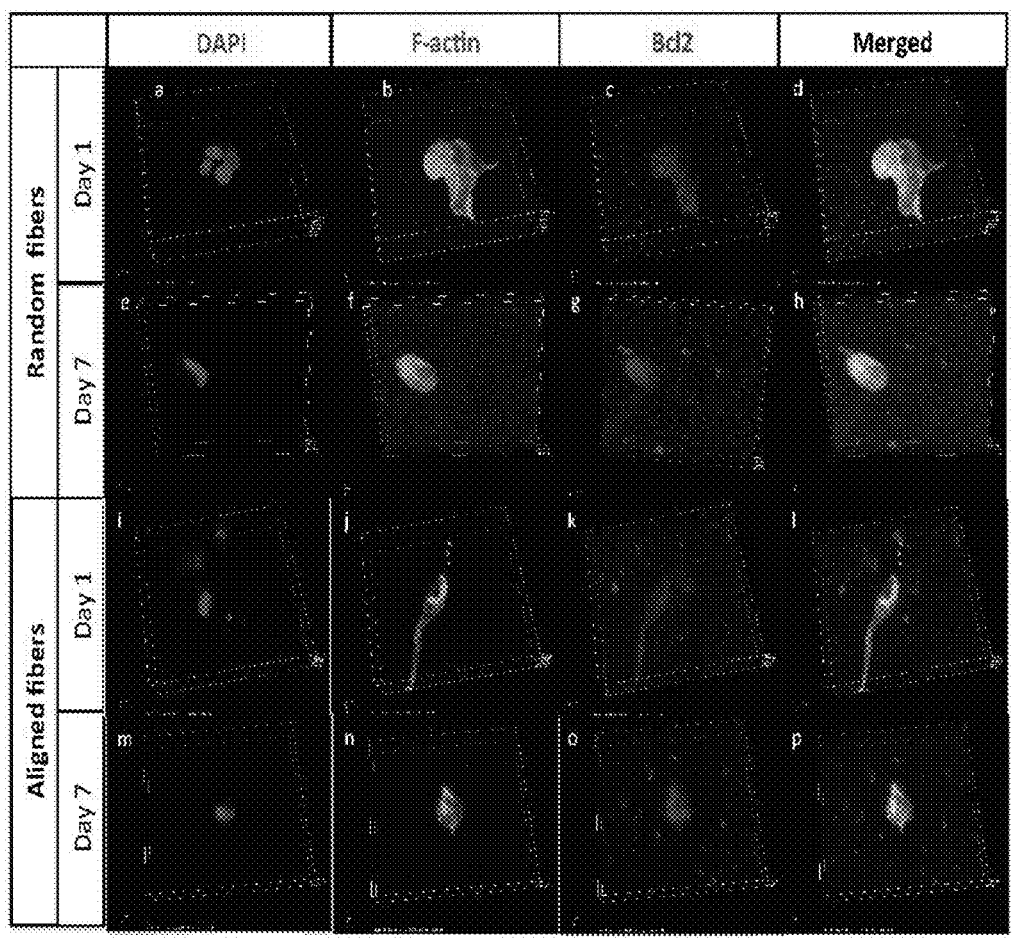
FIG. 29 shows Confocal fluorescent microscope images of Bcl2 protein expression of non-treated MDA-MB-231 BCCs on the PCL random and aligned fibrous scaffolds. Blue indicates nuclei (DAPI); green indicates F-actin (Alexa 488) and red is for anti-Bcl2 protein. Non-treated BCCs on random scaffolds (a through d at day 1; e through h at day 7) and aligned scaffolds (i through l at day 1; m through p at day 7).
Figure 30:
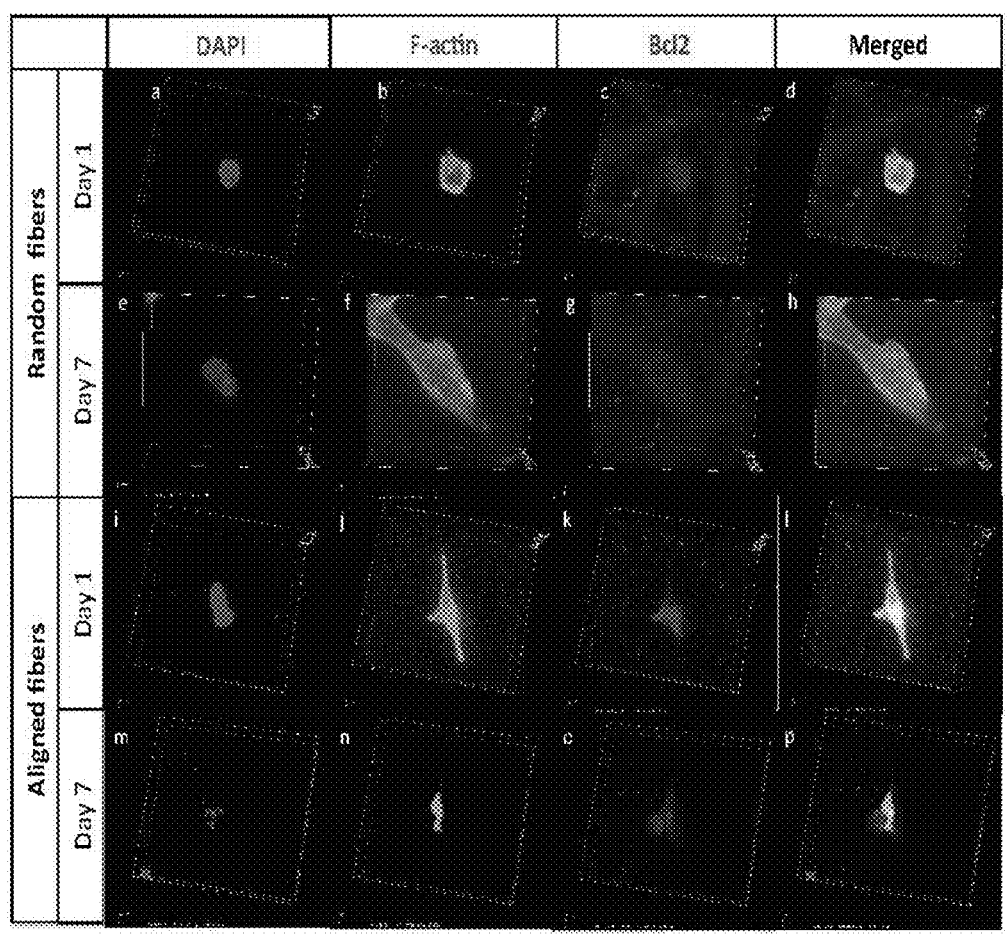
FIG. 30 shows Confocal fluorescent microscope images of Bcl2 protein expression of treated MDA-MB-231 BCCs on the PCL random and aligned fibrous scaffolds. Blue indicates nuclei (DAPI); green indicates F-actin (Alexa 488) and red is for anti-Bcl2 protein. Treated BCCs on random scaffolds (a through d at day 1; e through h at day 7) and aligned scaffolds (i through l at day 1; m through p at day 7).

Both non-treated and treated (dormant) cells expressed Bcl2 on all scaffolds at all time points, unlike both cell types on TCP at all time points (FIG. 28a-c; 29a-c; 30a-c).

Figure 31:
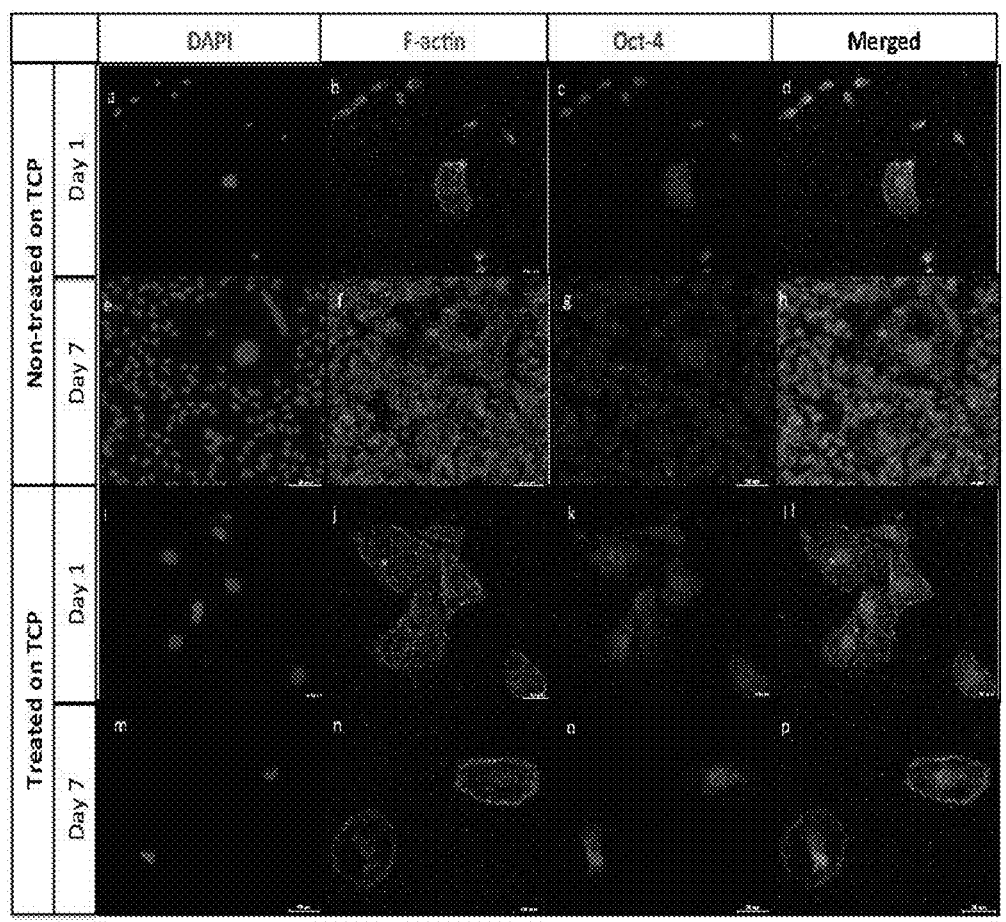
FIG. 31 shows Confocal fluorescent microscope images of Oct-4 protein expression of MDA-MB-231 BCCs on TCP control. Blue indicates nuclei (DAPI); green indicates F-actin (Alexa 488) and red is for anti-Oct-4. Non-treated BCCs (a through d at day 1; e through h at day 7) and treated BCCs (i through l at day 1; m through p at day 7) on TCP.
Figure 32:
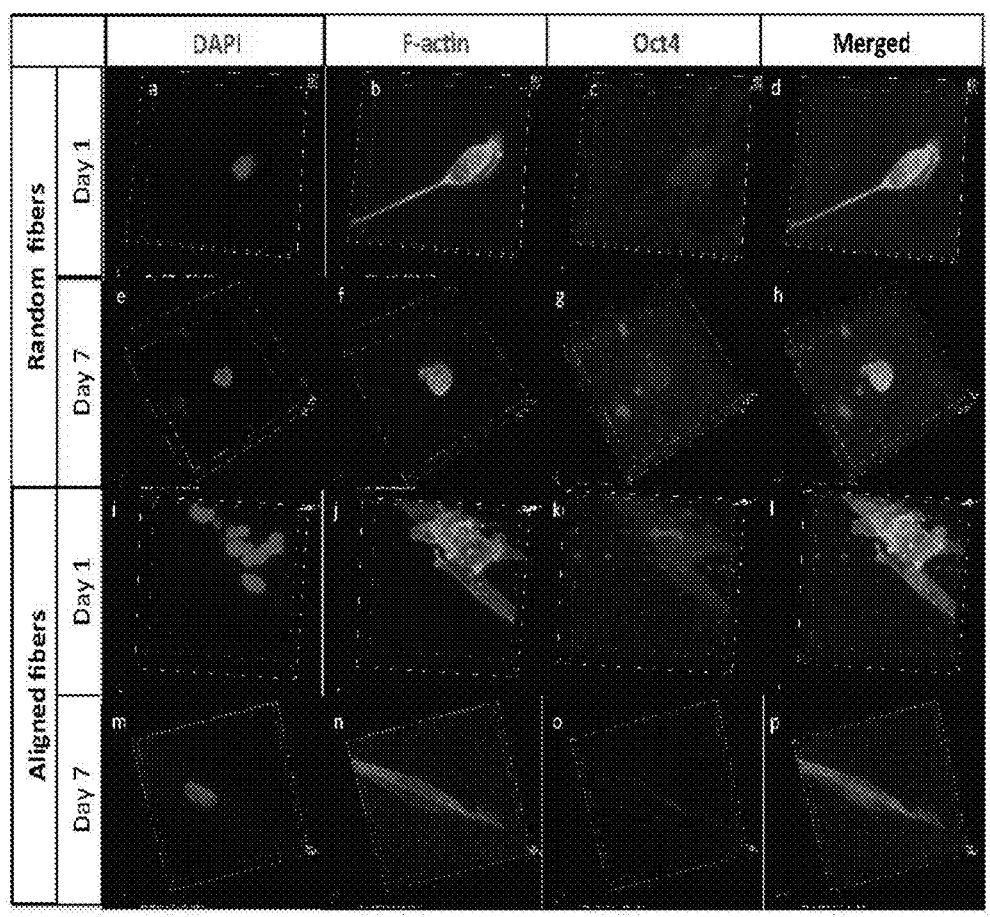
FIG. 32 shows Confocal fluorescent microscope images of Oct-4 protein expression of non-treated MDA-MB-231 BCCs on the PCL random and aligned fibrous scaffolds. Blue indicates nuclei (DAPI); green indicates F-actin (Alexa 488) and red is for anti-Oct-4. Non-treated BCCs on random scaffolds (a through d at day 1; e through h at day 7) and aligned scaffolds (i through l at day 1; m through p at day 7).
Figure 33:
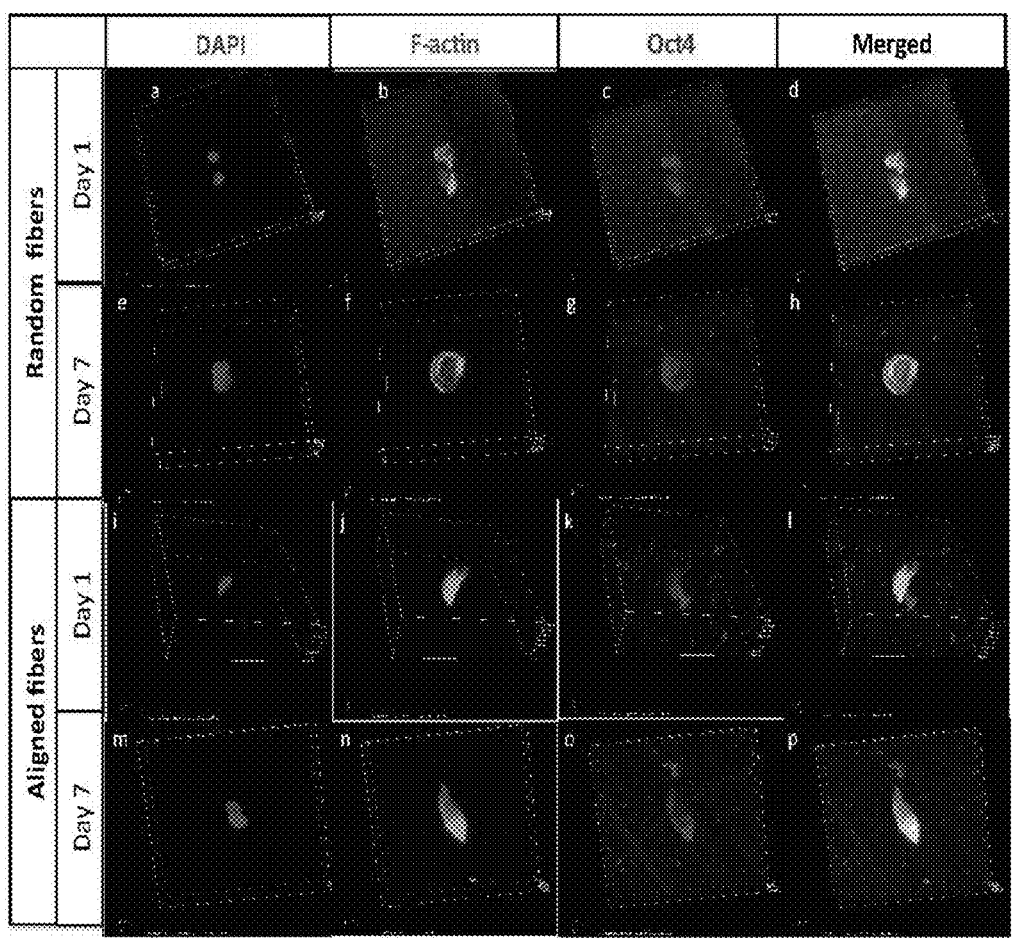
FIG. 33 shows Confocal fluorescent microscope images of Oct-4 protein expression of treated MDA-MB-231 BCCs on the PCL random and aligned fibrous scaffolds. Blue indicates nuclei (DAPI); green indicates F-actin (Alexa 488) and red is for anti-Oct-4. B) Treated BCCs on random scaffolds (a through d at day 1; e through h at day 7) and aligned scaffolds (i through l at day 1; m through p at day 7).

Non-treated cells expressed Oct-4 on all scaffolds at all time points. Treated (dormant) cells expressed Oct-4 on random fibers at all time points. On aligned fibers, treated (dormant) cells expressed Oct-4 at day 1 but at day 7, the immunostaining was weak/diminished for Oct-4 (FIG. 31a-c; 32a-c; 33a-c).

Sox2 was highly expressed by non-treated and treated (dormant) cells on all scaffolds at all time points (FIG. 34a-c; 35a-c; 36a-c).

Cell Migration: Live Cell Microscopy

Figure 37:
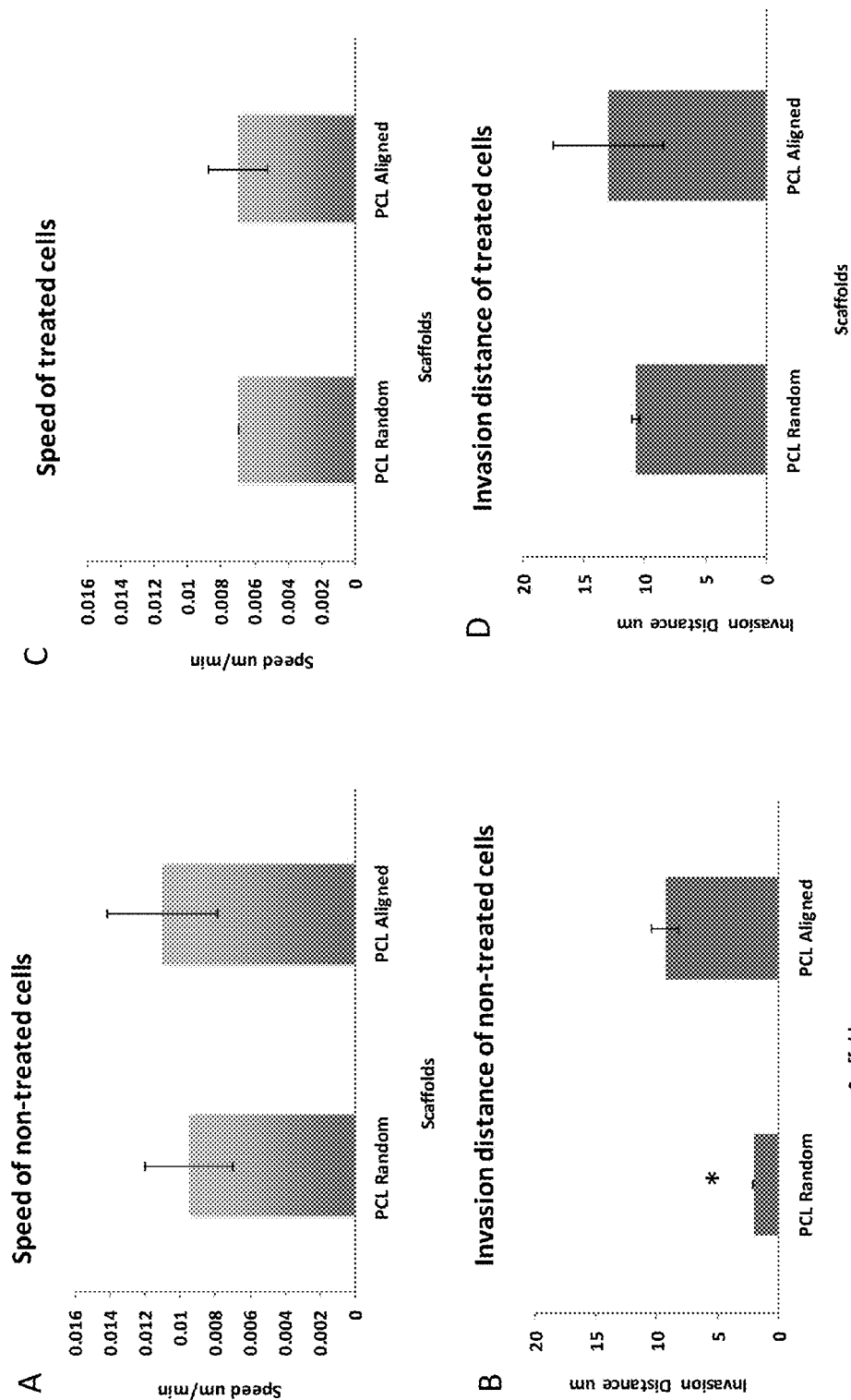
FIG. 37 shows Migration of non-treated and treated MDA-MB-231 on PCL scaffolds. A) Speed of non-treated cells on random and aligned fibers. B) Invasion distance of non-treated on random and aligned fibers. *$p<0.05$, significant difference between random and aligned fibers. C) Speed of treated cells on random and aligned. D) Invasion distance of treated cells on random and aligned fibers.

For the migration studies only non-treated and treated MDA-MB-231 cells were evaluated on scaffolds after 3 hours of culture. On PCL random fibers non-treated cells had a mean speed of 0.0095±0.002 μm/min (FIG. 37A) and a mean invasion distance of 2.09±0.02 μm (FIG. 37B). On PCL aligned fibers, non-treated cells had a mean speed of 0.011 μm/min±0.003 (FIG. 37C) and a mean invasion distance of 9.306±1.1 μm/min (FIG. 37D). There was no significant difference in migration speed on scaffolds. There was a significant difference in invasion distance between non-treated cells on random and aligned fibers.

Treated cells had a mean speed of 0.007 μm/min (FIG. 37C) and a mean invasion distance of 10.7±0.3 μm (FIG. 37D) on PCL random fibers. On PCL aligned fibers, treated cells had a mean speed of 0.007 μm/min (FIG. 37C) and a mean invasion distance of 12.07 μm±4.5 (FIG. 37D). There was no significant difference in mean speed and mean invasion distance between treated cells on the different scaffolds.

Carboplatin Treatment of Breast Cancer Cells

Figure 38:
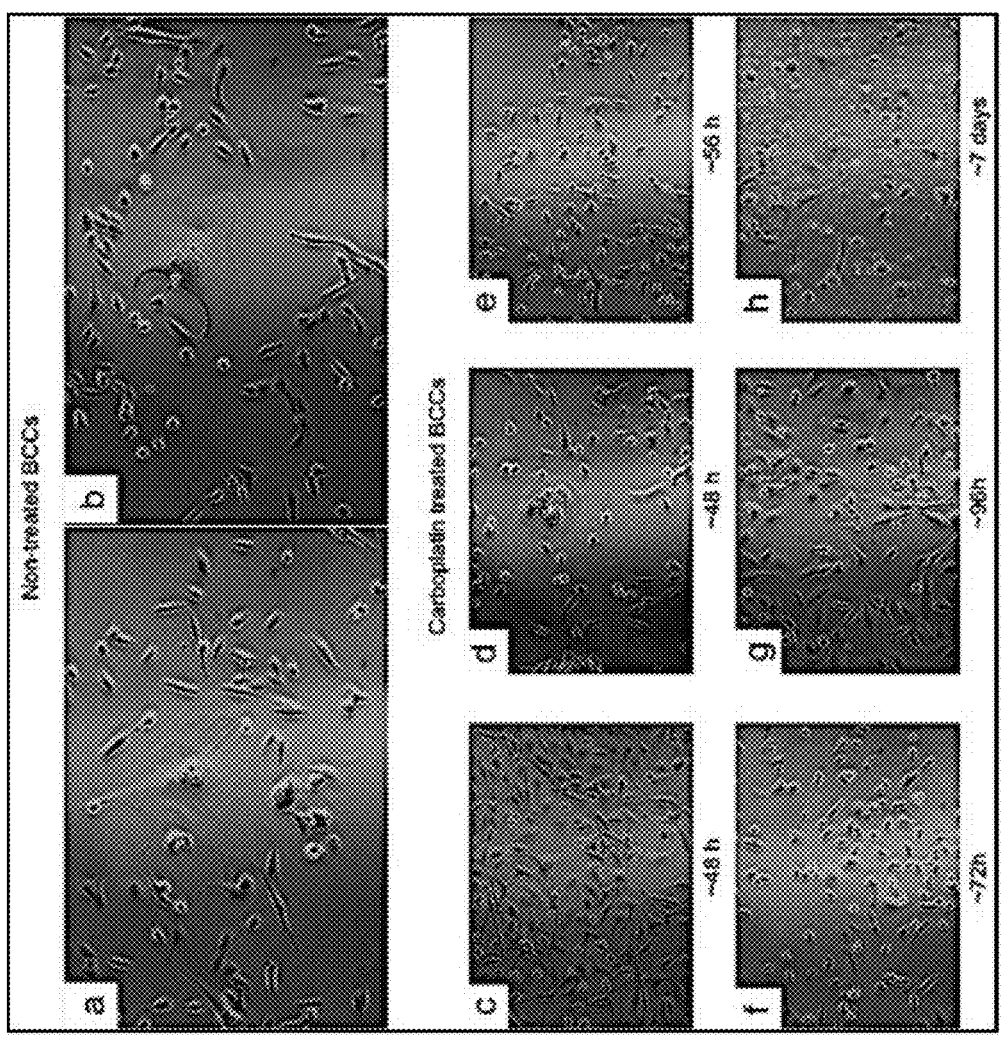
FIG. 38 shows Morphology of non-treated and treated MDA-MB-231 cells at several time points before seeding on scaffolds. Non-treated a) and b) pre-addition of carboplatin to culture media; c) and d) 48 h post-addition of carboplatin to culture media; e) 56 h post carboplatin addition; 72 h post addition of carboplatin; 96 h post addition of carboplatin; and h) 7 days post addition of carboplatin.

BCSCs have been shown to resist chemotherapy thus to isolate these CSCs from the heterogeneous non-treated population of BCCs, MDA-MB-231 cells were treated with carboplatin, a chemotherapy drug, and chemo-resistant (treated) BCCs were identified by cell viability and characterized for stem cell markers. For these studies carboplatin sensitivity of MDA-MB-231 cells was investigated as previously mentioned. Different subpopulations were obtained for subsequent studies on scaffolds. Under normal condition, BCCs population in culture can be seen to be composed of a heterogeneous population of giant multi-nucleated cells mixed with small single-nucleated cells (FIGS. 38a and b.). However, several hours post treatment with carboplatin, giant multi-nucleated cells were no longer present and only small single-nucleated cells were remaining (FIG. 38c-g). At longer time points, such as 7 days post carboplatin treatment, the MDA-MB-231 cells were fragmented and appeared to be dying (FIG. 38h). Therefore, cells at 3-4 days post treatment were selected as being carboplatin resistant MDA-MB-231 cells. In the previous chapter, we have shown these highly chemoresistant MDA-MB-231 cells possess stemness properties; self-renewal and anti-apoptotic properties and additionally, they expressed key breast cancer stem cell markers as well.

Morphology of BCCs on Scaffolds

Morphology and interaction between non-treated and treated MDA-MB-231 cells on TCP and scaffold fibers were analyzed in vitro for 7 days.

Figure 39:
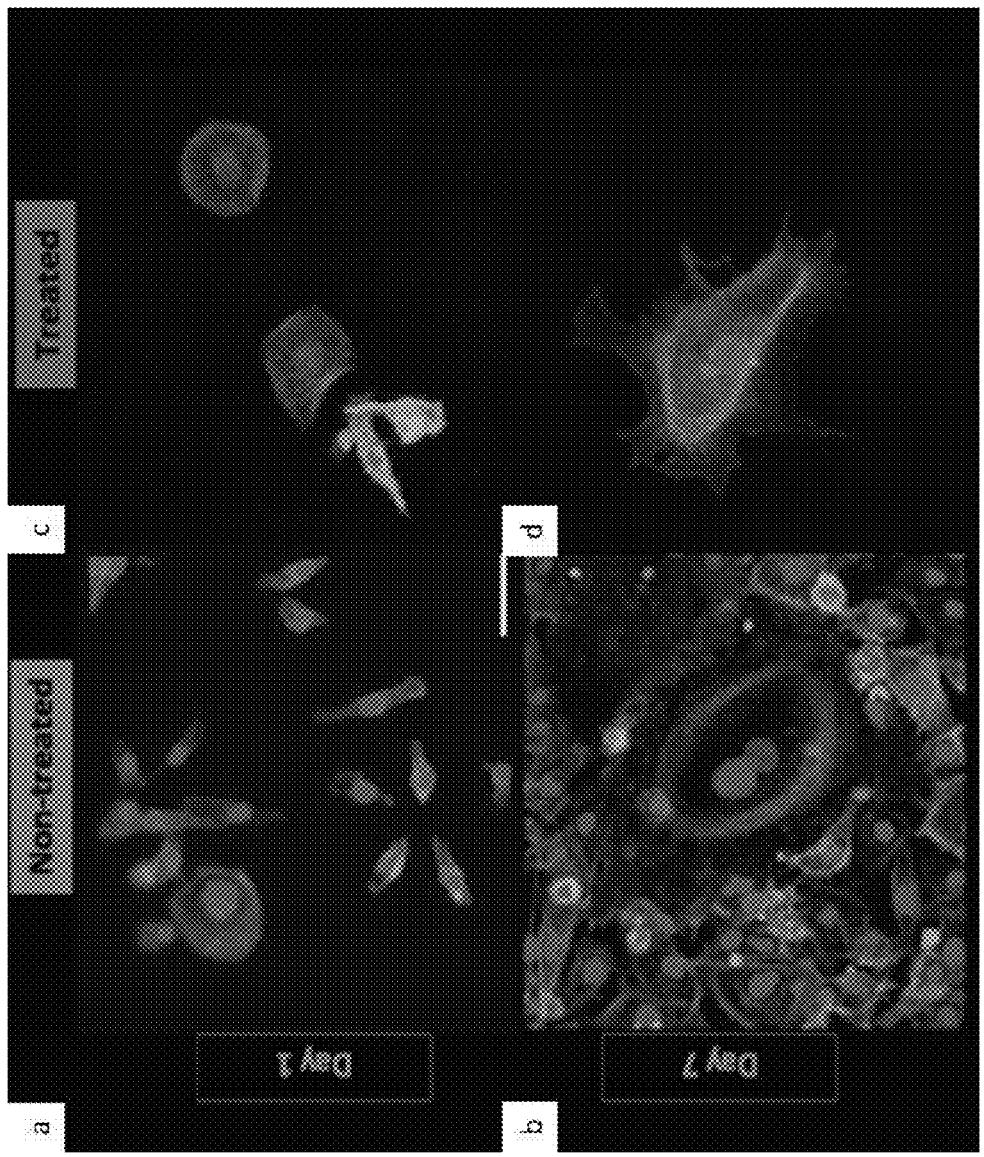
FIG. 39 shows Confocal fluorescent microscope images of MDA-MB-231 cells on TCP control. Blue, Dapi nuclear stain and green indicates F-actin (Alexa 488) with non-treated cells at a) day 1 and b) day 7, and treated cells at e) day 1 and f) day 7. 60× objective. Scale bar is 25 µm

On TCP, non-treated MDA-MB-231 cells displayed confluency by day 7 (FIGS. 39a and b) with some non-treated MDA-MB-231 cells characterized with spread and spindle-like shapes. On TCP, MDA-MB-231 treated cells appeared to be well attached to the substrate with a spread out morphology (FIGS. 39c and d).

On scaffolds, volume views of cells in the 3-D-reconstructed Z-stack images showed that both non-treated and treated MDA-MB-231 cells were able to be located within different layers (stacks) within the fibrous scaffolds. Both non-treated and treated MDA-MB-231 cells cultured on the 3-D scaffold showed changes in cell morphology and adherence (FIGS. 41 and 42).

Figure 40:
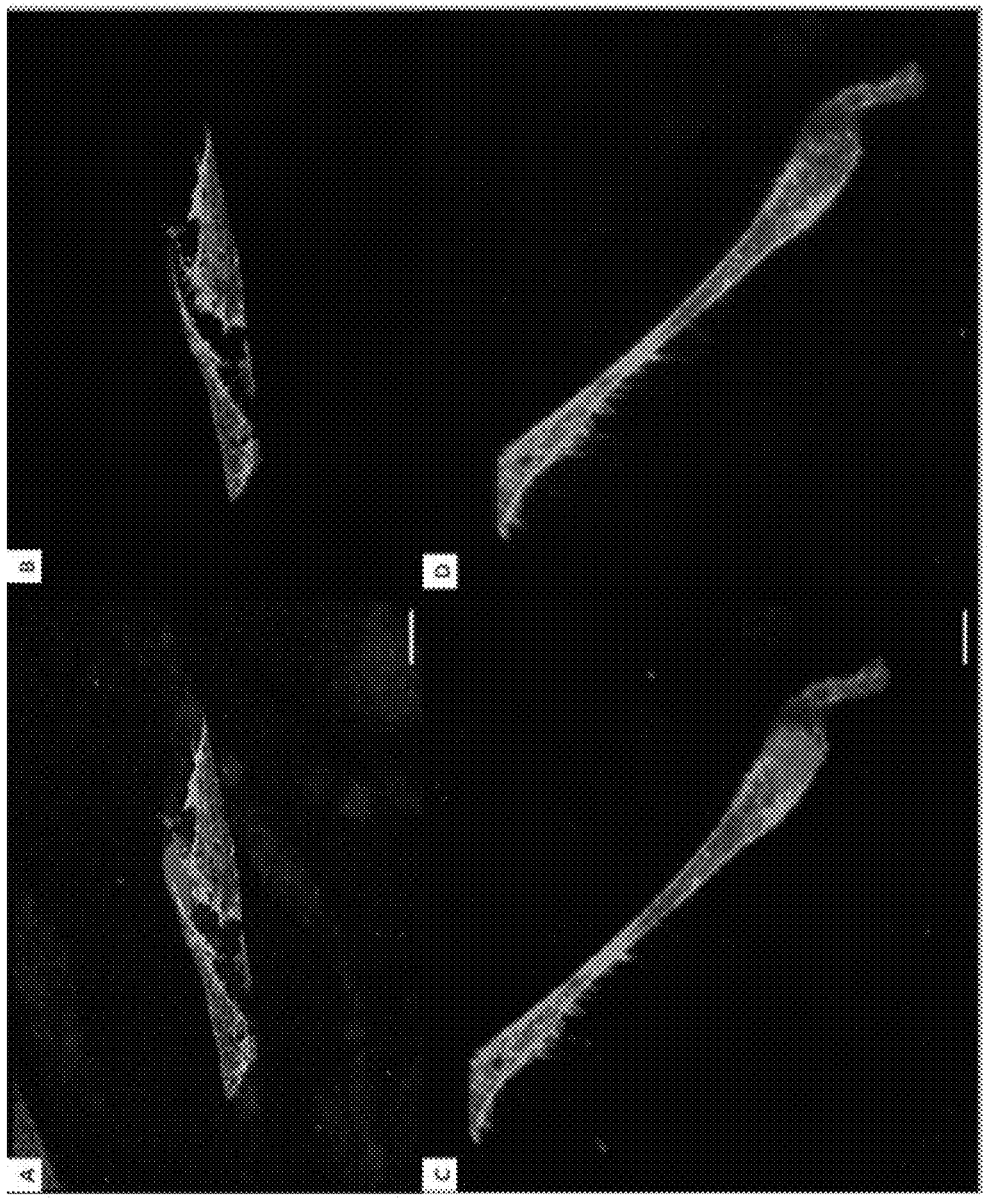
FIG. 40 shows Morphology of treated BCCs on PCL+HA scaffolds a) and b) at day 1 and c) and d) at day 7. DAPI nuclear stain is in blue, and green indicates F-actin (Alexa 488). All scale bars are 50 µm.
Figure 41:
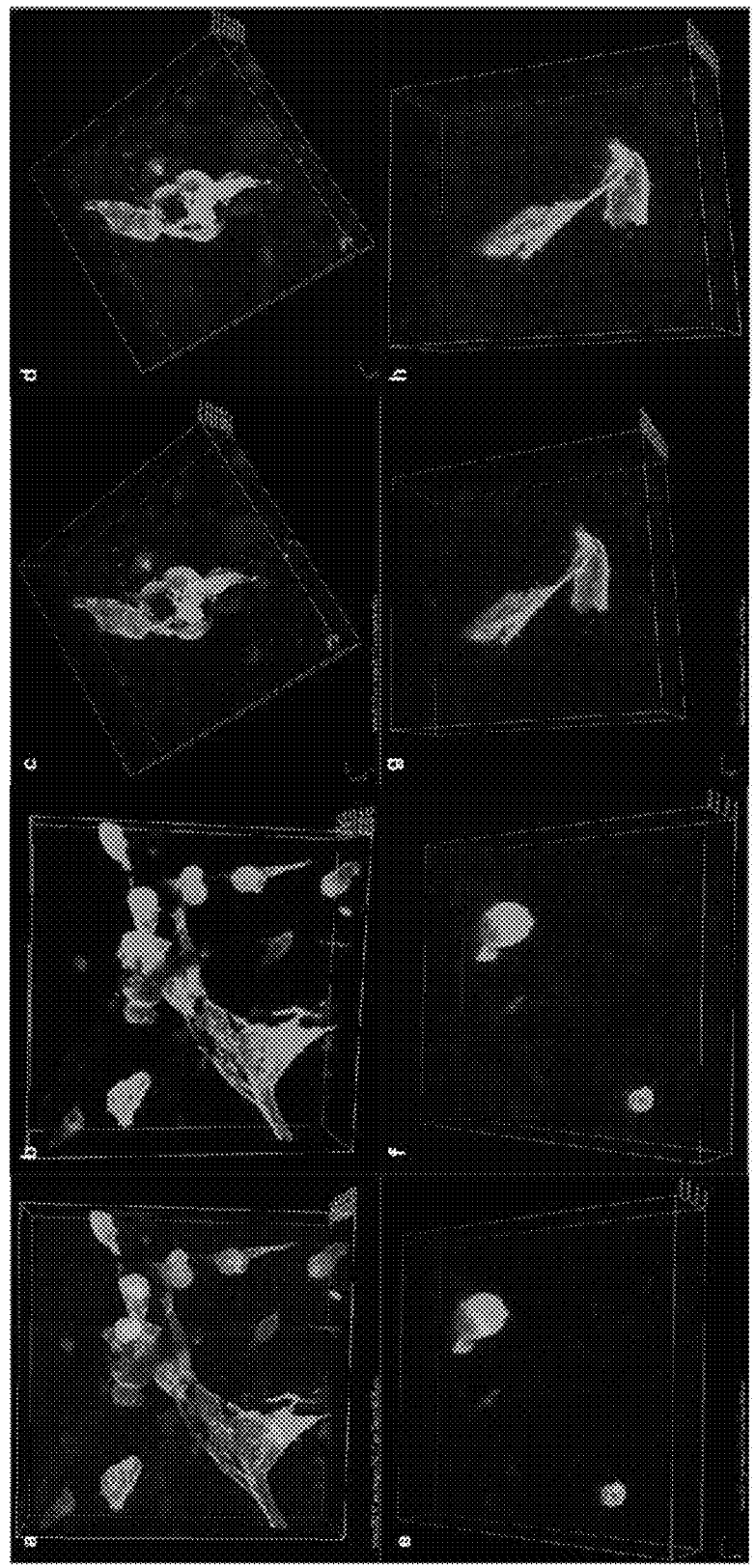
FIG. 41 shows Confocal fluorescent microscope images of MDA-MB-231 BCCs on the PCL+HA random fibrous scaffolds. Blue indicates nuclei (DAPI); green indicates F-actin (Alexa 488). A) a) Merged and b) F-actin non-treated BCCs at day 1 and c) merged and F-actin d) treated BCCs at day 1; e) Merged and f) F-actin non-treated BCCs at day 7 and g) merged and F-actin h) treated BCCs at day 7. All scale bars are 50 µm.
Figure 42:
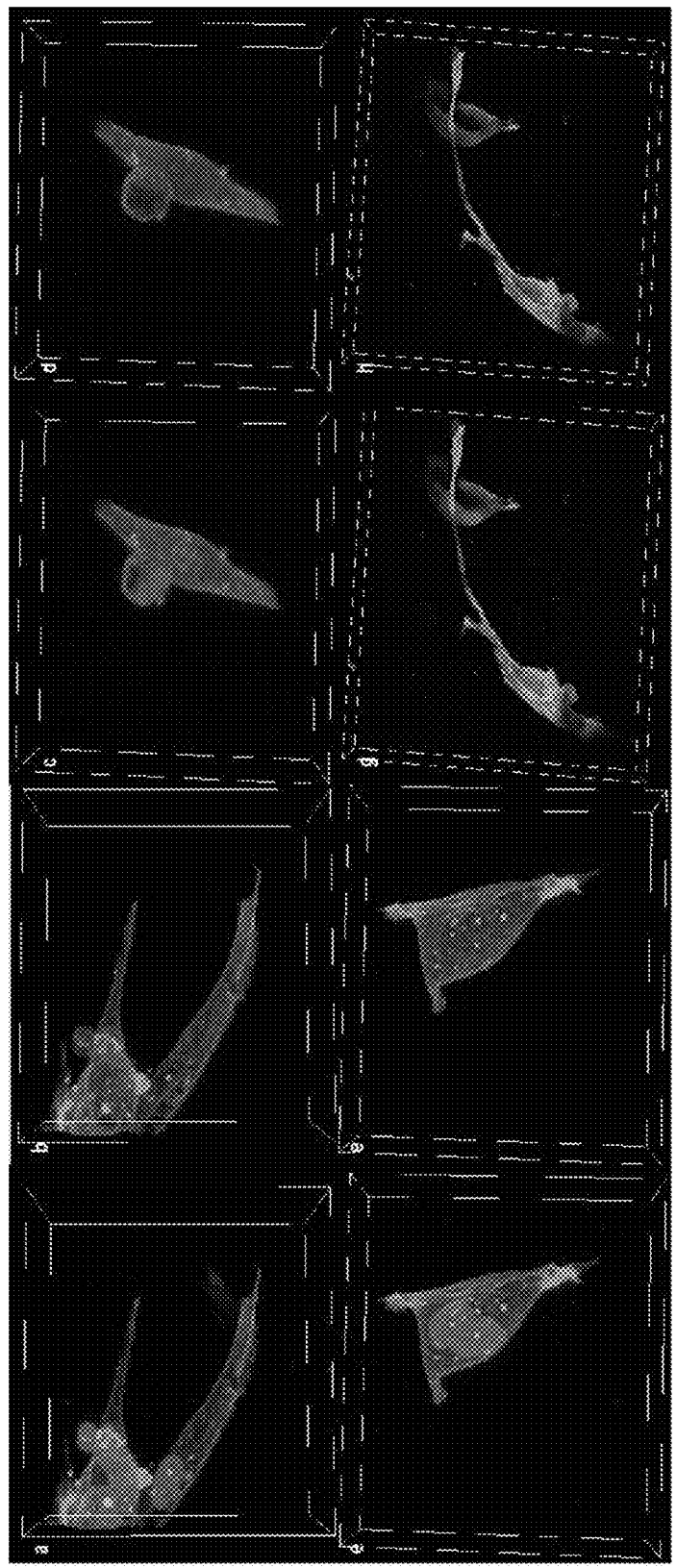
FIG. 42 shows Confocal fluorescent microscope images of MDA-MB-231 BCCs on the PCL+HA aligned fibrous scaffolds. Blue indicates nuclei (DAPI); green indicates F-actin (Alexa 488). A) a) Merged and b) F-actin non-treated BCCs at day 1 and c) merged and F-actin d) treated BCCs at day 1; e) Merged and f) F-actin non-treated BCCs at day 7 and g) merged and F-actin h) treated BCCs at day 7. All scale bars are 50 µm

On PCL+HA random fibers, non-treated MDA-MB-231 cells had a mesenchymal phenotype at day 1 (FIGS. 41a and b) which appeared to be more spread or elongated along the fibrous structures of the scaffolds and a more rounded shape by day 7 (FIGS. 41e and f). On PCL+HA aligned fibers, non-treated MDA-MB-231 cells had a mesenchymal phenotype at day 1 (FIGS. 42a and b) which appeared to be more elongated along the fibrous structures of the scaffolds. At day 7 non-treated cells still appeared to have a mesenchymal phenotype and appeared to be well attached to the fibers of the scaffolds (FIGS. 42e and f). Treated MDA-MB-231 cells on PCL+HA random fibers had a morphology that was spread on both day 1 (FIGS. 41c and d) and day 7 (FIGS. 41.g and h) with cell bodies stretched along the fibers. Treated cells appeared to interact well with the fibrous scaffolds and this is depicted in a representative FIG. 40 where treated cells enveloped a fiber (FIGS. 40a. and b). At day 7, treated cells displayed elongated cytoskeletal structures showing filaments similar to cells with lamellipodia, which are usually found on very mobile cells (FIGS. 40c. and d.). On PCL+HA aligned fibers, treated MDA-MB-231 cells had a morphology that was elongated and spindled like on both day 1 (FIGS. 42.c and d) and day 7 (FIGS. 42g and h) with cell bodies stretched along the fibers. At day 7, treated cells displayed elongated cytoskeletal structures showing filaments similar to cells with lamellipodia, which are usually found on very mobile cells (FIGS. 42g. and h.).

Cell Proliferation

Figure 43:
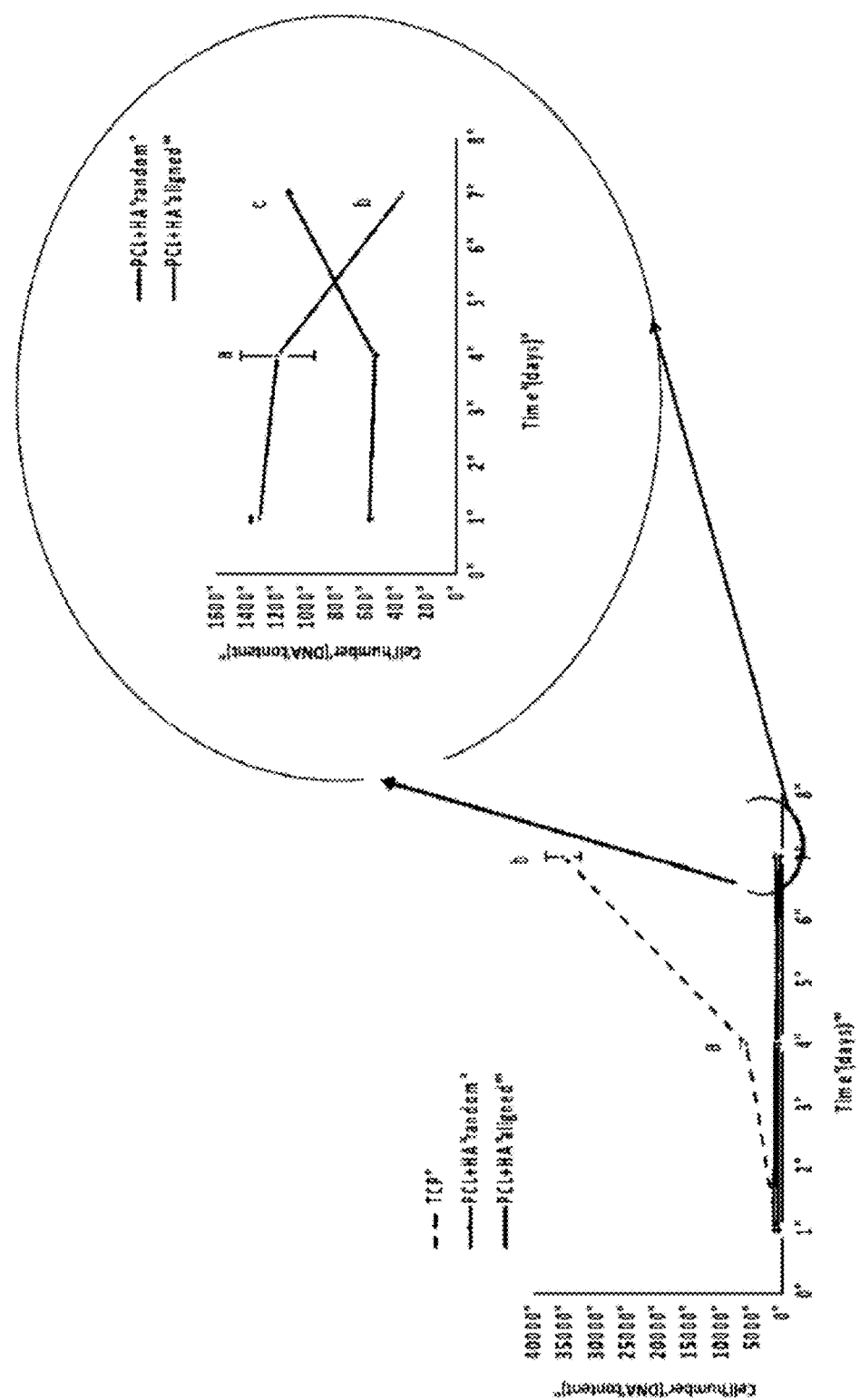
FIG. 43 shows Growth of non-treated MDA-MB-231 cells on PCL+HA random and PCL+HA aligned fibrous scaffolds in comparison to TCP. a) TCP. $^a$ $p<0.05$, significant increase in growth of non-treated MDA-MB-231 cells at day 4 as compared to day 1. $^b$ $p<0.05$, significant increase in growth of non-treated cells at day 7 as compared to days 1 and 4. b) PCL+HA random and aligned fibers. $^a$ $p<0.05$, significant decrease in growth between day 4 and day 7 of non-treated cells on PCL+HA aligned. $^b$ p<0.05, significant decrease in growth between day 7 and day 1 of non-treated cells on PCL+HA aligned. $^c$ p<0.05, significant increase in growth between days 1 and 4 and day 7 of non-treated cells on PCL+HA random.

On TCP, non-treated MDA-MB-231 cells displayed significant increase in cell number at days 4 and 7 as compared to day 1 ($p<0.05$) (FIG. 43a.). Non-treated MDA-MB-231 cells showed a slight increase in cell growth at day 7 ($p<0.05$) on PCL+HA random fibrous scaffolds (FIG. 43b.). On PCL+HA aligned fibrous scaffolds, non-treated MDA-MB-231 cells showed a significant decrease in growth at day 7 ($p<0.05$) (FIG. 43b.).

Figure 44:
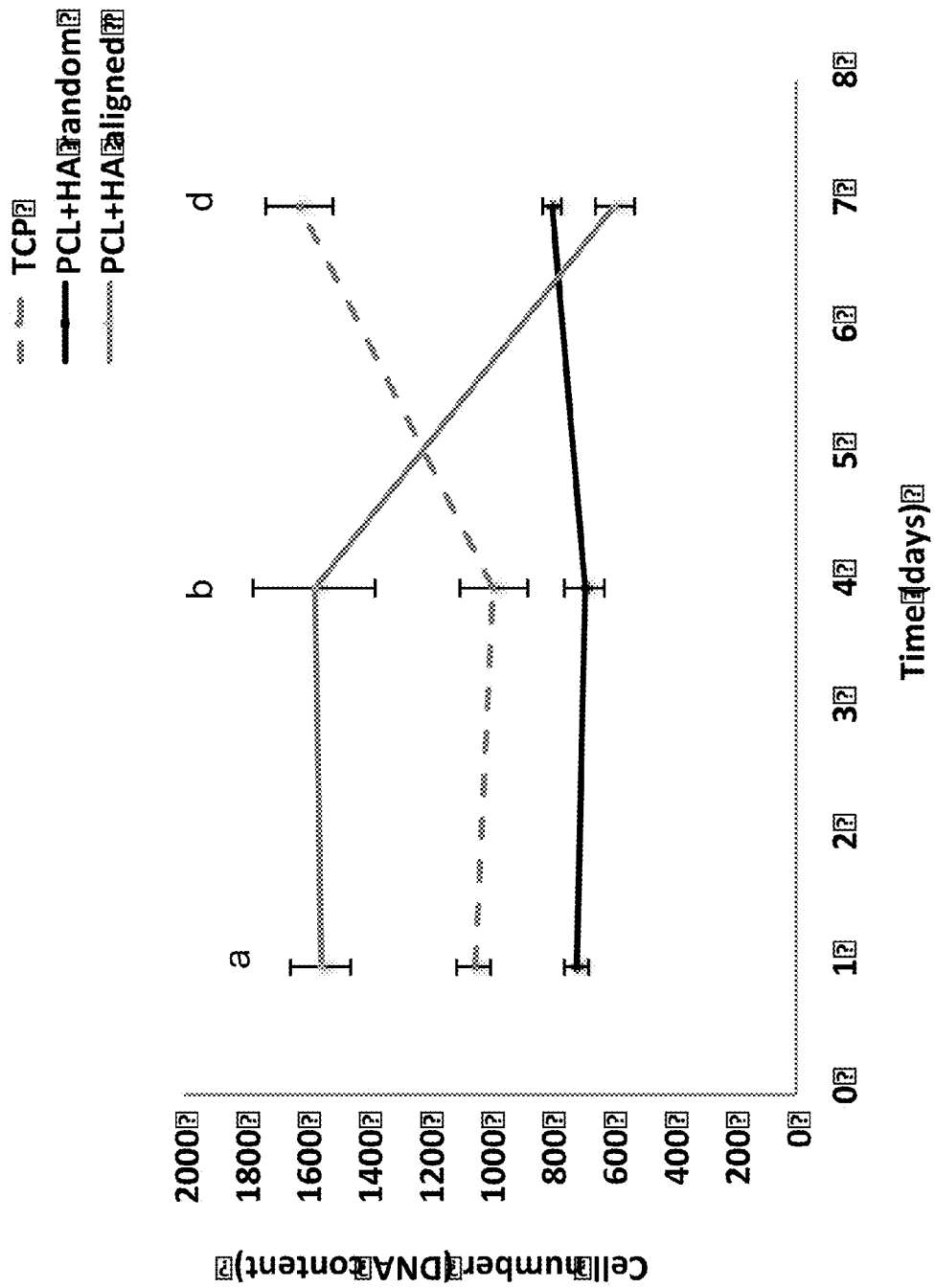
FIG. 44 shows Growth of treated MDA-MB-231 cells on PCL+HA random and PCL+HA aligned fibrous scaffolds in comparison to TCP. a p<0.05, significant decrease in growth between day 1 and day 7 on PCL+HA aligned fibers. b p<0.05, significant decrease in growth between day 4 and day 7 on PCL+HA aligned fibers. c p<0.05, significant increase in growth at d

Treated BCCs on TCP, showed a significant increase at day 7 ($p<0.05$) as compared to days 1 and 4; while no difference in cell number were detected over time for treated MDA-MB-231 cells on PCL+HA random fibrous scaffolds (FIG. 44).

Metabolic Activity

Figure 45:
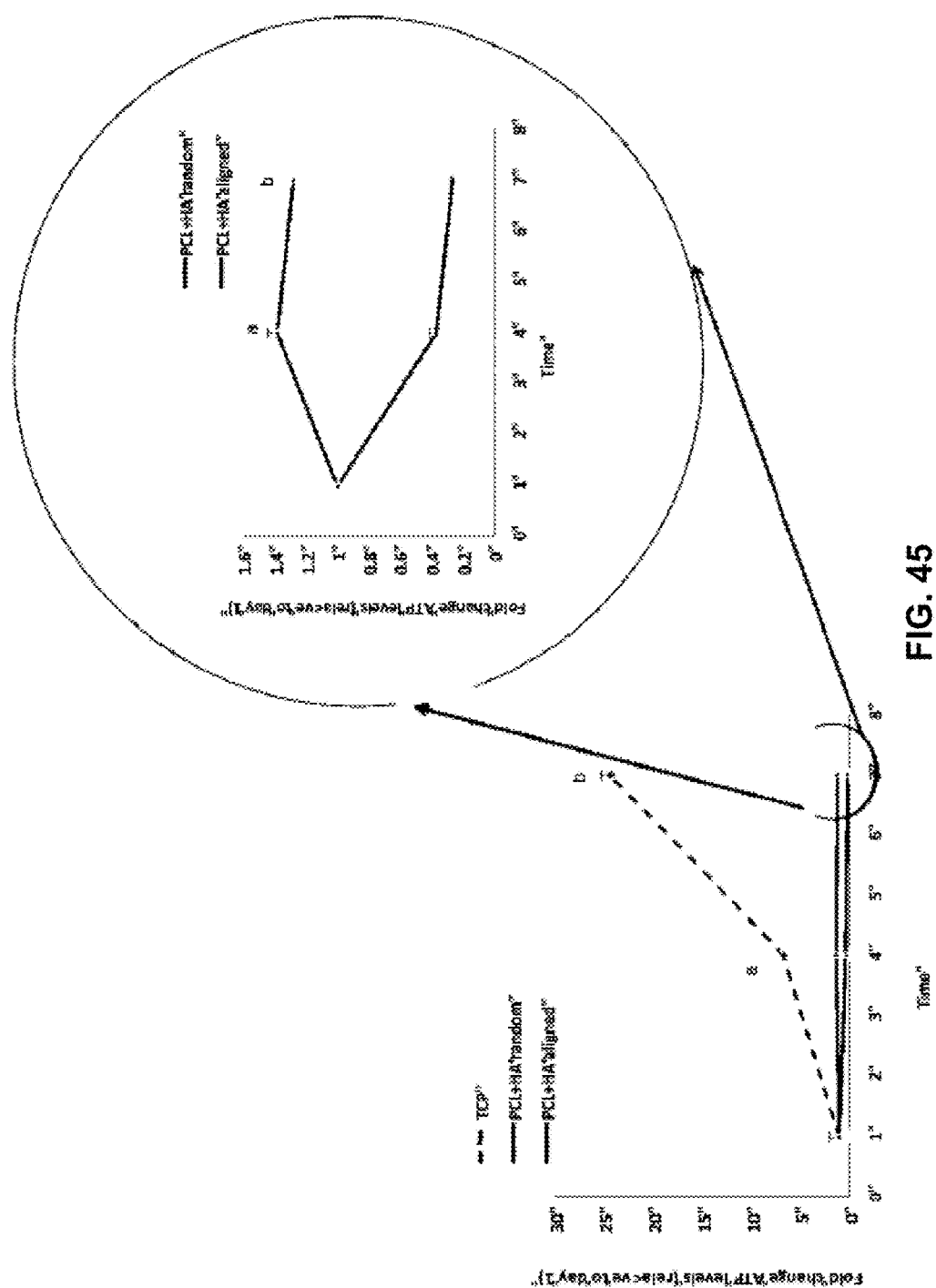
FIG. 45 shows Metabolic activity of MDA-MB-231 cells on PCL+HA fibrous scaffolds in comparison to TCP. a) TCP. $^{a,b}$ p<0.05, significant increase in metabolically active non-treated MDA-MB-231 cells at day 4 and day 7 as compared to day 1. b) PCL+HA random and aligned fibers. $^a$ p<0.05, significant increase in metabolic activity at day 4 as compared to day 1 of non-treated cells on PCL+HA aligned. $^b$ p<0.05, significant decrease in metabolic activity between days 1 and day 4 and 7 of non-treated cells on PCL+HA random.

On TCP, non-treated BCCs displayed a significant increase in metabolic activity ($p<0.05$) over time (~7 fold and ~25 fold increase as compared to day 1) (FIG. 45). On PCL+HA random and PCL+HA aligned fibrous scaffolds, non-treated MDA-MB-231 cells had significantly lower metabolic activity during the 7-day culture period as compared to TCP (FIGS. 45a.-b.).

Figure 46:
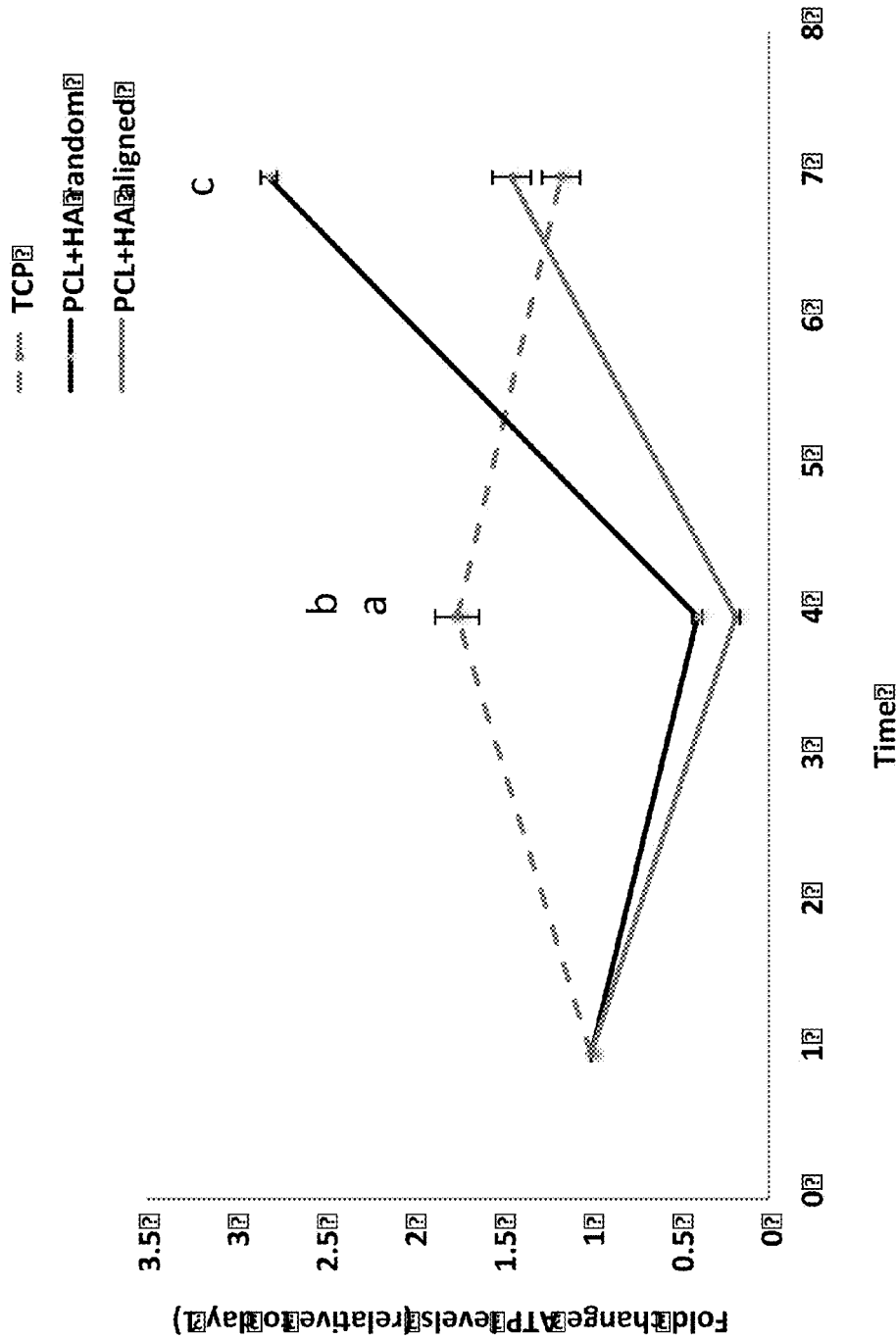
FIG. 46 shows Metabolic activity of treated MDA-MB-231 cells on PCL+HA random and aligned fibers in comparison to TCP. a p<0.05, significant increase in metabolic activity between day 1 and day 4 of treated cells on TCP. b p<0.05, significant decrease in metabolic activity of treated BCCs on PCL+HA random and aligned fibers in comparison to day 7. Values are mean±SD

On TCP, no differences in metabolic activity were detected for treated MDA-MB-231 cells over the 7-day culture period. On PCL+HA random fibrous scaffolds, treated MDA-MB-231 cells had a 2-fold ($p<0.05$) significant decrease in metabolic activity at day 4 as compared to day 1 (FIG. 43c.) followed by a significant increase (3 folds) in metabolic activity at day 7 ($p<0.05$). On PCL+HA aligned fibrous scaffolds, treated MDA-MB-231 cells had a ~2-fold ($p<0.05$) significant decrease in metabolic activity at day 4 as compared to day 1 (FIG. 46) followed by a significant increase in metabolic activity at day 7 ($p<0.05$).

Cyclin D1 Expression

Figure 47:
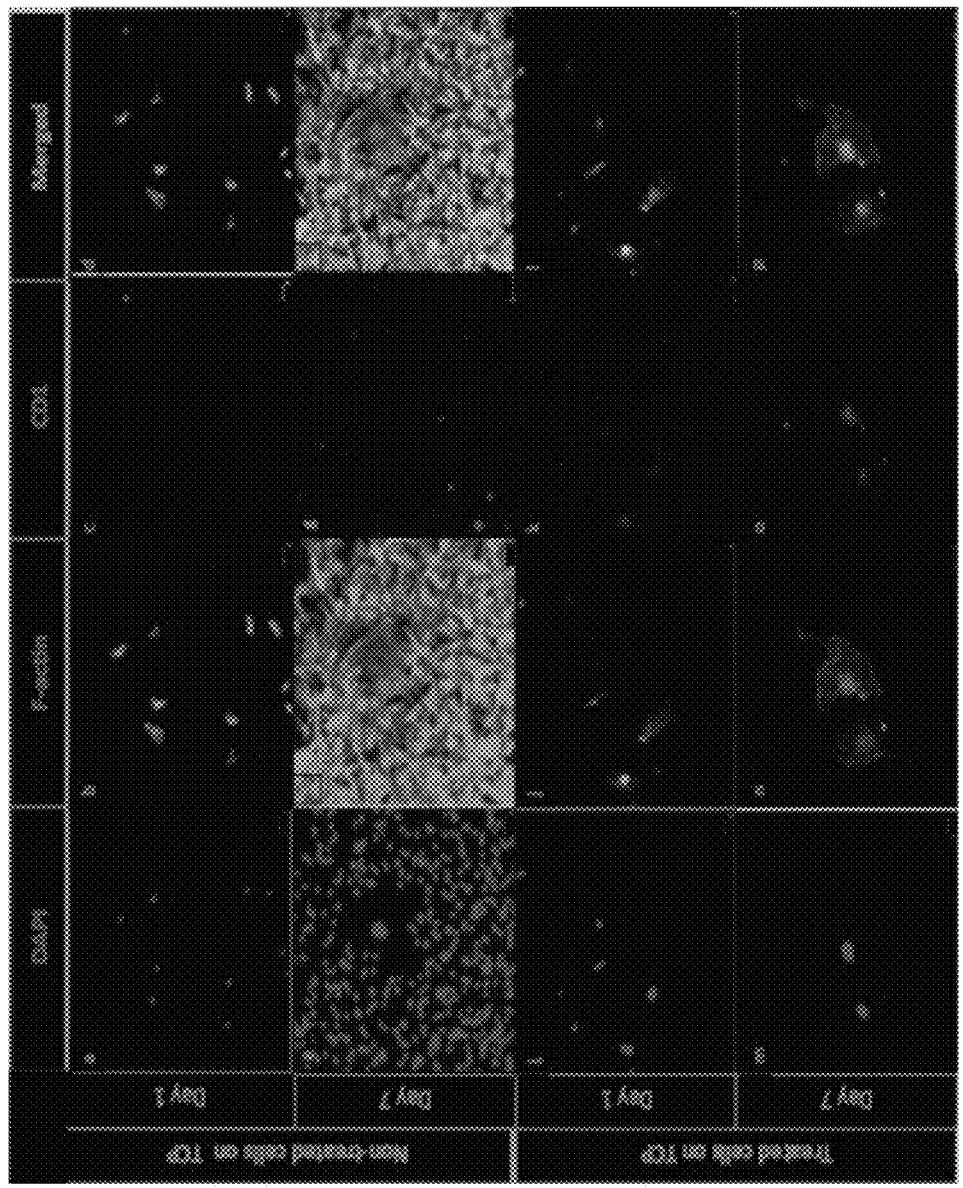
FIG. 47 shows Confocal microscopy of cyclin D1 expression of MDA-MB-231 BCCs on TCP. Non-treated cells at day 1 a-d and at day 7 e-h and treated cells at day 1 i-l and day 7 m-p. Blue is for Dapi, green for F-actin, and red for cyclin D1 expression
Figure 48:
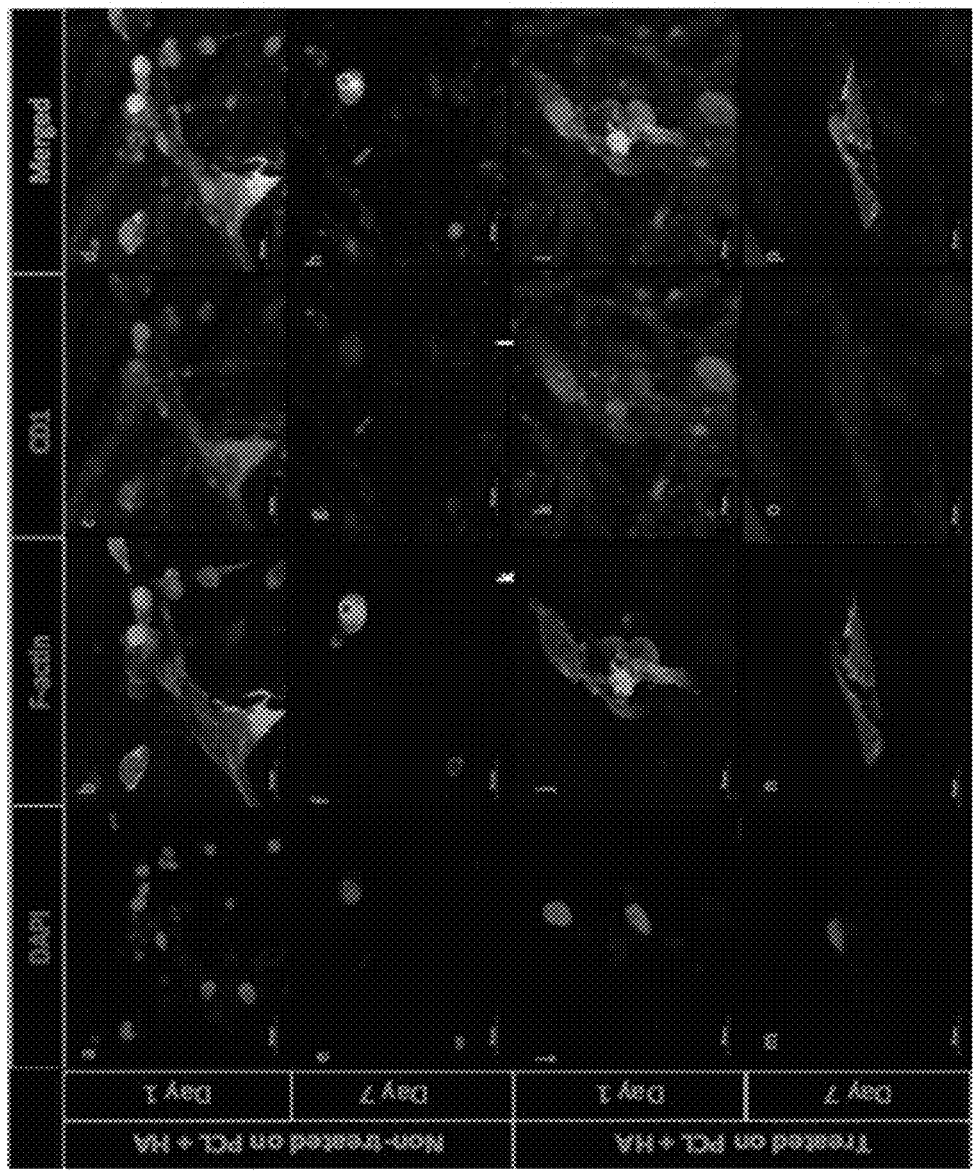
FIG. 48 shows Confocal microscopy of cyclin D1 expression of MDA-MB-231 BCCs on PCL+HA random scaffolds. Non-treated cells at day 1 a-d and at day 7 e-h and treated cells at day 1 i-l and day 7 m-p. Blue is for Dapi, green for F-actin, and red for cyclin D1 expression.
Figure 49:
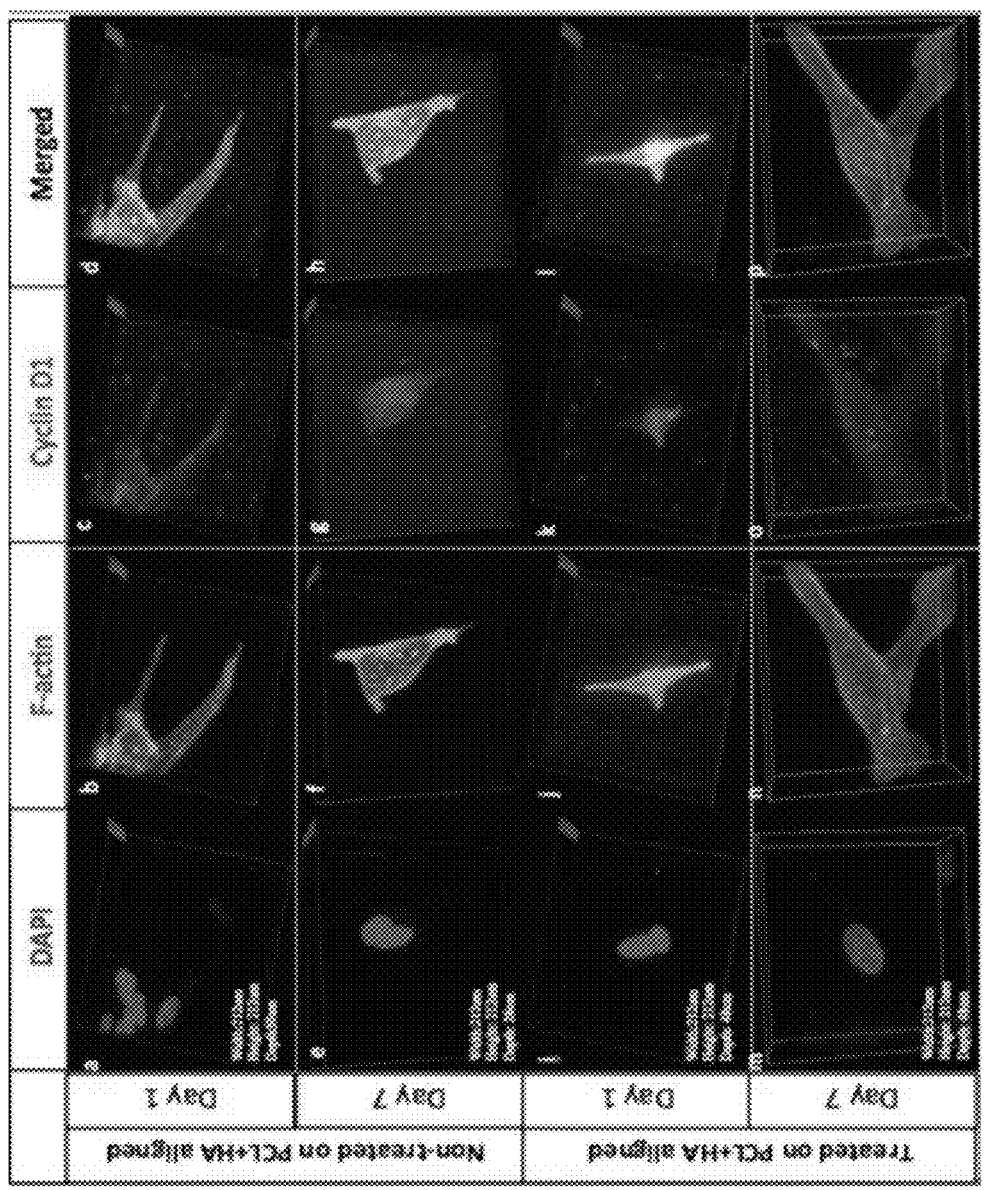
FIG. 49 shows Confocal microscopy of cyclin D1 expression of MDA-MB-231 BCCs on PCL+HA aligned scaffolds. Non-treated cells at day 1 a-d and at day 7 e-h and treated cells at day 1 i-l and day 7 m-p. Blue is for Dapi, green for F-actin, and red for cyclin D1 expression.

Non-treated MDA-MB-231 cells expressed little to no cyclin D1 Cyclin D1 on TCP at both days 1 and 7 (FIGS. 47.B c and g.). On PCL+HA random fibers non-treated MDA-MB-231 cells expressed cyclin D1 throughout the 7 days culture (FIGS. 48.A.c. and g.). On PCL+HA aligned fibers MDA-MB-231 cells expressed cyclin D1 at both days 1 and 7 (FIGS. 49.B c and g.). Treated MDA-MB-231 cells on TCP expressed cyclin D1 throughout the culture period (FIGS. 47.B. k and o.). On PCL+HA random fibers, treated BCCs expressed cyclin D1 throughout the 7 days culture period (FIGS. 48.A. k. and o.). On PCL+HA aligned fibers treated MDA-MB-231 expressed cyclin D1 at both days 1 and 7 (FIGS. 49.A. k. and o.).

Flow Cytometry Analyses

Figure 50:
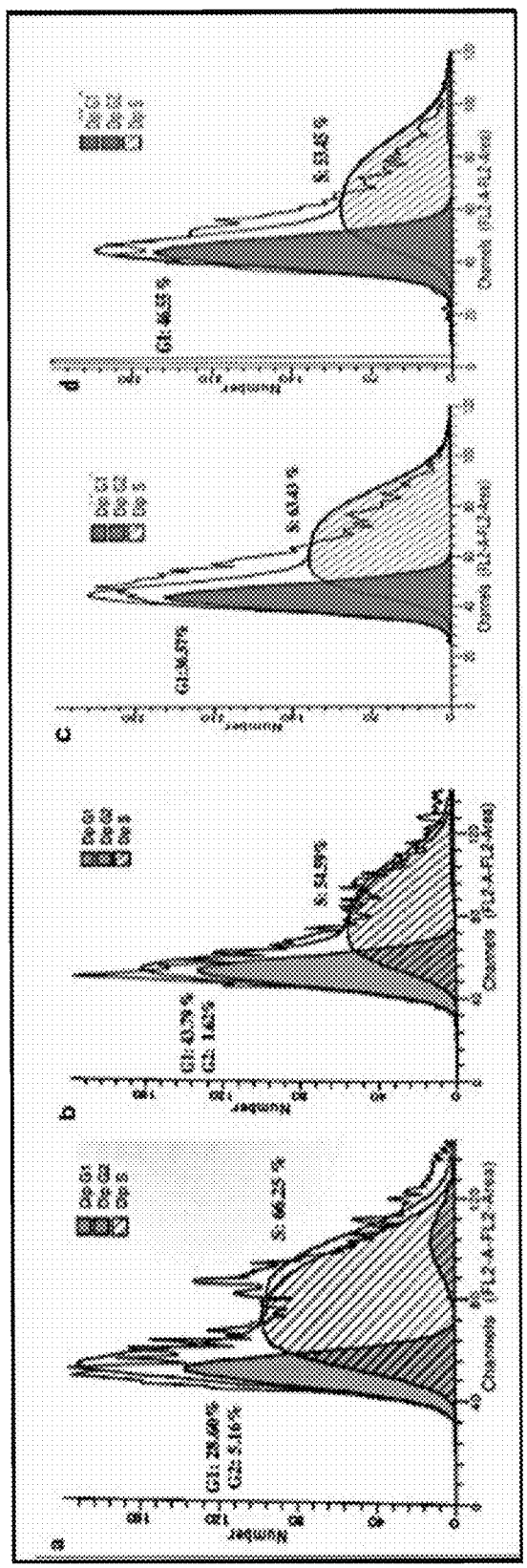
FIG. 50 shows Cell cycle analysis of non-treated MDA-MB-231 cells day 1 a) TCP and b) PCL+HA fibers; day 7 c) TCP and d) PCL+HA random fibers.

On TCP for non-treated cells at day 1, 29% of the cells were in G0/G1 phase, 66% of the cells were in S phase, and 5% of the cells were in G2 phase (FIG. 50.a.). By day 7, 37% of the cells were in G0/G1 phase, 63% of the cells were in S phase and none of the cells cycled to G2 phase (FIG. 50c.). Thus, more than 60% of non-treated MDA-MB-231 cells were in S phase of the cell cycle for the 7-day culture period.

Figure 51:
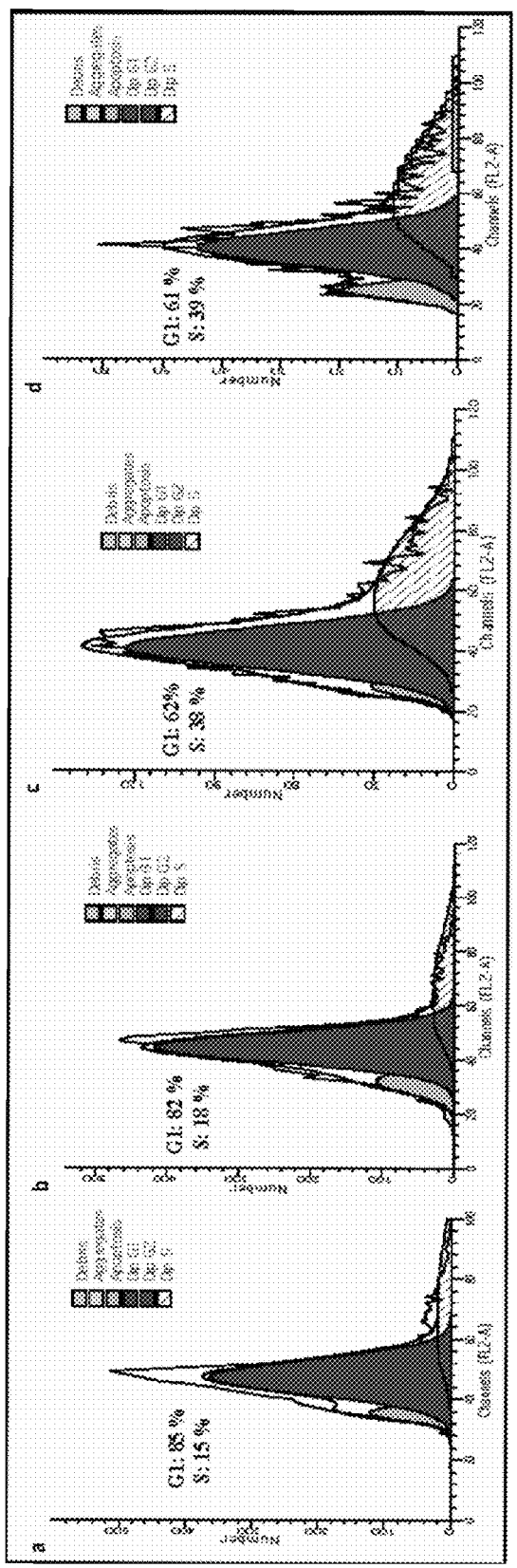
FIG. 51 shows Cell cycle analysis of treated MDA-MB-231 cells day 1 a) TCP and b) PCL+HA fibers; day 7 c) TCP and d) PCL+HA fibers.

Non-treated MDA-MB-231 cells on PCL+HA random scaffolds at day 1, showed that 44% were in G0/G1 phase, while 54.3% of the cells were in S phase, and 1.7% of the cells cycled to G2 phase (FIG. 50b.). By day 7, 46% of the cells were in G0/G1 phase and 54% of the cells transitioned to the S phase while none of the cells cycled to G2 phase (FIG. 50d.). Thus comparing day 1 to day 7, cells were more equally distributed between G0/G1 phase and S phase on PCL+HA scaffolds than on TCP. Treated MDA-MB-231 cells on TCP at day 1, 85% of the cells were in G0/G1 phase, 15% of the cells were in S phase, none of the cells were in G2 phase (FIG. 51a.). By day 7, 62% of the cells were in G0/G1 phase, 38% of the cells were in S phase and none of the cells cycled to G2 phase (FIG. 51c.). Thus, more than 60% of treated MDA-MB-231 cells were G0/G1 phase of the cell cycle for the 7-day culture period. Treated MDA-MB-231 cells on PCL+HA random fibers at day 1, showed that 82% were in G0/G1 phase, while 18% of the cells were in S phase, and none of the cells cycled to G2 phase (FIG. 51.b.). By day 7, 61% of the treated MDA-MB-231 cells were in G0/G1 phase and 39% of the cells transitioned to the S phase while none of the cells cycled to G2 phase (FIG. 51.d.). Thus comparing day 1 to day 7, at day 1, more cells were in the in G0/G1 phase than the S phase. However by day 7, treated MDA-MB-231 cells were cycling on both PCL+HA random fibers and TCP controls.

Cell Migration: Live Cell Microscopy

Figure 52:
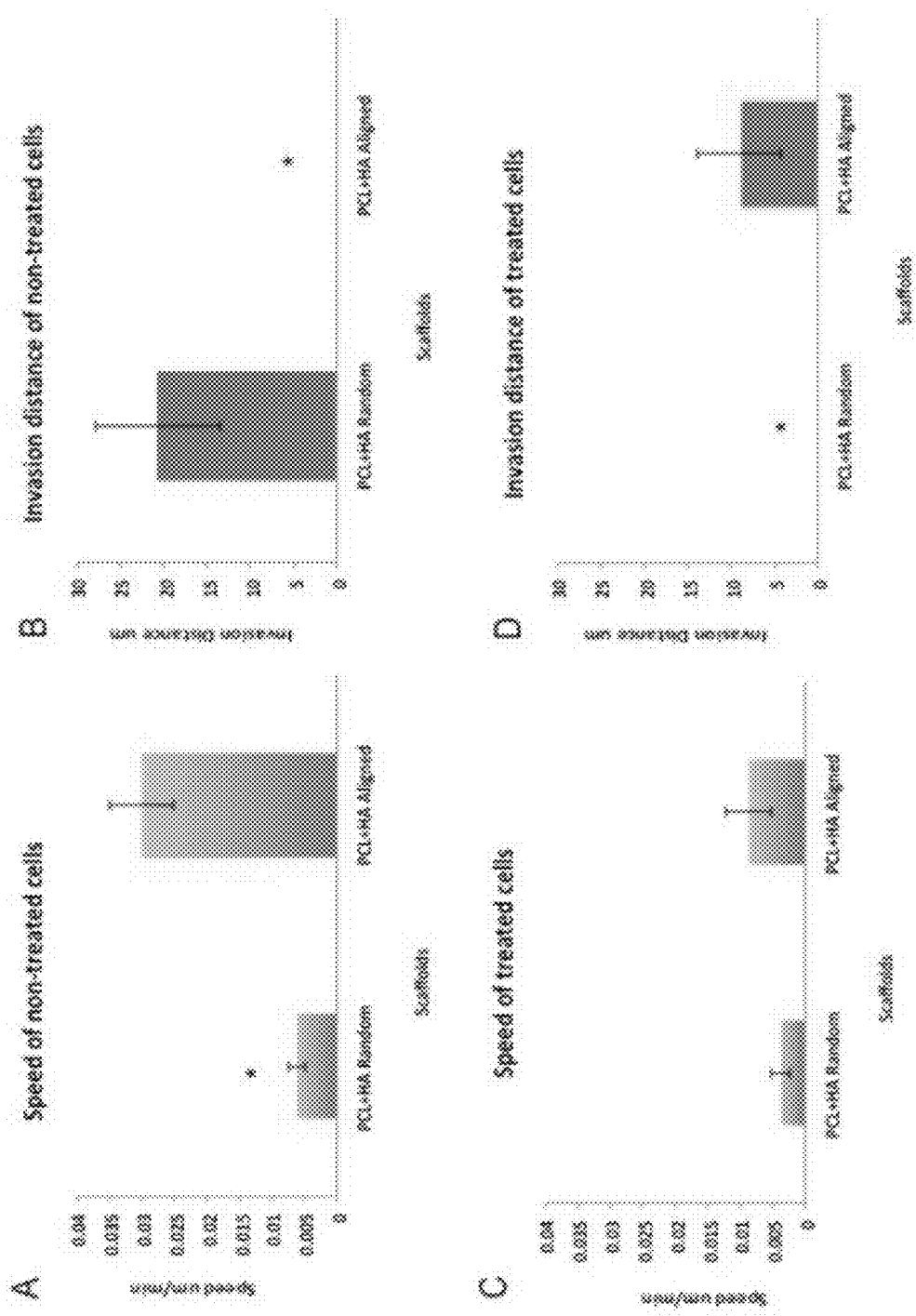
FIG. 52 shows Migration of non-treated and treated MDA-MB-231 on PCL+HA scaffolds. A) Speed of non-treated cells on random and aligned fibers. *p<0.05, significant difference between random and aligned fibers. B) Invasion distance of non-treated on random and aligned fibers. *p<0.05, significant difference between random and aligned fibers. C) Speed of treated cells on random and aligned. D) Invasion distance of treated cells on random and aligned fibers. *p<0.05, significant difference between random and aligned fibers.

For the migration studies only non-treated and treated MDA-MB-231 cells were evaluated on scaffolds after 3 hours of culture. On PCL+HA random fibers, non-treated cells had a mean speed of 0.0061±0.001 μm/min (FIG. 4.15.A) and a mean invasion distance of 20.6±7 μm (FIG. 52.B). On PCL+HA aligned fibers, non-treated cells had a mean speed of 0.03±0.005 μm/min (FIG. 52.C) and a mean invasion distance of 0.001±0.005 μm (FIG. 52.D). Non-treated cells had a significantly higher migration speed on PCL+HA aligned fibers than on PCL+HA random fibers. Non-treated cells had a significantly higher invasion distance on PCL+HA random fibers than on PCL+HA aligned fibers.

Treated cells had a mean speed of 0.004 μm/min (FIG. 52.C) and little to no mean invasion distance (FIG. 52.D) on PCL+HA random fibers. On PCL+HA aligned fibers, treated cells had a mean speed of 0.008 μm/min (FIG. 52.C) and a mean invasion distance of 9.01±4.7 μm (FIG. 52.D). There was significant difference in mean speed and mean invasion distance between treated cells on the different scaffolds. Treated cells on PCL+HA aligned fibers had a significantly higher migration speed than treated cells on random PCL+HA fibers. Similarly, treated cells on PCL+HA aligned had significantly higher invasion distance than on PCL+HA random fibers.

Gene Expression

Figure 53:
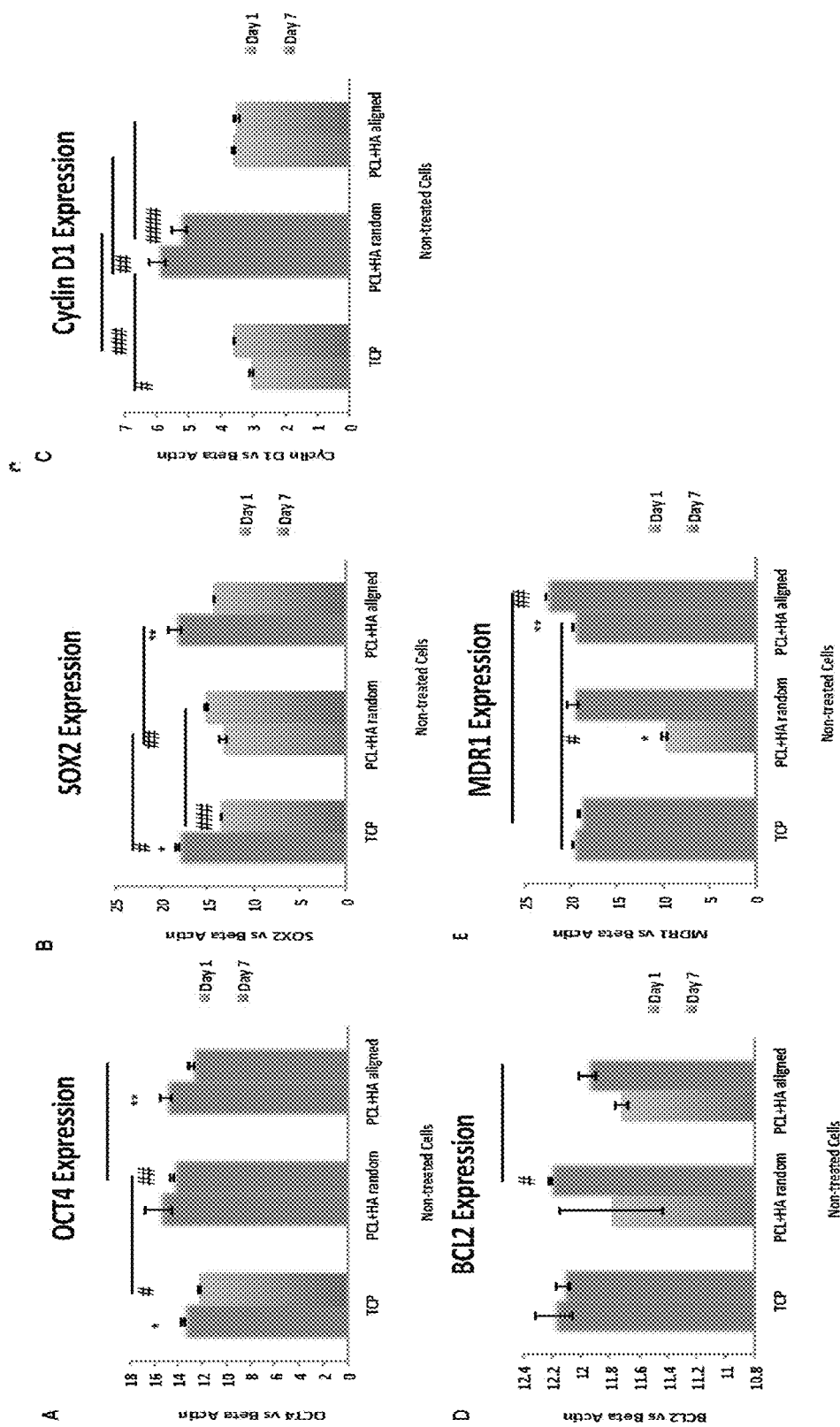
FIG. 53 shows Gene Expression of non-treated MDA-MB-231 cells on PCL+HA random fibers for 7-day culture periods in comparison to TCP. A) OCT4 expression. *p<0.05, significant difference between day 1 and day 7 on TCP. **p<0.05, significant difference between day 1 and day 7 on PCL+HA aligned fibers. # p<0.05, significant difference in expression at day 7 between TCP and PCL+HA random fibers. ## p<0.05, significant difference at day 7 between TCP and PCL+HA random fibers. B) SOX2 expression. *p<0.05, significant difference between day 1 and day 7 on TCP. **p<0.05, significant difference between day 1 and day 7 on PCL+HA aligned fibers. # p<0.05, significant difference in expression at day 1 between TCP and PCL+HA random fibers. ## p<0.05, significant difference in expression at day 1 between PCL+HA random and aligned fibers. ### p<0.05, significant difference at day 1 between TCP and PCL+HA random fibers. C) Cyclin D1 expression. # p<0.05, significant difference in expression at day 1 between TCP and PCL+HA random fibers. ## p<0.05, significant difference in expression at day 1 between PCL+HA random and aligned fibers. ### p<0.05, significant difference at day 1 between TCP and PCL+HA random fibers. #### p<0.05, significant difference at day 7 between PCL+HA random and aligned fibers. D) BCL2 expression. # p<0.05, significant difference in expression at day 7 between PCL+HA random and aligned fibers. E) Multiple Drug Resistant 1 (MDR1) gene expression. *p<0.05, significant difference between day 1 and day 7 on PCL+HA random fibers. **p<0.05, significant difference between day 1 and day 7 on PCL+HA aligned fibers. # p<0.05, significant difference in expression at day 1 between PCL+HA random fibers and remaining surfaces. ## p<0.05, significant difference in expression at day 7 between PCL+HA aligned scaffolds and remaining surfaces.

Gene expression results for BCCs cultured on PCL+HA random fibers after 1 day and 7 days in culture are shown in FIG. 53. The genes of interest were OCT4 (stem cell), Sox2 (stem cell), Cyclin D1 (cell cycle), BCL2 (anti-apoptosis), MDR1 (drug resistance). The results were normalized to the housekeeping gene GAPDH.

Non-Treated MDA-MB-231 Cells

On TCP, non-treated MDA-MB-231 cells had a significantly higher expression of the OCT4 gene at day 1 than at day 7 (*$p<0.05$) (FIG. 53 A); a significantly higher expression of the SOX2 gene at day 1 than at day 7 (*$p<0.05$) (FIG. 53 B); and no significant difference in Cyclin D1 and BCL2 and MDR1 genes expression during the 7 days culture period (FIGS. 53 C, D, and E respectively).

On PCL+HA random fibers, non-treated MDA-MB-231 cells had no significant difference in expression of the OCT4, SOX 2, Cyclin D1 and BCL2 genes between day 1 and 7 (FIGS. 53 A, B, C and D respectively). Non-treated MDA-MB-231 cells had significantly lower MDR1 gene expression at day 1 as compared to day 7 (*$p<0.05$) (FIG. 53 E).

On PCL+HA aligned fibers, non-treated MDA-MB-231 cells had a significantly higher expression of the OCT4, and SOX2 genes at day 1 than at day 7 (p<0.05) (FIGS. 53 A and B respectively). Non-treated MDA-MB-231 cells did not have significant difference in Cyclin D1 and BCL2 genes between day 1 and day 7 (FIGS. 53 C and D respectively). MDR1 expression was significantly lower at day 1 than at day 7 for non-treated cells (p<0.05) (FIG. 53 E).

When comparisons between TCP and the different bone-like scaffolds were made, there was no significant difference in expression of the OCT4 gene at day 1 between different surfaces. At day 7, non-treated cells expressed OCT4 gene significantly higher on PCL+HA random fibers as compared to TCP and PCL+HA aligned fibers (#p<0.05 and ##p<0.05) (FIG. 53 A). Non-treated cells expressed SOX2 gene significantly lower on PCL+HA random fibers as compared to TCP at day 1 (#p<0.05). Non-treated cells had significantly lower SOX2 gene expression on PCL+HA random fibers as compared to PCL+HA aligned fibers at day 1 (##p<0.05) (FIG. 53 B). At day 7, non-treated cells expressed higher levels of SOX2 on PCL+HA random fibers as compared to TCP (###p<0.05) (FIG. 53 B). Non-treated MDA-MB-231 cells had significantly higher expression of Cyclin D1 gene at day 1 on PCL+HA random fibers than on both TCP (#p<0.05) and PCL+HA aligned (##p<0.05). Moreover, at day 7, non-treated cells had significantly higher expression of Cyclin D1 gene on PCL+HA random than on both TCP (###p<0.05) and PCL+HA aligned at day 7 (####p<0.05) (FIG. 53 C). There was no significant difference in BCL2 gene expression between different surfaces at day 1. At day 7, BCL2 was expressed significantly higher on PCL+HA random fibers as compared to PCL+HA aligned (#p<0.05) (FIG. 53 D). MDR1 expression was significantly lower at day 1 on PCL+HA random as compared to both TCP and PCL+HA aligned fibers (#p<0.05). MDR1 was expressed significantly higher at day 7 on PCL+HA aligned as compared to both TCP and PCL+HA random fibers (FIG. 53 E).
Treated MDA-MB-231 Cells On TCP, treated MDA-MB-231 cells had a significantly higher expression of the OCT4 gene at day 1 than at day 7 (*p<0.05) (FIG. 54A); a significantly higher expression of the SOX2 gene at day 1 as compared to day 7 (*p<0.05) (FIG. 54 B); no significant difference in expression of the Cyclin D1 and BCL2 genes between day 1 and day 7 (FIGS. 54 C and D respectively); a significantly lower MDR1 gene expression at day 1 as compared to day 7 (*p<0.05) (FIG. 54 E).

Figure 54:
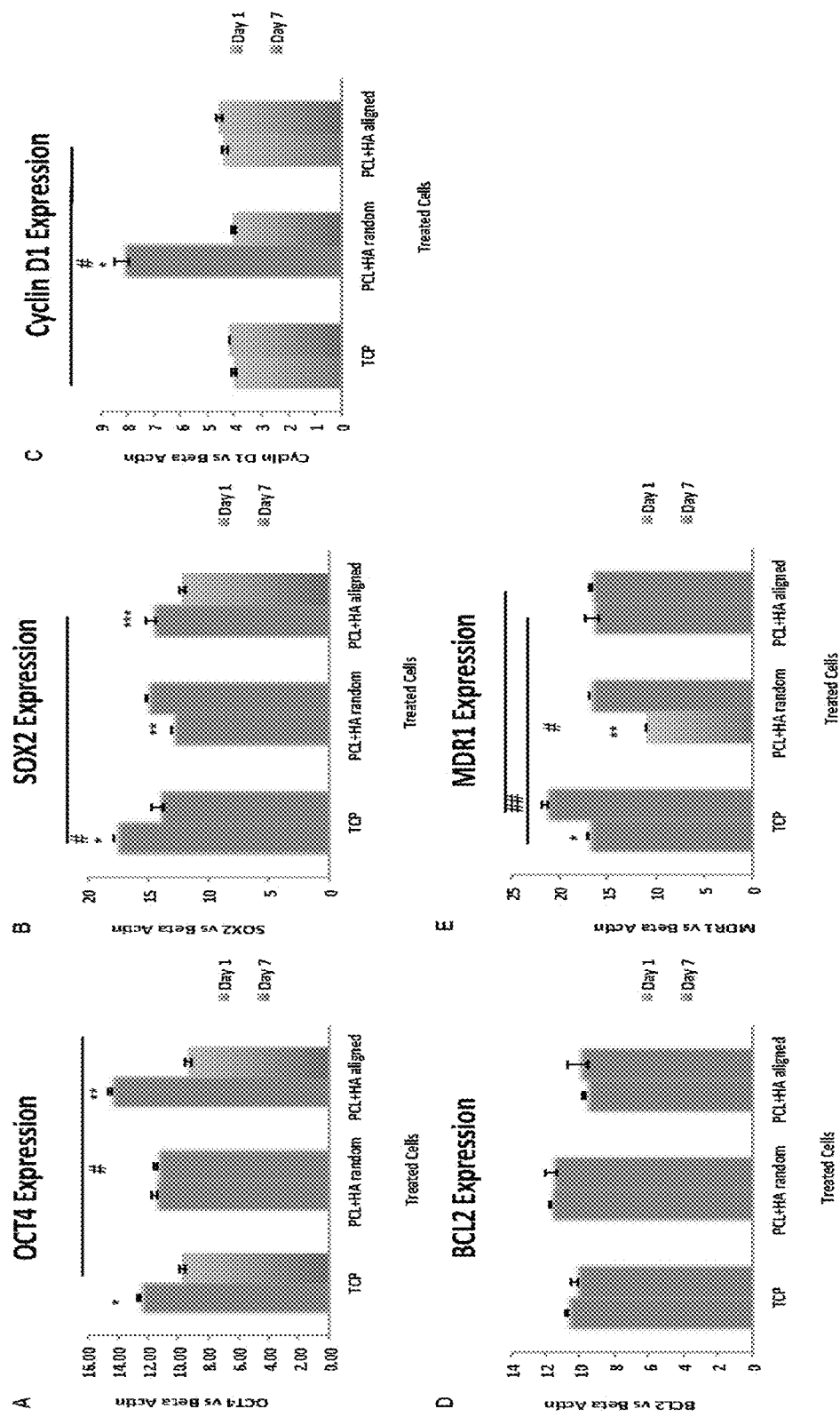
FIG. 54 shows Gene Expression of treated MDA-MB-231 cells on PCL+HA random fibers for 7-day culture periods in comparison to TCP. A) OCT4 expression. *p<0.05, significant difference between day 1 and day 7 on TCP. **p<0.05, significant difference between day 1 and day 7 on PCL+HA aligned fibers. # p<0.05, significant difference in expression at day 7 between PCL+HA random fibers and remaining surfaces. B) SOX2 expression. *p<0.05, significant difference between day 1 and day 7 on TCP. p<0.05 and *p<0.05, significant difference between day 1 and day 7 on PCL+HA random and aligned fibers respectively. # p<0.05, significant difference in expression at day 1 between TCP and remaining scaffold fibers. C) Cyclin D1 expression. *p<0.05, significant difference between day 1 and day 7 on PCL+HA random fibers. # p<0.05, significant difference in expression at day 1 between PCL+HA random fibers and remaining surfaces. D) BCL2 expression. E) Multiple Drug Resistant 1 (MDR1) gene expression. *p<0.05, significant difference between day 1 and day 7 on TCP. **p<0.05, significant difference between day 1 and day 7 on PCL+HA random fibers. # p<0.05, significant difference in expression at day 1 between PCL+HA random fibers and remaining surfaces. ## p<0.05, significant difference in expression at day 7 between TCP and remaining surfaces.

On PCL+HA random fibers, treated MDA-MB-231 cells had no significant difference in expression of the OCT4 gene between day 1 and day 7 (FIG. 54A); a significantly lower SOX2 gene expression at day 1 than at day 7 (**p<0.05) (FIG. 54 B); a significantly higher expression of Cyclin D1 at day 1 than at day 7 (*p<0.05) (FIG. 54 C); no significant difference in BCL2 gene expression between day 1 and day 7 (FIG. 54 D); a significantly lower expression of MDR1 gene at day 1 as compared to day 7 (**p<0.05) (FIG. 54 E).

On PCL+HA aligned fibers, treated MDA-MB-231 cells had a significantly higher expression of the OCT4, and SOX2 genes at day 1 than at day 7 (**p<0.05) (FIGS. 54 A and B respectively); no significant difference in expression of the Cyclin D1, BCL2 and MDR1 genes between day 1 and day 7 (FIGS. 54 C, D and E respectively).

Figure 55:
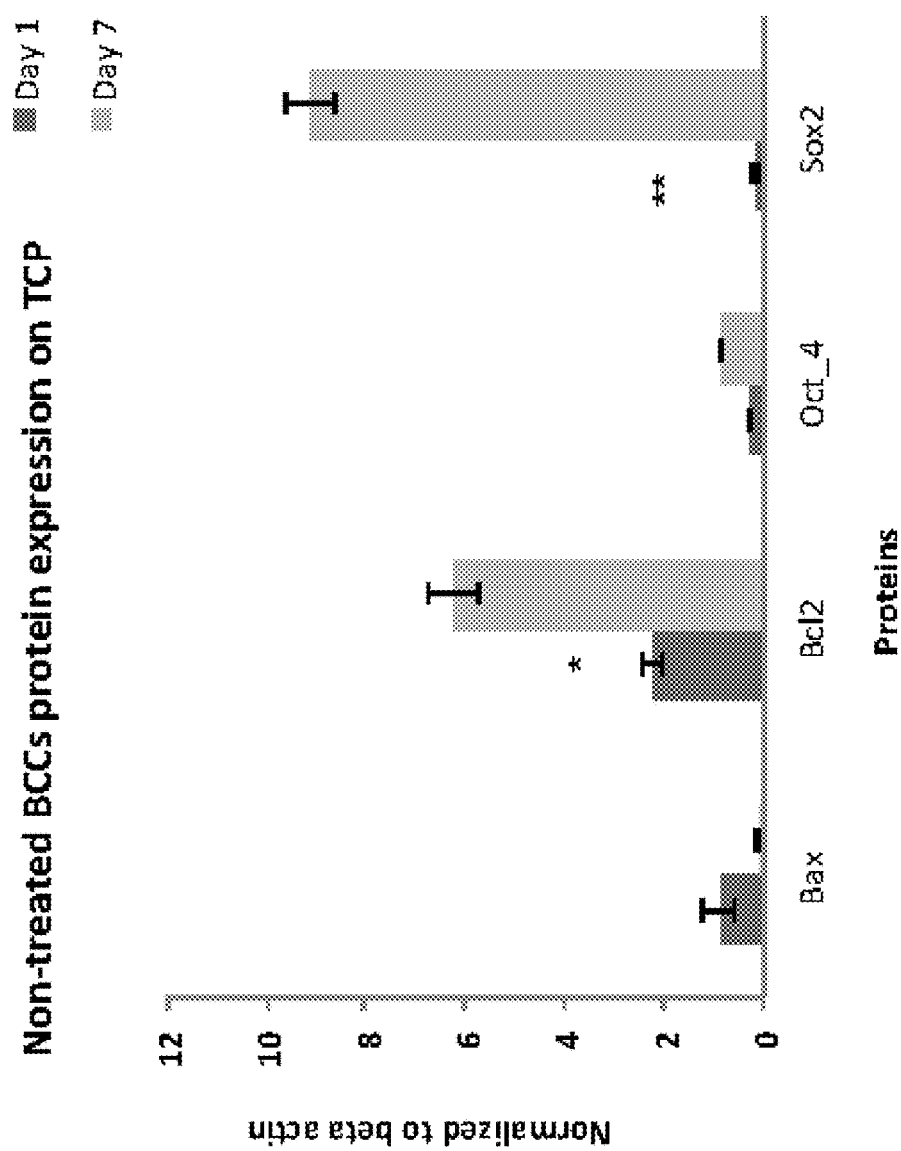
FIG. 55 shows Densitometric analysis of western blot band analysis for Bax, Bcl2, Oct-4 and Sox2 protein expressions normalized to beta actin protein for non-treated MDA-MB-231 cells on TCP after 7 days of culture. *p<0.05, significant difference in Bcl2 protein expression between day 1 and day 7 fibers. **p<0.05, significant difference in Sox2 protein expression between day 1 and day 7.
Figure 56:
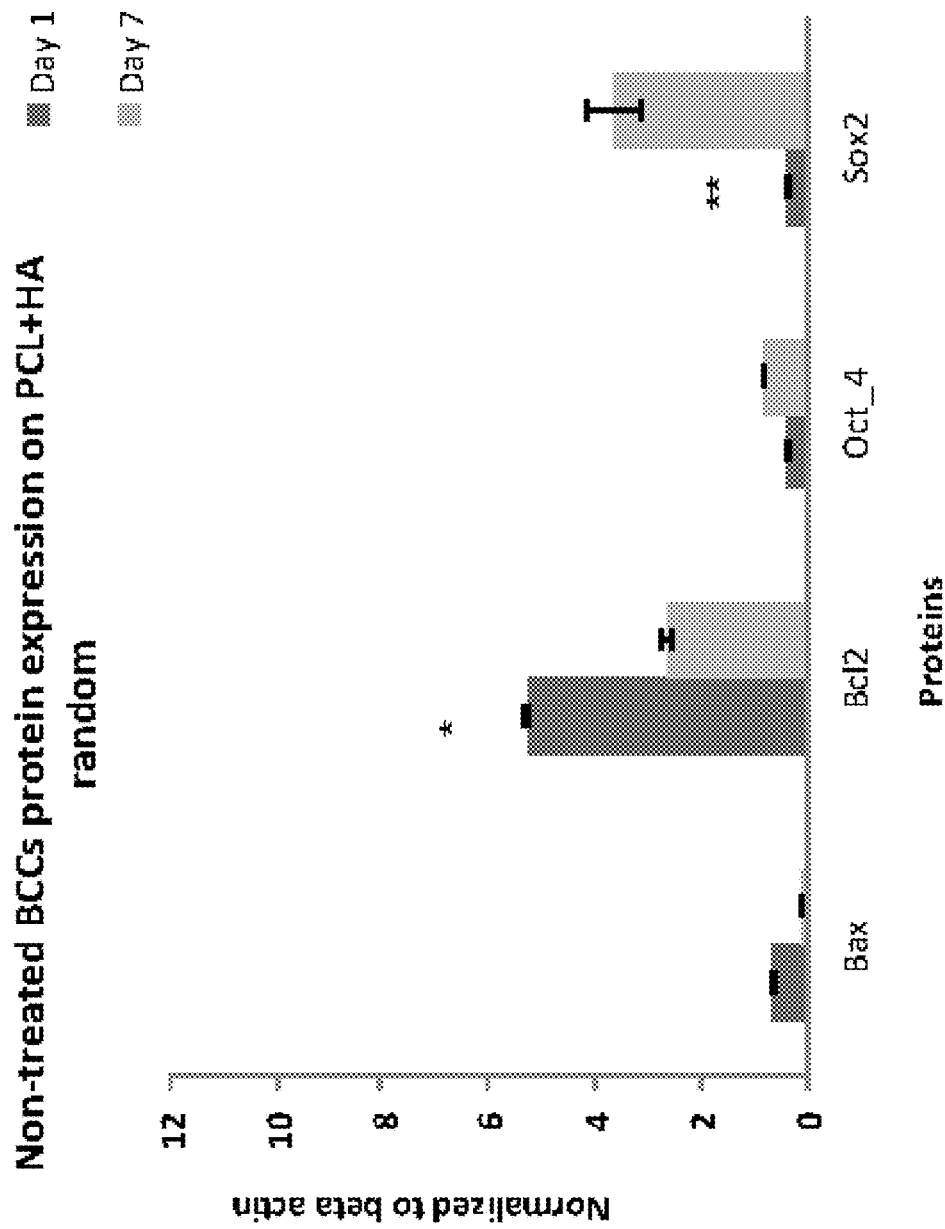
FIG. 56 shows Densitometric analysis of western blot band analysis for Bax, Bcl2, Oct-4 and Sox2 protein expressions normalized to beta actin protein for non-treated MDA-MB-231 on PCL+HA random fibrous scaffolds after 7 days of culture. *p<0.05, significant difference in Bcl2 protein expression between day 1 and day 7. **p<0.05, significant difference in Sox2 protein expression between day 1 and day 7.
Figure 57:
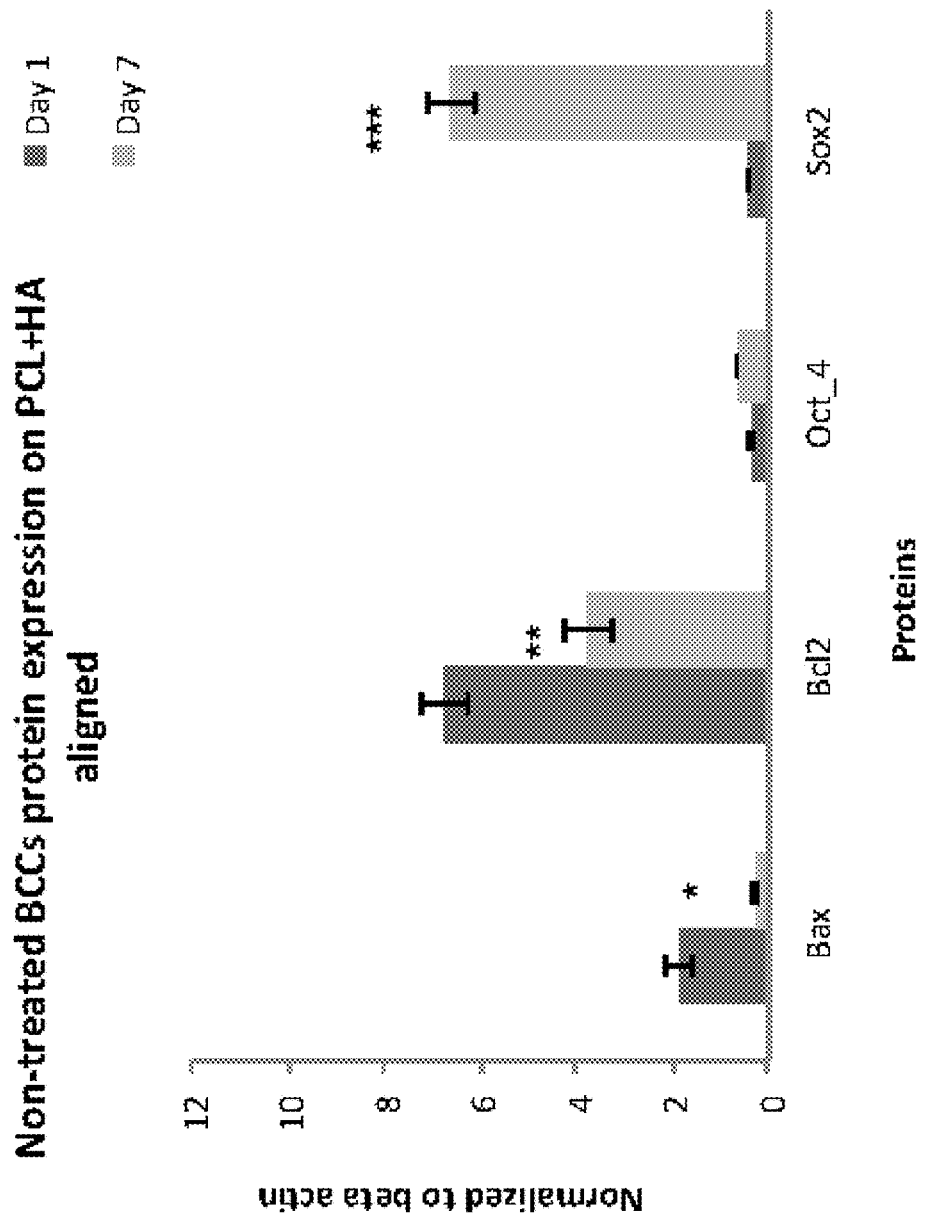
FIG. 57 shows Densitometric analysis of western blot band analysis for Bax, Bcl2, Oct-4 and Sox2 protein expressions normalized to beta actin protein for non-treated MDA-MB-231 on PCL+HA aligned fibrous scaffolds after 7 days of culture. *p<0.05, significant difference in Bcl2 protein expression between day 1 and day 7. **p<0.05, significant difference in Sox2 protein expression between day 1 and day 7.

When comparisons between TCP and the different scaffolds were made, treated cells had no significant difference in expression of the OCT4 gene at day 1. At day 7 treated cells had a significantly higher OCT4 gene expression on PCL+HA random fibers as compared to TCP and PCL+HA aligned fibers (#p<0.05) (FIG. 54 A). Treated cells expressed SOX2 gene significantly lower on both PCL+HA random and aligned fibers than on TCP at day 1 (#p<0.05) (FIG. 54 B). At day 7, there was no significant difference in SOX2 gene expression between different groups. For cyclin D1 gene expression, treated MDA-MB-231 cells had significantly higher expression on PCL+HA random fibers (#p<0.05) than on TCP and PCL+HA aligned fibers (FIG. 54 C) at day 1. At day 7, there was no significant difference in Cyclin D1 expression between groups. There was no significant difference in BCL2 gene expression between the TCP, random and aligned PCL+HA fibers on both day 1 and day 7 (FIG. 54 D). MDR1 expression was significantly lower at day 1 on PCL+HA random as compared to both TCP and PCL+HA aligned fibers (#p<0.05). At day 7, MDR1 gene was expressed significantly lower on both PCL+HA random and aligned fibers as compared to TCP (##p<0.05) (FIG. 54 E).
Protein Expression Western blot analysis showed the proteins Oct-4, Sox2, Bax and Bcl2 expression in both TCP and PCL+HA fibrous scaffolds as illustrated in FIGS. 55-57. Protein content was quantified by normalizing to the housekeeping protein Beta-actin.
Non-Treated MDA-MB-231 Cells On TCP, non-treated MDA-MB-231 cells had little no expression of Oct-4 protein at days 1 and 7 in culture. On TCP, non-treated MDA-MB-231 cells had Sox2 expression at day 1, which significantly increased by day 7 (~9-fold increase). On TCP, non-treated MDA-MB-231 cells expressed Bax protein at both days 1 and day 7 in culture. On TCP, non-treated MDA-MB-231 cells had a 2-fold expression of Bcl2 at day 1 which increased to 6 folds at day 7 (FIG. 55).

On PCL+HA random fibers, non-treated MDA-MB-231 cells had little to no Oct-4 protein expression at day 1 and an increase in expression at day 7 in culture. On PCL+HA random fibers, non-treated MDA-MB-231 cells expressed Sox 2 at day 1, which increased significantly by day 7 (~4-fold). On PCL+HA random fibers, non-treated MDA-MB-231 cells expressed low levels of Bax protein at day 1 and little to none by day 7. On PCL+HA random fibers, non-treated MDA-MB-231 cells expressed high levels of Bcl2 protein (5-fold expression) at day 1 which reduced by day 7 (2-fold expression) (FIG. 56).

Figure 58:
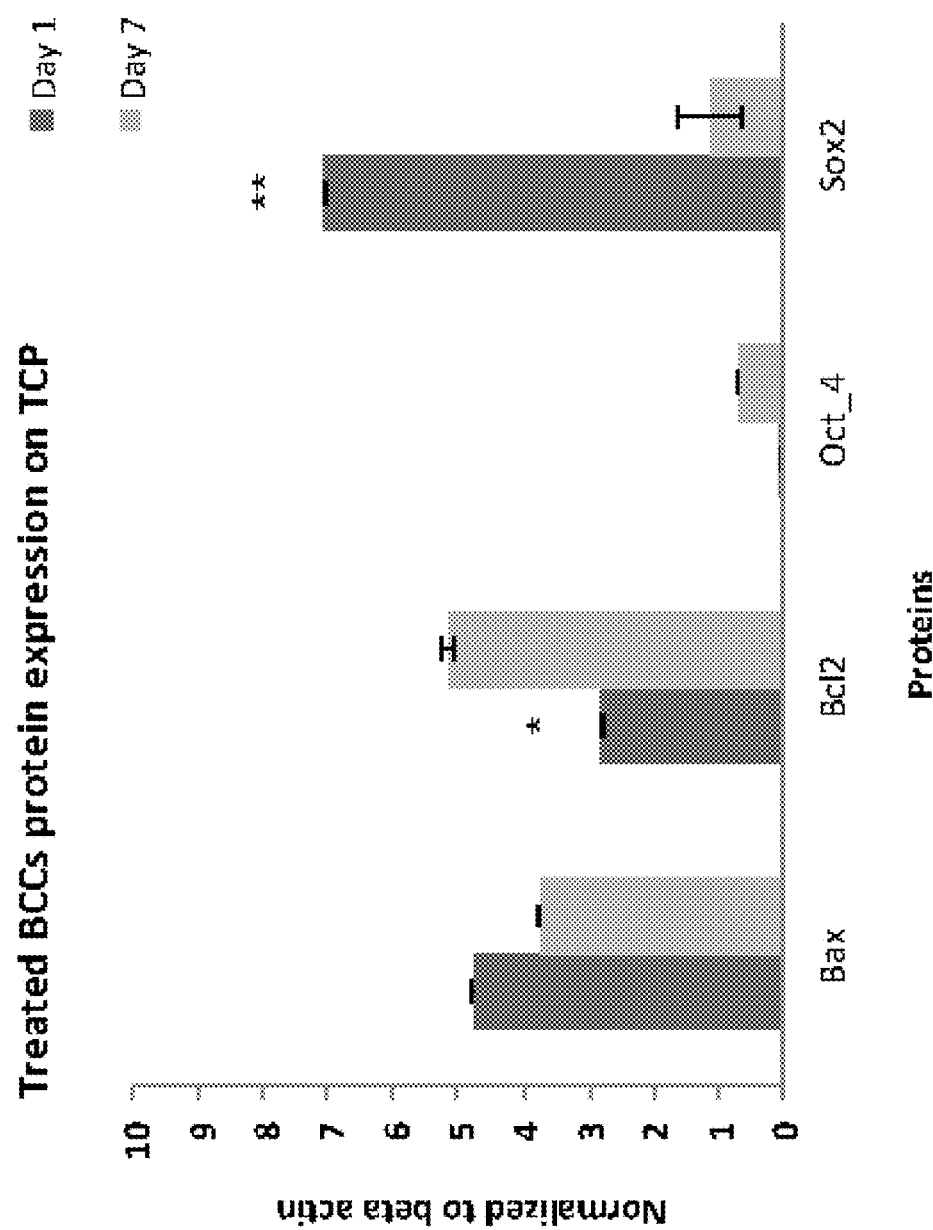
FIG. 58 shows Densitometric analysis of western blot band analysis for Bax, Bcl2, Oct-4 and Sox2 protein expressions normalized to beta actin protein for treated MDA-MB-231 cell on TCP after 7 days of culture. *p<0.05, significant difference in Bcl2 protein expression between day 1 and day 7. **p<0.05, significant difference in Sox2 protein expression between day 1 and day 7.

On PCL+HA aligned fibers, non-treated MDA-MB-231 cells had little to no Oct-4 protein expression at day 1 and an increase in expression at day 7 in culture. This was not significantly different from TCP. On PCL+HA aligned fibers, non-treated MDA-MB-231 cells expressed Sox2 at day 1, which increased significantly by day 7 (~4-fold). This was similar to TCP except at day 7 TCP had a ~8 fold increase in expression. On PCL+HA aligned fibers, non-treated MDA-MB-231 cells expressed high levels of Bax protein at day 1 and little to none by day 7. This expression was similar to TCP. On PCL+HA aligned fibers, non-treated MDA-MB-231 cells expressed high levels of Bcl2 protein (6.5-foldS) at day 1 which reduced by day 7 (4 folds) (FIG. 56). This trend was different for TCP.
Treated MDA-MB-231 Cells On TCP, treated MDA-MB-231 cells had little to no Oct-4 expression at day 1 and an increased expression by day 7; and a significant increased (~7-fold) Sox2 expression at day 1 which decreased by day 7. Moreover, treated MDA-MB-231 cells highly expressed Bax both at days 1 (~5-fold) and 7 (~3-fold). Similarly, treated MDA-MB-231 cells had an increased Bcl2 protein expression at day 1 (~3-fold) and at day 7 (~4.5 fold change) (FIG. 58).

Figure 59:
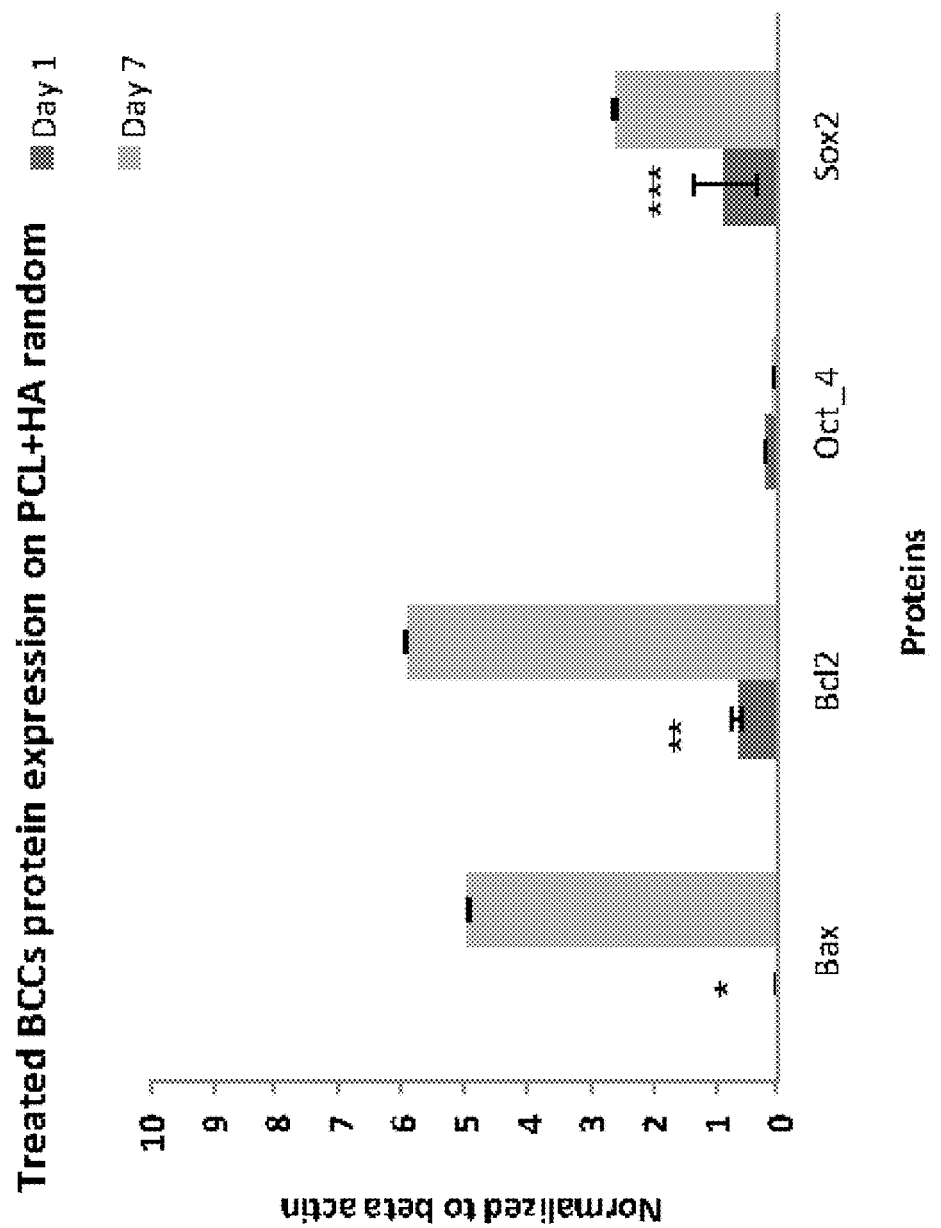
FIG. 59 shows Densitometric analysis of western blot band analysis for Bax, Bcl2, Oct-4 and Sox2 protein expressions normalized to beta actin protein for non-treated MDA-MB-231 on PCL+HA random fibrous scaffolds after 7 days of culture. *p<0.05, significant difference in Bax protein expression between day 1 and day 7. p<0.05, significant difference in Bcl2 protein expression between day 1 and day 7. *p<0.05, significant difference in Sox2 protein expression between day 1 and day 7.
Figure 60:
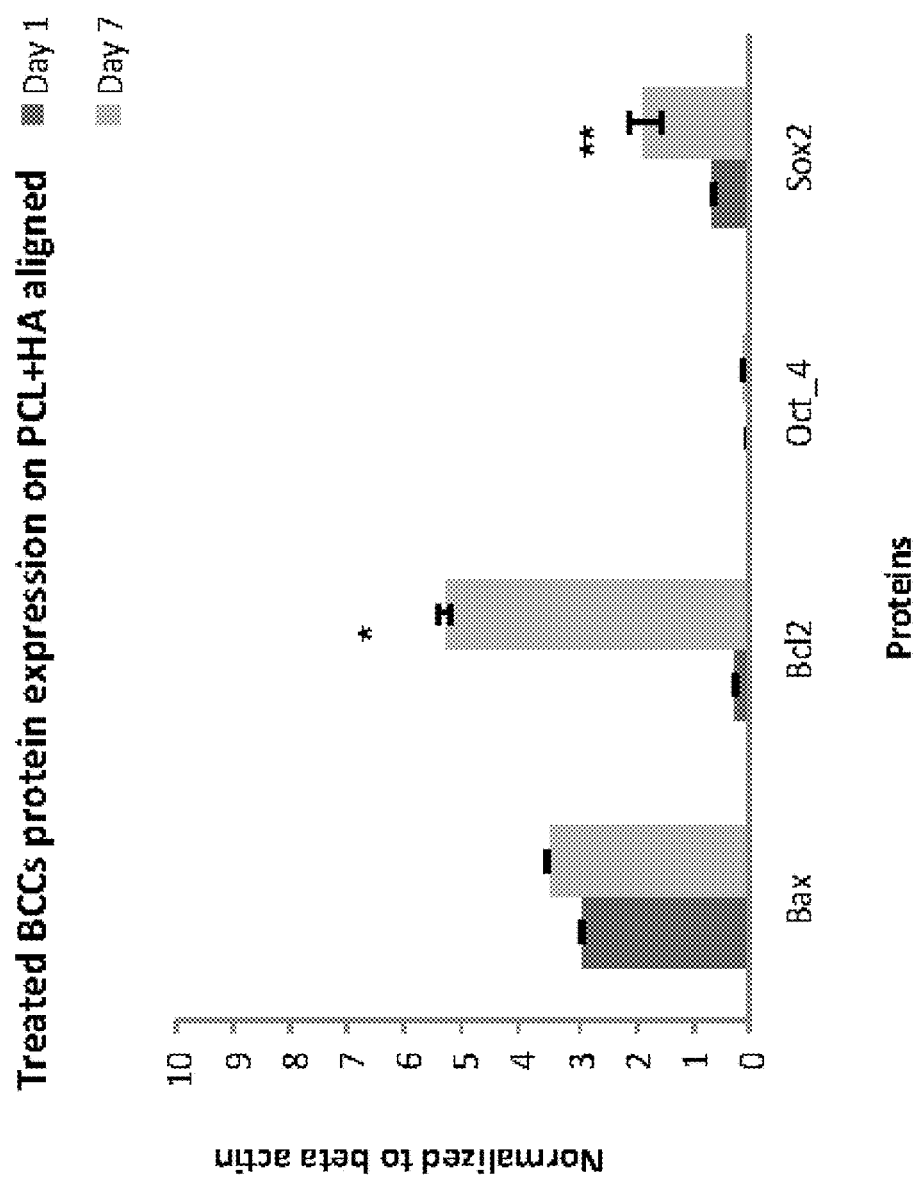
FIG. 60 shows Densitometric analysis of western blot band analysis for Bax, Bcl2, Oct-4 and Sox2 protein expressions normalized to beta actin protein for non-treated MDA-MB-231 on PCL+HA aligned fibrous scaffolds after 7 days of culture. *p<0.05, significant difference in Bax protein expression between day 1 and day 7. p<0.05, significant difference in Bcl2 protein expression between day 1 and day 7. *p<0.05, significant difference in Sox2 protein expression between day 1 and day 7.

On PCL+HA random fibers, treated MDA-MB-231 cells had little to no Oct-4 protein expression at both days 1 and 7 in culture. Sox2 expression was also low at day 1 then significantly increased by day 7. Similarly, there was little to n expression of Bax proteins at day 1 and a significant increase in expression at day 7 (~5-fold). Following the same trend, Bcl2 expression was low at day 1 and significantly high by day 7 (~6-fold) (FIG. 59). On PCL+HA aligned fibers, treated MDA-MB-231 cells had little to no Oct-4 protein expression at both days 1 and 7 in culture. Treated cells expressed Sox2 and this significantly increased by day 7. This expression profile was different on TCP. Treated cells had a significantly high expression in Bax proteins at days 1 and 7 (~3 folds), which was lower than TCP (~4 folds). Bcl2 expression was significantly low at day 1 and significantly high by day 7 (~5-fold) (FIG. 60). This trend was similar to TCP.

miRNA Expression

So far it has been observed that both PCL and PCL+HA 3-D fibrous scaffolds models have been able to differently modulate the morphology, proliferation, metabolic activity, migration and cell cycle behavior of BCCs in vitro. Key microRNAs involved in BCCs quiescence and BC dormancy have been identified. Therefore, the effect of the fibrous scaffolds on the relative expression levels of miRNA-222 (miR-222) of both non-treated and treated MDA-MB-231 cells was investigated.

Figure 61:
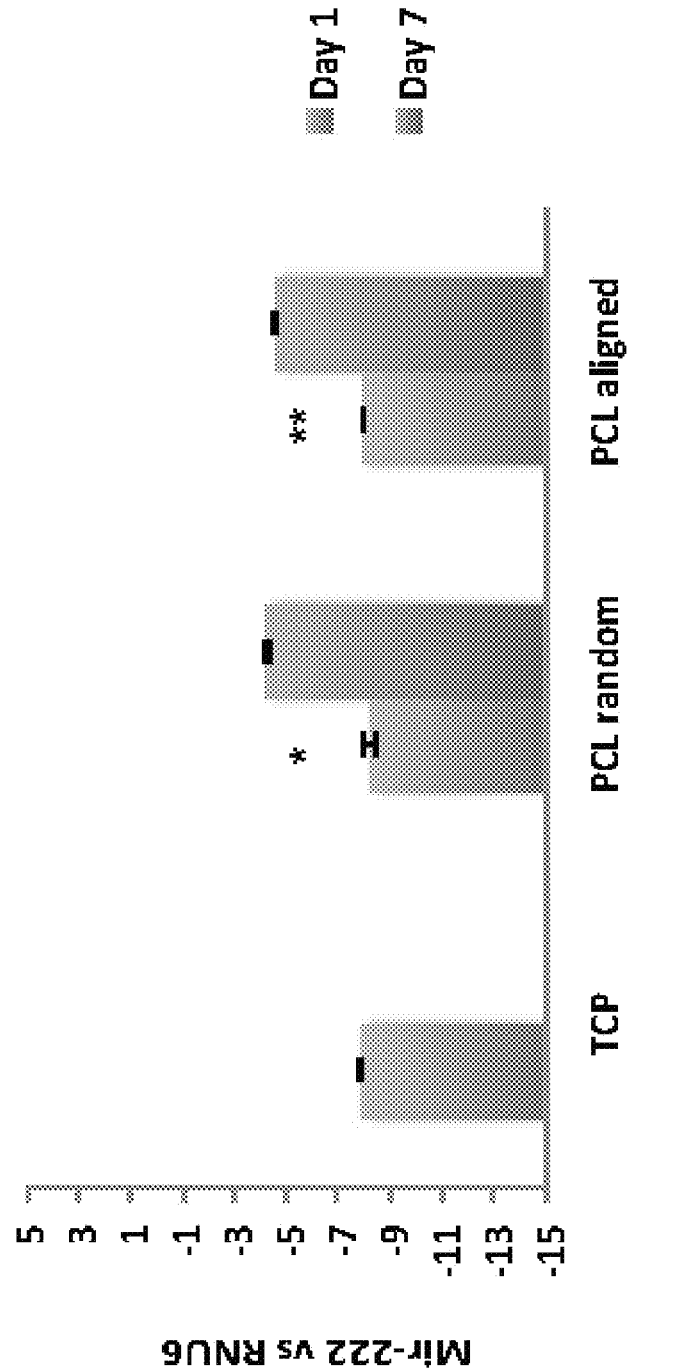
FIG. 61 shows Mir-222 Expression of non-treated MDA-MB-231 cells on TCP, PCL random and aligned scaffolds. *p<0.05, significant difference in expression of miR-222 between day 1 and day 7 on PCL random fibers. **p<0.05, significant difference in expression of miR-222 between day 1 and day 7 on PCL aligned fibers.

On TCP, non-treated cells had low expression of miR-222 at day 1; expression at day 7 on TCP was not determined. On both PCL random and aligned fibers, non-treated cells had a significantly lower expression of miR-222 gene at day 1 than at day 7 (*$p<0.05$ and $p<0.05$ respectively) (FIG. 61**).

Figure 62:
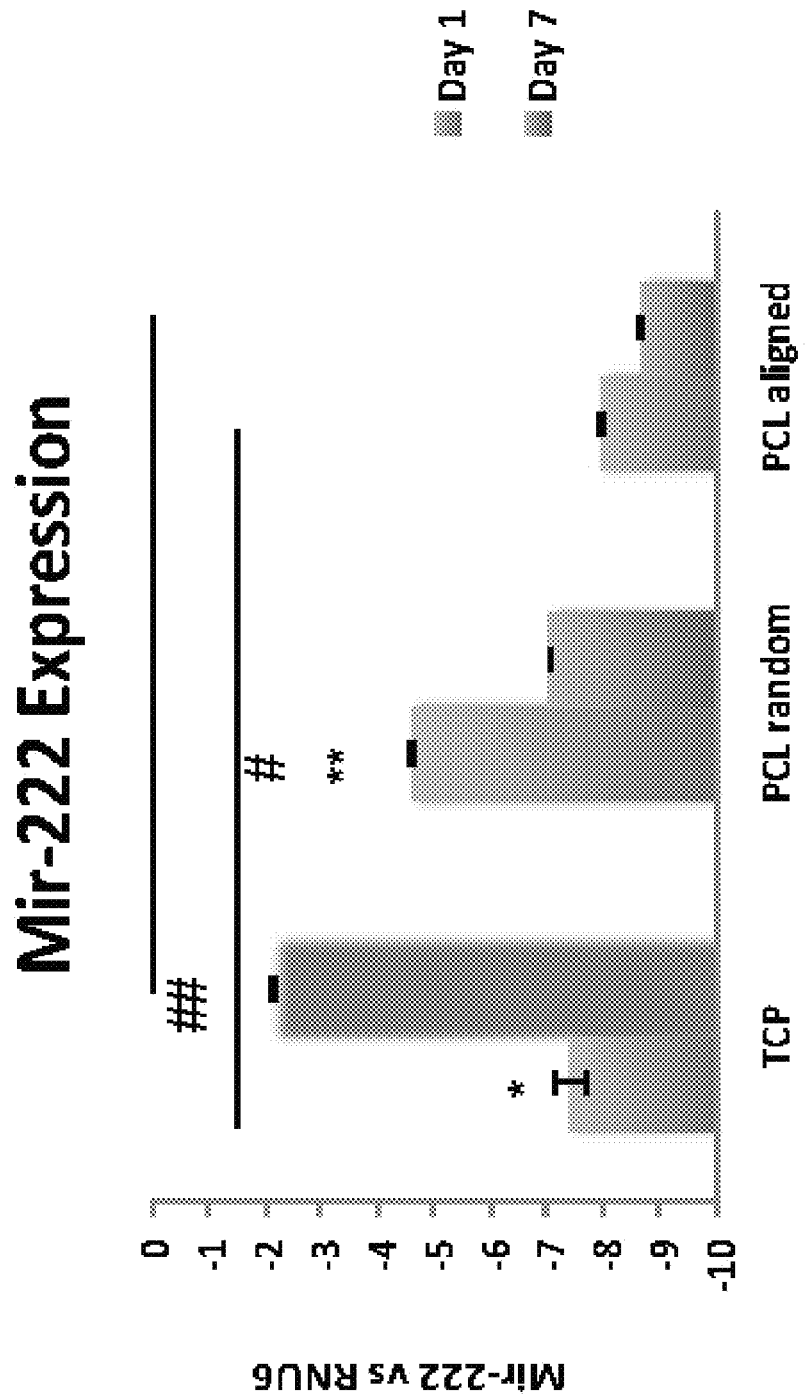
FIG. 62 shows Mir-222 Expression of treated MDA-MB-231 cells on TCP, PCL random and aligned scaffolds. *p<0.05, significant difference in expression of miR-222 between day 1 and day 7 on TCP. **p<0.05, significant difference in expression of miR-222 between day 1 and day 7 on PCL random fibers. #p<0.05, significant difference in expression of miR-222 between at day 1 between PCL random fibers and the remaining surfaces. ## p<0.05, significant difference in expression of miR-222 at day 7 between TCP and the remaining surfaces.

On TCP, treated cells had a significantly lower expression of miR-222 gene at day 1 than at day 7 (*$p<0.05$) (FIG. 62). On PCL random fibers, treated cells had a significantly higher expression of miR-222 gene at day 1 than at day 7 (FIG. 62) ($p<0.05$). On PCL aligned, treated cells did not have significant difference in expression of miR-222 expression between day 1 and day (FIG. 62**).

When comparisons between scaffolds and TCP were made, non-treated cells did not have significant difference in expression of miR-222 gene between the different groups at day 1 and day 7. Treated cells showed significantly higher expression of miR-222 gene at day 1 on PCL random than treated cells on TCP and PCL aligned (#$p<0.05$). At day 7, treated cells showed significantly lower expression of miR-222 on PCL random and aligned fibers than on TCP (##$p<0.05$) (FIG. 62).

On PCL+HA random fibers, non-treated cells did not show significant difference in expression of the miR-222 gene at day 1 and day 7. On PCL+HA aligned fibers, non-treated cells had a significantly lower expression of miR-222 at day 1 than at day 7 (*$p<0.05$) (FIG. 63).

Figure 64:
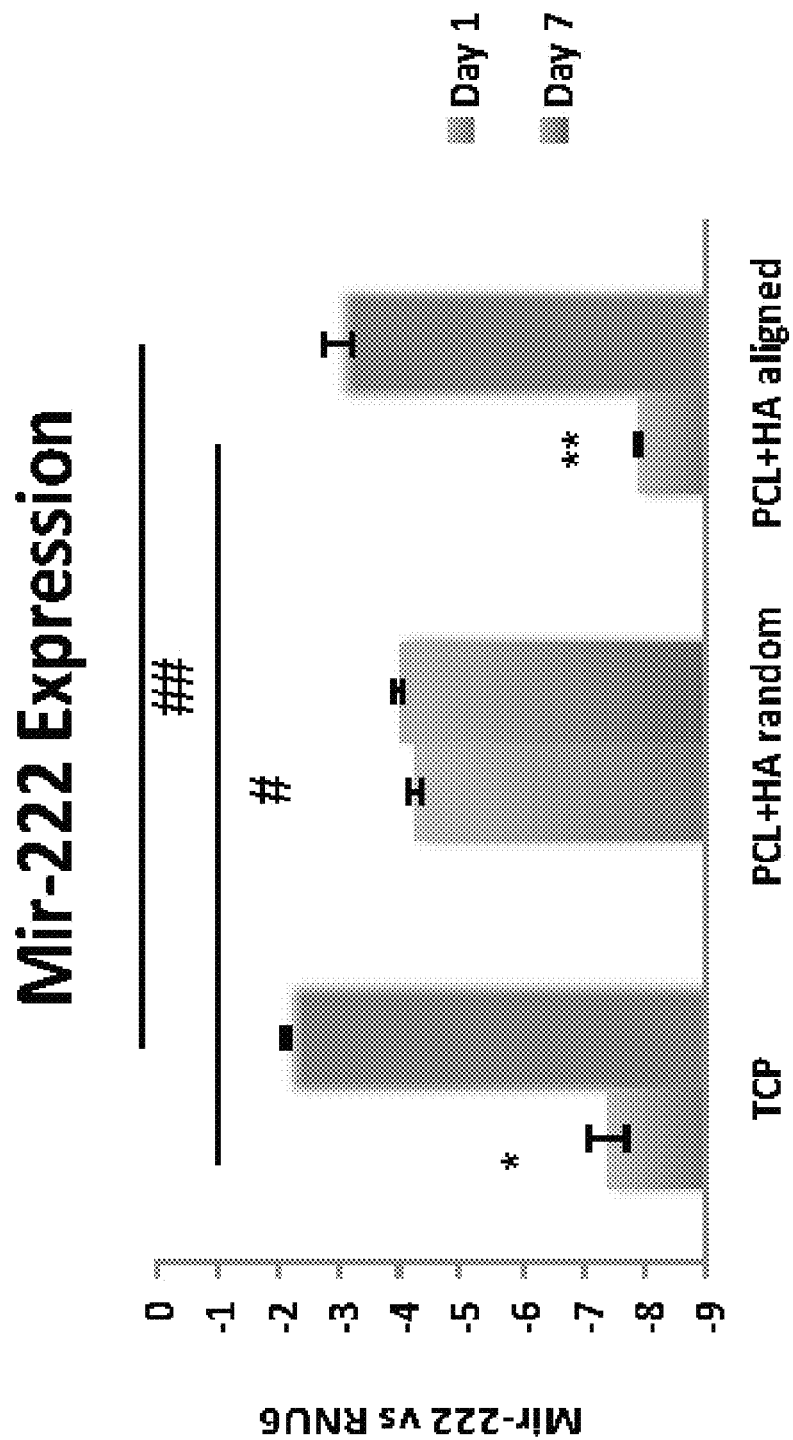
FIG. 64 shows Mir-222 Expression of treated MDA-MB-231 cells on, TCP, PCL+HA random and aligned scaffolds. *p<0.05, significant difference in expression of miR-222 between day 1 and day 7 on TCP. **p<0.05, significant difference in expression of miR-222 between day 1 and day 7 on PCL+HA aligned scaffolds. #p<0.05, significant difference in expression of miR-222 at day 1 between PCL+HA random scaffolds and remaining surfaces. ##p<0.05, significant difference in expression of miR-222 at day 7 between PCL+HA random fibers and remaining surfaces.

Treated cells on PCL+HA random fibers, did not have significant difference in expression of the miR-222 gene between day 1 and day 7. On PCL+HA aligned fibers, treated cells had significantly lower expression of miR-222 gene at day 1 than at day 7 ($p<0.05$) (FIG. 64**).

Figure 63:
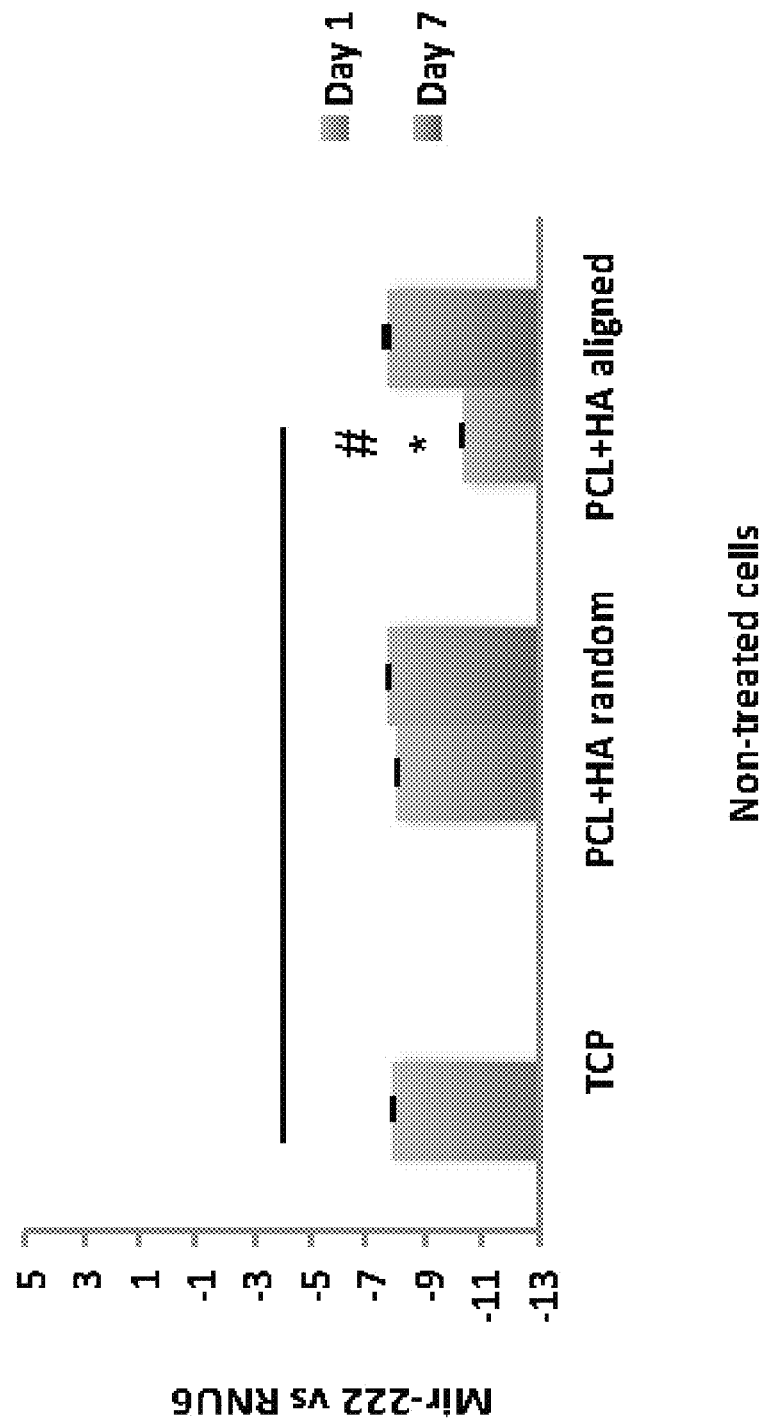
FIG. 63 shows Mir-222 Expression of non-treated MDA-MB-231 cells on TCP, PCL+HA random and aligned scaffolds. *p<0.05, significant difference in expression of miR-222 between day 1 and day 7 on PCL+HA aligned fibers. #p<0.05, significant difference in expression of miR-222 at day 1 between PCL+HA aligned scaffolds and remaining surfaces.

When comparison was made between TCP and the remaining bone-like scaffolds, miR-222 expression of non-treated cells was significantly lower on PCL+HA aligned fibers at day 1 when compared to PCL+HA random and TCP (#$p<0.05$) (FIG. 63). There was no significant difference in expression between groups at day 7. Moreover, treated cells had significantly higher levels of expression of miR-222 gene on PCL+HA random fibers at day 1 as compared to TCP and PCL+HA aligned fibers at both days 1 and 7 (#$p<0.05$) (FIG. 64). At day 7, treated cells on PCL+HA random fibers had a significantly lower expression of miR-222 gene in comparison to TCP and PCL+HA aligned (##$p<0.05$) (FIG. 64).

The invention claimed is:

1. An in vitro model for the study of breast cancer cell dormancy in bone which comprises a microfibrous scaffold having a micron sized fiber dimension, whereby the scaffold is a three-dimensional (3-D) model; and
    the microfibrous scaffold contains a plurality of hydroxyapatite (HA) nanoparticles seeded with a low density amount of dormant breast cancer cells;
    wherein the micron sized fiber dimension has a diameter between 5.9 µm and 12.8 µm;
    and wherein the low density amount of dormant breast cancer cells are seeded onto the microfibrous scaffold at 31 cells/mm$^2$.

2. The in vitro model of claim 1, wherein the microfibrous scaffold is a microfibrous polycaprolactone; and
    the plurality of hydroxyapatite (HA) nanoparticles are 30 wt. % hydroxyapatite for mimicking bone tissue structure.

3. The in vitro model of claim 1, wherein the three-dimensional (3-D) model maintains the breast cancer cells in a dormant state unlike a two-dimensional (2-D) tissue culture plastic (TCP).

4. The in vitro model of claim 3, wherein the breast cancer cells remain viable and express stem cell markers for dormant breast cancer cells when seeded on the three-dimensional (3-D) model.

5. The in vitro model of claim 1, wherein the microfibrous scaffold has a random or an aligned fiber orientation.

6. The in vitro model of claim 1, wherein the microfibrous scaffold comprises a random fibrous mat or an aligned fibrous mat, and wherein the microfibrous scaffold comprises Poly (ε-caprolactone).

7. The in vitro model of claim 1, wherein the microfibrous scaffold is Poly (ε-caprolactone), and the hydroxyapatite (HA) nanoparticles are 30 wt. % hydroxyapatite.

8. The in vitro model of claim 7, wherein the microfibrous scaffold has a porosity of 79%±1.5% for a random fibrous mat, and 6.5%±1% for an aligned fibrous mat.

9. The in vitro model of claim 7, wherein the microfibrous scaffold comprises a random fibrous orientation or an aligned fibrous orientation having an average elastic modulus of 5.4 MPa±1.5 and an average ultimate tensile stress of 0.6 MPa±0.1 for the random fibrous orientation; and an average elastic modulus of 7.4±2.3 MPa and an average ultimate tensile strength of 0.52±0.34 Mpa for the aligned fibrous orientation.

* * * * *